(12) United States Patent
True

(10) Patent No.: US 8,883,691 B2
(45) Date of Patent: Nov. 11, 2014

(54) ENCODED MICROPARTICLES

(75) Inventor: Randall J. True, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 876 days.

(21) Appl. No.: 12/215,607

(22) Filed: Jun. 25, 2008

(65) Prior Publication Data

US 2009/0149340 A1    Jun. 11, 2009

Related U.S. Application Data

(60) Provisional application No. 60/946,127, filed on Jun. 25, 2007.

(51) Int. Cl.
    *C40B 30/04*    (2006.01)
    *G01N 33/543*   (2006.01)
    *G01N 21/64*    (2006.01)

(52) U.S. Cl.
    CPC . *G01N 33/54313* (2013.01); *B01J 2219/00558* (2013.01); *B01J 2219/0056* (2013.01); *B01J 2219/00502* (2013.01); *G01N 2021/6441* (2013.01); *B01J 2219/00513* (2013.01); *B01J 2219/00527* (2013.01); *B01J 2219/005* (2013.01); *B01J 2219/00547* (2013.01); *B01J 2219/00549* (2013.01); *G01N 33/54366* (2013.01)
    USPC .......................................................... 506/9

(58) Field of Classification Search
    None
    See application file for complete search history.

(56) References Cited

U.S. PATENT DOCUMENTS

| | | | |
|---|---|---|---|
| 5,800,992 | A | 9/1998 | Fodor et al. |
| 6,228,575 | B1 | 5/2001 | Gingeras et al. |
| 6,361,947 | B1 | 3/2002 | Dong et al. |
| 2003/0203390 | A1* | 10/2003 | Kaye et al. ................. 435/6 |
| 2004/0209376 | A1* | 10/2004 | Natan et al. ............... 436/56 |
| 2007/0037195 | A1 | 2/2007 | Ho |

FOREIGN PATENT DOCUMENTS

| | | |
|---|---|---|
| WO | WO 93/06121 A1 | 4/1993 |
| WO | WO 99/41006 A1 | 8/1999 |
| WO | WO 2007/081410 A2 | 7/2007 |
| WO | WO 2009/014848 A2 | 1/2009 |

OTHER PUBLICATIONS

True (Sep. 5, 2004) IEEE Engineering in Medicine and Biology Society vol. 4 pp. 2619 to 2622.*
Georqanopoulou (Feb. 4, 2005) Proceedings of the National Academy of Sciences USA vol. 102 pp. 2273 to 2276.*
Rosi (Mar. 23, 2005) Chemical Reviews vol. 105 pp. 1547 to 1562.*
Joshi (Aug. 4, 2005) Chemical Communications pp. 4471 to 4473.*
Joshi (Aug. 4, 2005) Chemical Communications pp. 4471 to 4473 supporting information.*
Bayerl, T.M., et al. Physical Properties of Single Phospholipid Bilayers Adsorbed to Micro Glass Beads, Biophys J., 58, 357-362 (1990).
Buranda, T., et al., Biomimetic Molecular Assemblies on Glass and Mesoporous Silica Microbeads for Biotechnology, Langmuir 19, 1654-1663 (2003).
Chee, Science 274:610-614 (1996).

(Continued)

*Primary Examiner* — Christian Boesen
(74) *Attorney, Agent, or Firm* — Cooley LLP

(57) ABSTRACT

Microparticles including spatially coded microparticles, systems for imaging and methods of detecting such microparticles as well as using the same in bioassays are provided.

28 Claims, 42 Drawing Sheets

(56) References Cited

OTHER PUBLICATIONS

Derisi, J.L., et al., Exploring the Metabolic and Genetic Control of Gene Expression on a Genomic Scale, Science 278:680-686 (1997).
Haab, B.B., et al., Protein Microarrays for Highly Parallel Detection and Quantitation of Specific Proteins and Antibodies in Complex Solutions, Genome Biology 2 (2): 0004.1-0004.13 (2001).
Lockhart, et al., Nature Biotehcnology, 14:1675-1680 (1996).
Maskos, U., Southern E.M. "Oligonucleotide Hybridizations on Glass Supports: a Novel linker for Oligonucleotide Synthesis an Hybridization Properties of Oligonucleotides Synthesized in Situ", Nucleic Acids Research, vol. 20, No. 7, pp. 1679-1684 (1992).
True, R.J., et al., "Microfabricated Templates for the Electrodeposition of Metallic Barcodes for use in Multiplexed Bioassays" IEEE—EMB Proceedings, 26 (IV), 2619-2622 (2004).
Walton, I.D., et al., "Particles for Multiplexed Analysis in Solution: Detection and Identification of Striped Metallic Particles Using Optical Microscopy", Anal. Chem., vol. 74, pp. 2240-2247 (2002).
PCT/US2008/68246, Search Report and Written Opinion, Jan. 29, 2009, 14 pgs.
Nicewarner-Pena, S.R., et al., "Submicrometer Metallic Barcodes," Science, Oct. 5, 2001, 5 pgs., vol. 294, The American Association for the Advancement of Science, Washington, D.C.
Xu, Hongxia., et al., "Multiplexed SNP genotyping using the Qbead(TM) system: a quantum dot-encoded microsphere-based assay," Nucleic Acids Research, 2003, vol. 31, No. 8 e43, 10 pgs. downloaded Feb. 4, 2011 from http://nar.oxfordjournals.org/content/31/8/e43.full.
Sha, M. Y., et al. "Multiplexed SNP genotyping using nanobarcode particle technology,", Anal. Bioanal. Chem., 2005, DOI 10.1007/s00216-005-0225-0. 10 pgs., Springer-Verlag.

* cited by examiner

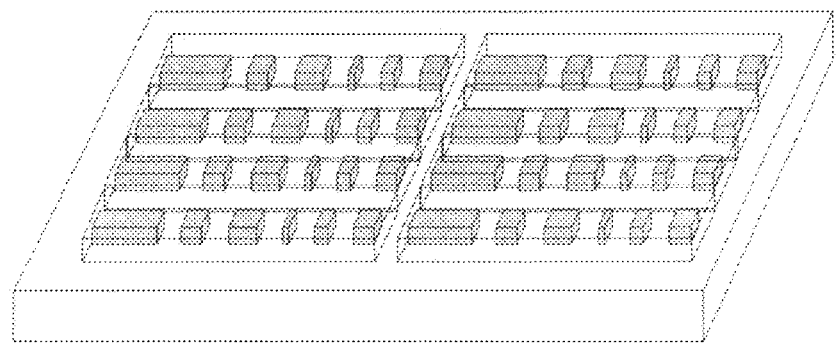
FIG. 7
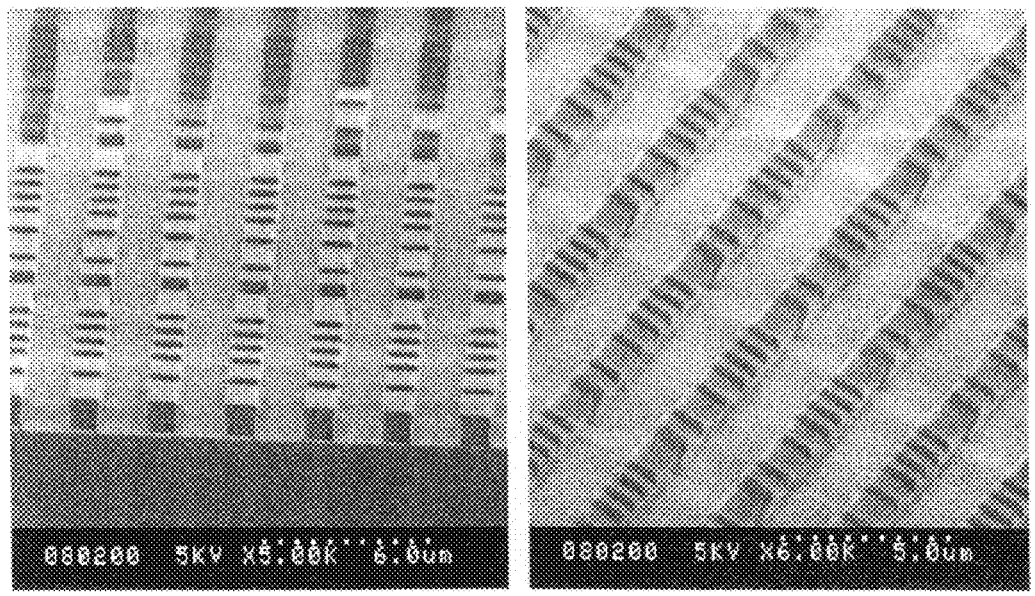
FIG. 8aFIG. 8b

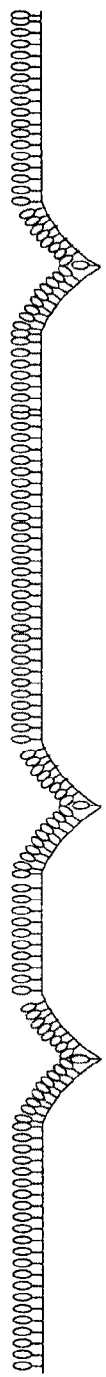
FIG. 26d
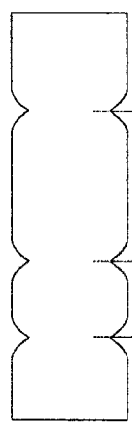
FIG. 26c
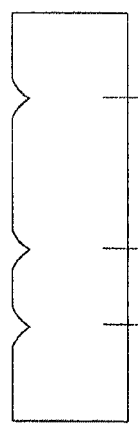
FIG. 27c
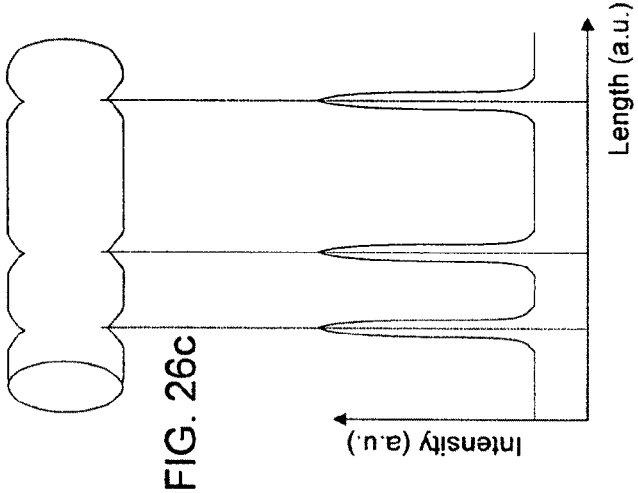
FIG. 26b
FIG. 27b
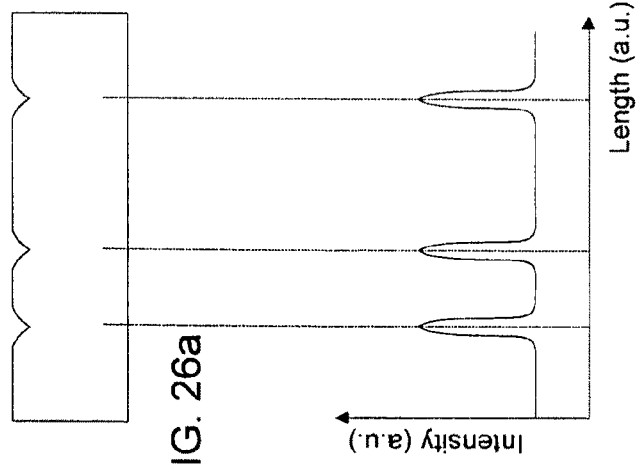
FIG. 26a
FIG. 27a

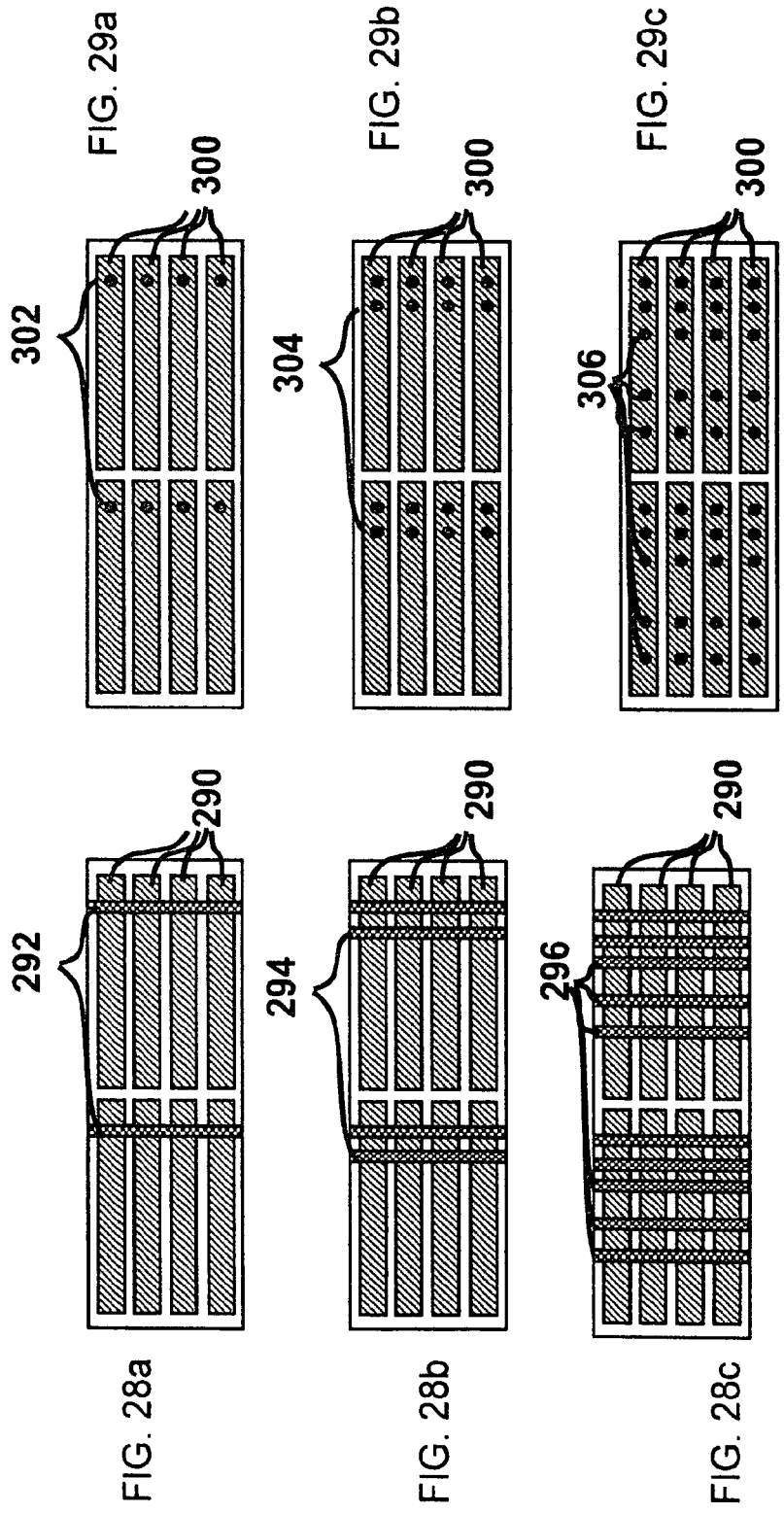

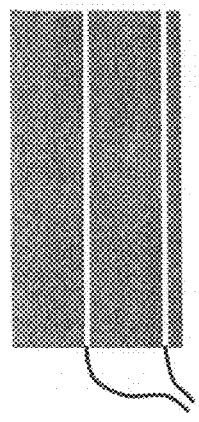
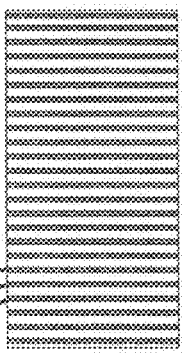
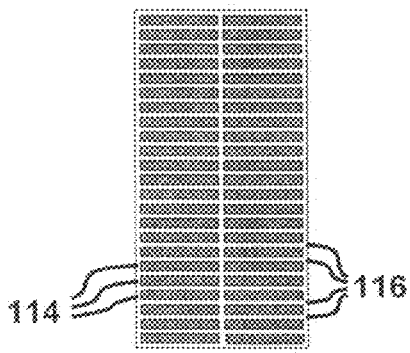
FIG. 30a     FIG. 30b     FIG. 30c
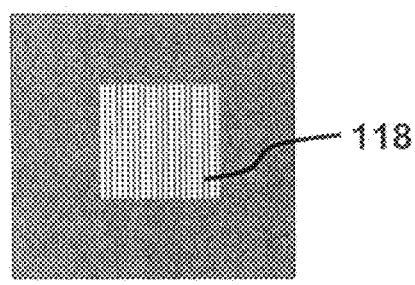
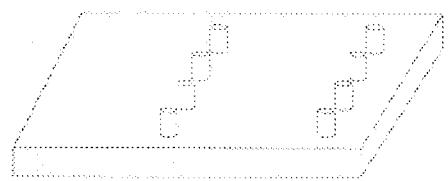
FIG. 30d     FIG. 31

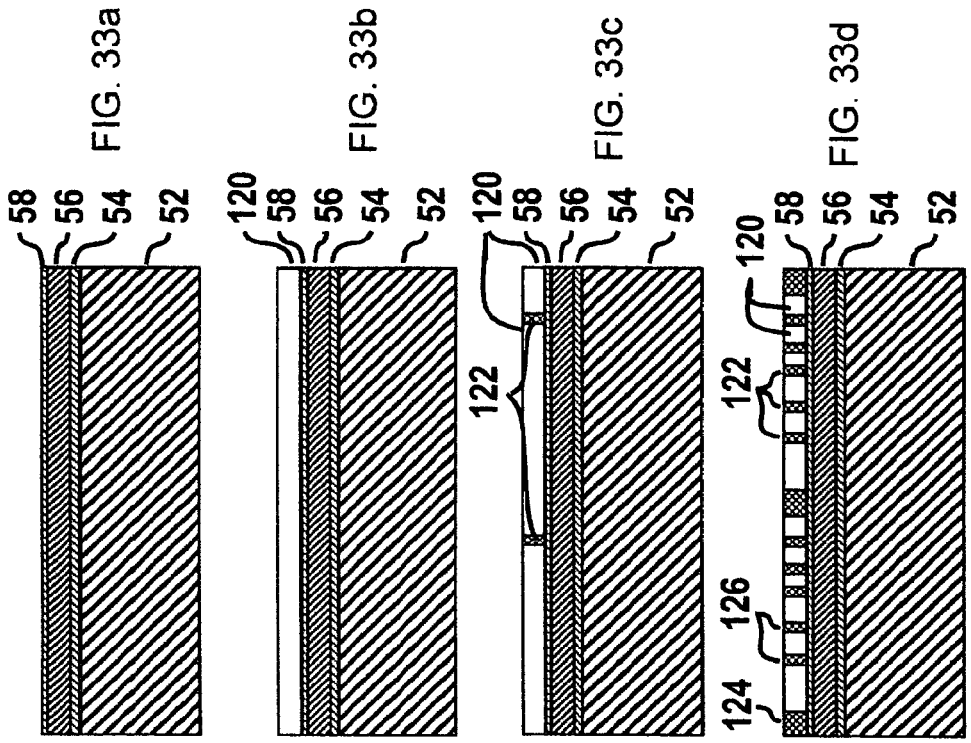

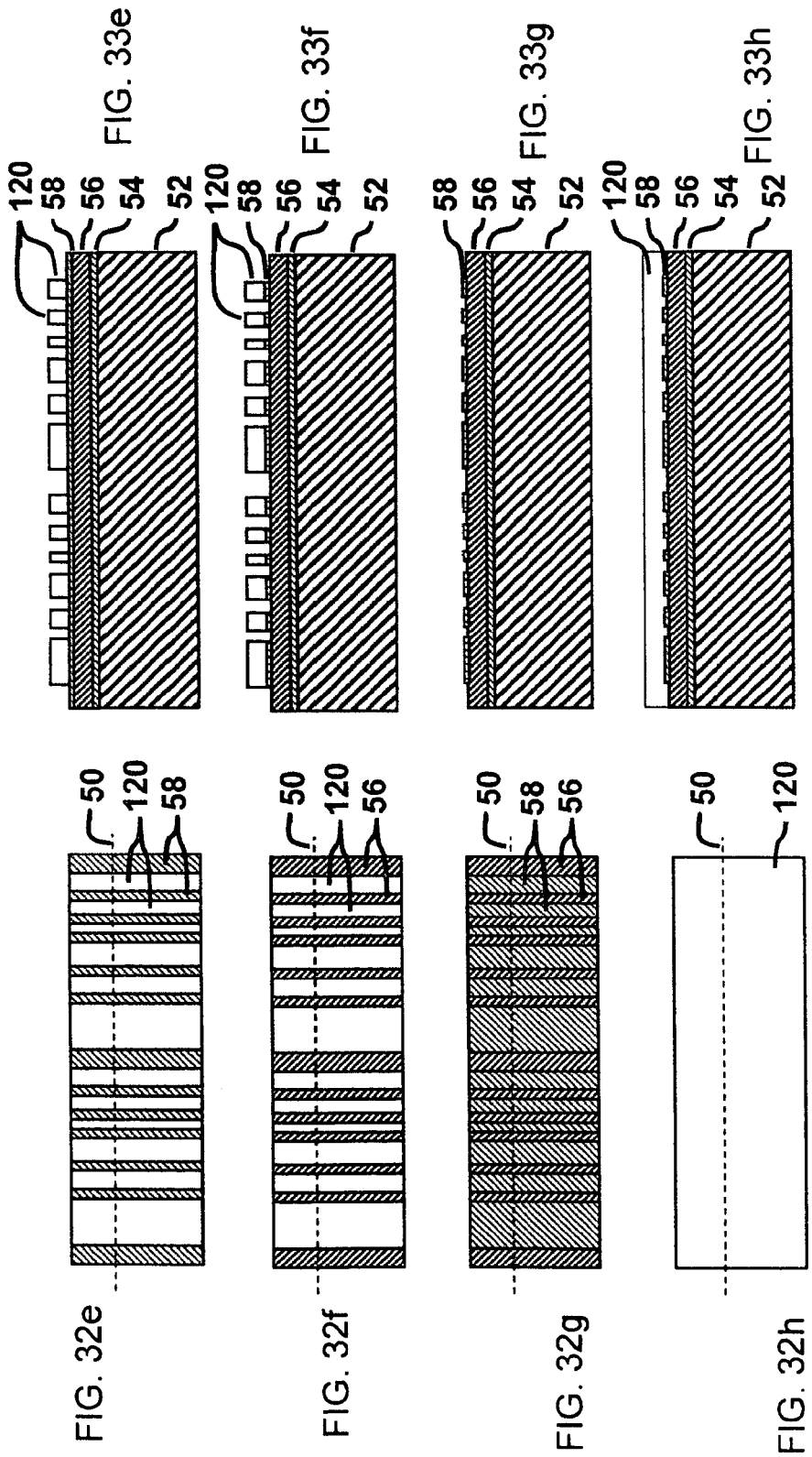

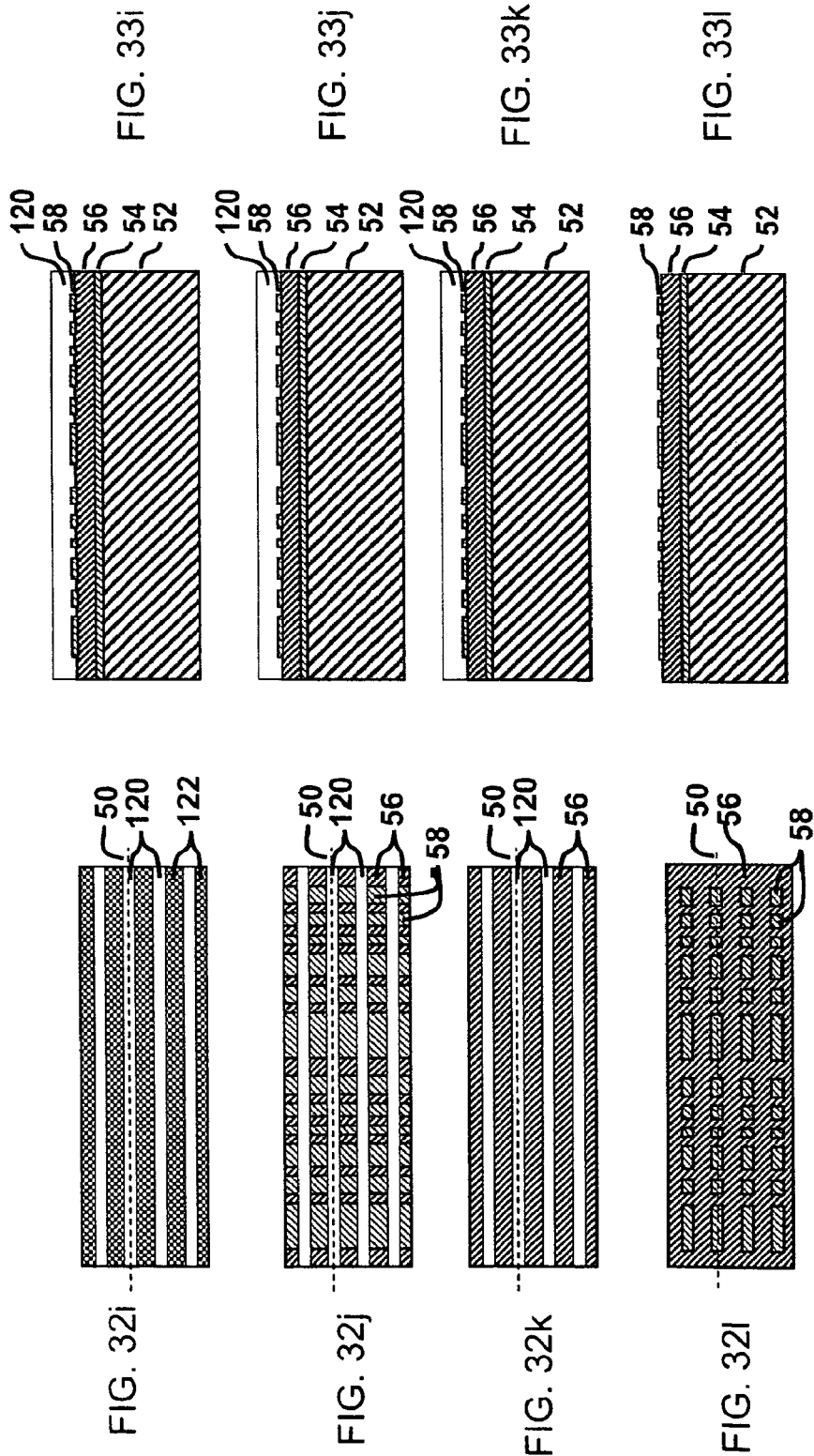

FIG. 36

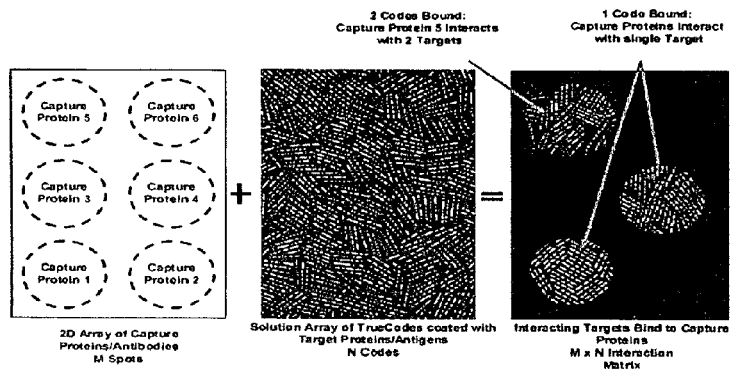
FIG. 50
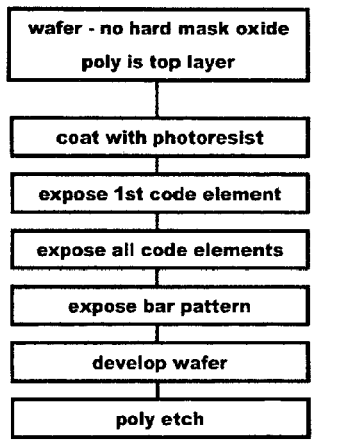
FIG. 51a
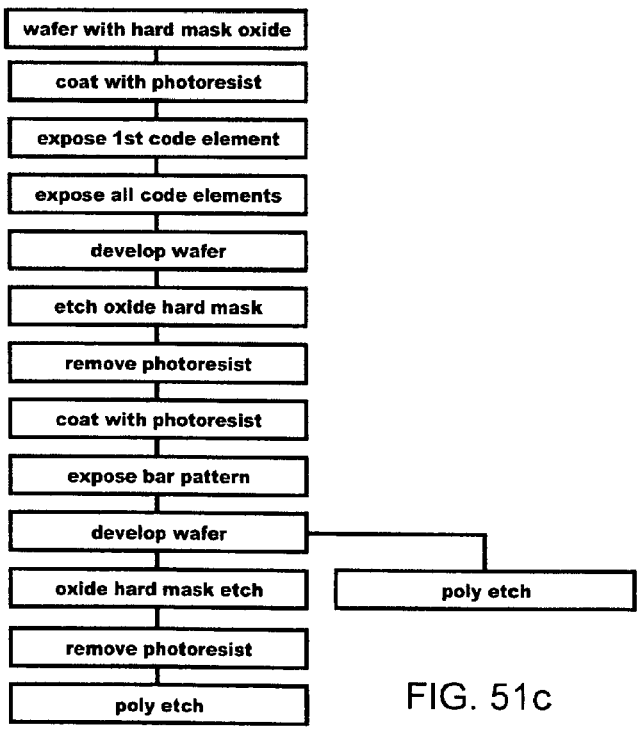
FIG. 51b
FIG. 51c

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Exemplary probe sequence
<220> FEATURE:
<221> NAME/KEY: misc_feature
<222> LOCATION: (1)..(1)
<223> OTHER INFORMATION: May have a fluorescent moiety attached

<400> SEQUENCE: 1
aaatcatcgg gagcattgtg                    20

<210> SEQ ID NO 2
<211> LENGTH: 20
<212> TYPE: DNA
<213> ORGANISM: Artificial Sequence
<220> FEATURE:
<223> OTHER INFORMATION: Exemplary target sequence
<220> FEATURE:
<221> NAME/KEY: misc_feature
<222> LOCATION: (1)..(1)
<223> OTHER INFORMATION: May have a fluorescent moiety attached

<400> SEQUENCE: 2
cacaatgctc ccgatgattt                    20

<210> SEQ ID NO 3
<211> LENGTH: 20
<212> TYPE: DNA
<213> ORGANISM: Artificial Sequence
<220> FEATURE:
<223> OTHER INFORMATION: Exemplary probe sequence
<220> FEATURE:
<221> NAME/KEY: misc_feature
<222> LOCATION: (1)..(1)
<223> OTHER INFORMATION: May have a fluorescent moiety attached

<400> SEQUENCE: 3
aacgcctggt cactgctatt                    20

<210> SEQ ID NO 4
<211> LENGTH: 20
<212> TYPE: DNA
<213> ORGANISM: Artificial Sequence
<220> FEATURE:
<223> OTHER INFORMATION: Exemplary target sequence
<220> FEATURE:
<221> NAME/KEY: misc_feature
<222> LOCATION: (1)..(1)
<223> OTHER INFORMATION: May have a fluorescent moiety attached

<400> SEQUENCE: 4
aatagcagtg accaggcgtt                    20

ENCODED MICROPARTICLES

CROSS REFERENCE

This application claims the benefit of U.S. Provisional Application No. 60/946,127 filed Jun. 25, 2007, which is incorporated herein by reference in its entirety.

BACKGROUND OF THE INVENTION

Microparticles or nanoparticles are often referred to as structures whose characteristic dimensions are on the order of micrometers or less, such as those with volumes of 1 mm$^3$ or less. Due to their unique properties arising from their small characteristic dimensions, microparticles have found distinguishable applications in laboratory research and many industrial fields. Encoded microparticles possess a means of identification and are an important subclass of the general field of microparticles. Because encoded particles carry information and can be physically tracked in space and time, they greatly extend the capabilities of non-encoded particles. A particularly important application for encoded microparticles is multiplexed bioassays, including those involving DNA and proteins. Other important fields for encoded microparticles include combinatorial chemistry, tagging, etc. Many biochemical and non-biochemical applications as will be discussed herein below.

For many applications, one more desirable attributes include: a large number of identifiable codes (i.e. a high codespace), accurate and reliable identification of the encoded particles, material compatibility for a particular application, low cost manufacturing of the microparticles (on a per batch, per particle, and per code set basis), and flexibility in the detection systems.

Several approaches to produce encoded microparticles have been developed in the past, such as fragmented colored laminates, colored polystyrene beads, quantum dot loaded polymer beads, rare-earth doped glass microbarcodes, electroplated metal nano rods, diffraction grating based fiber particles, and pattern bars and disks, and other types of microparticles. These technologies however suffer from any of a number of limitations, such as, insufficient codespace, high cost, inadequate precision, poor performance in applications, problematic clumping incapability of large scale manufacture, and complicated preprocessing or assay procedures.

Therefore, what is desired is an encoded microparticle or a set of encoded microparticles carrying coded information, methods of making the same, methods for providing the codes for microparticles, methods for fabricating the microparticles, methods and systems for detecting microparticle, and methods and systems for using.

References:

G. Steinberg, K. Stromsborg, et al. Strategies for Covalent Attachment of DNA to Beads. Biopolymers. Vol. 73, 597-605, 2004.

Maskos, U., Southern E. M. "Oligonucleotide hybridizations on glass supports: a novel linker for oligonucleotide synthesis and hybridization properties of oligonucleotides synthesized in situ" Nucleic Acids Research, Vol. 20, No. 7, pp. 1679-1684, 1992.

Zammatteo N., Jeanmart L., et al. "Comparison between Different Strategies of Covalent Attachment of DNA to Glass Surfaces to Build DNA Microarrays", Analytical Biochemistry, vol. 280, pp. 143-150, 2000.

Nicewarner-Pena, S. R., R. G. Freeman, B. D. Reiss, L. He, D. J. Pena, I. D. Walton, R. Cromer, C. D. Keating, and M. J. Natan, "Submicrometer Metallic Barcodes," Science, 294(5540), 137-141 (2001).

Walton, I. D., S. M. Norton, A. Balasingham, L. He, D. F. Oviso, D. Gupta, P. A. Raju, M. J. Natan, and R. G. Freeman, "Particles for multiplexed analysis in solution: detection and identification of striped metallic particles using optical microscopy," Anal. Chem., vol. 74, pp. 2240-2247, 2002.

True, R. J., M. K. Taylor, G. S. Chakarova, I. D. Walton, "Microfabricated templates for the electrodeposition of metallic barcodes for use in multiplexed bioassays," IEEE-EMB Proceedings, 26(IV), 2619-2622 (2004).

Xu, H. X., M. Y. Sha, E. Y. Wong, J. Uphoff, Y. H. Xu, J. A. Treadway, A. Truong, E. O'Brien, S. Asquith, M. Stubbins, et. al., "Multiplexed SNP genotyping using the Qbead™ system: a quantum dot-encoded microsphere-based assay," Nucleic Acids Res., 31(8), E43 (2003).

Han, M., X. Gao, J. Z. Su, S, Nie, "Quantum-dot-tagged microbeads for multiplexed optical coding of biomolecules," Nat. Biotechnol., 19(7), 631-635 (2001).

Haab, B. B., M. J. Dunham, & P. O. Brown. 2001. Protein microarrays for highly parallel detection and quantitation of specific proteins and antibodies in complex solutions. Genome Biology. 2(2): 0004.1-0004.13.

MacBeath, G., & S. L. Schreiber. 2000. Printing proteins as microarrays for high-throughput function determination. Science. 289; 1760-1763.

Brown, P. O., et al. 2001. The Mguide. http://cmgm.stanford.edu/pbrown/mguide/. Accessed 8 Feb. 2002.

DeRisi, J. L. V. R. Iyer, & P. O. Brown 1997. Exploring the metabolic and genetic control of gene expression on a genomic scale. Science. 278:680-686.

Fang Y, Frutos A G, Webb B, Hong Y, Ferrie A, Lai F, Lahiri J. Membrane biochips. Biotechniques. 2002 December; Suppl:62-5. PMID: 12514931.

Fang Y, Frutos A G, Lahiri J. G-protein-coupled receptor microarrays. Chembiochem. 2002 Oct. 4; 3(10):987-91.

Fulwyler et al., "Flow Microspheres Immunoassay for the Quantitative and Simultaneous Detection of Multiple Soluble Analytes," Methods in Cell Biology, 33, 613-629 (1990).

Bayerl, T. M. & Bloom, M. Physical properties of single phospholipid bilayers adsorbed to micro glass beads. Biophys. J. 58, 357-362 (1990).

Buranda, T. et al. Biomimetic molecular assemblies on glass and mesoporous silica microbeads for biotechnology. Langmuir 19, 1654-1663 (2003).

Chudin, E. et al. High-Throughput DNA Methylation Profiling Using Universal Bead Arrays, M. Bibikova, Z. Lin, L. Zhou, E. Genome Research, 16 (3), 383-393, March 2006.

D. Bowtell and J. Sambrook. 2003, DNA Microarrays, A Molecular Cloning Manual. Cold Spring Harbor Laboratory Press (in particular, sections 1-4).

G. T. Hermanson, Bioconjugate Techniques, 1996, Academic Press (Parts 1, 2 and 3).

Hacia J, Edgemon K, Sun B et al. "Two color hybridization analysis using high density oligonucleotide arrays and energy transfer dyes" Nucleic Acids Res, 1998, 26, 4249.

Di Giusto, D, and King, G C. "Single base extension (SBE) with proofreading polymerases and phosphorothioate primers: improved fidelity in single-substrate assays" Nucleic Acids Res., 31(3):e7 (2003).

Seo, T S, et al. "Four-color DNA sequencing by synthesis on a chip using photocleavable fluorescent nucleotides" PNAS, 102:5926-5931 (2005).

SUMMARY OF THE INVENTION

Microparticles including spatially coded microparticles, systems for imaging and methods of detecting such microparticles as well as using the same in bioassays are provided.

In one aspect of this invention there is provided an encoded microparticle comprising of a first material with two or more separate segments that are aligned along an axis to form a code and a second material that surrounds the first material so that the segments are detectable through the second material. In another aspect of this invention a multiplicity of encoded microparticles are provided.

In a further aspect of this invention there is provided a method of forming an encoded microparticle, including, the depositing and patterning of a layer on a substrate in a way that forms a plurality of microparticles, each of which has a plurality of separate segments aligned along an axis and represents a code; and the releasing separate microparticles from the substrate.

In one aspect of the invention there is provided a method of producing an encoded particle including the steps of providing a substrate, depositing a first layer and then a second layer on the substrate such that the second layer forms a plurality of particle regions each of which has two or more discrete segments aligned along an axis, depositing a third layer on the substrate and then releasing the layers in the particle regions from the substrate to form individual particles, each of which has a code formed by its discrete segments.

In another aspect of this invention there is provided a method of forming an encoded microparticle including the steps of depositing and patterning a layer on a substrate so as to form a plurality of microparticles, each of which has a plurality of discrete segments that are aligned along an axis that is substantially parallel to the substrate and represent a code, and releasing the separate microparticles from the substrate, whereby the code for each microparticle is detectable from all directions perpendicular to the axis.

In a further aspect of this invention there is provided an encoded microparticle comprising of a first material with two or more discrete segments aligned along an axis, a second material that is transparent and surrounds the first material such that the segments are detectable through the second material, and a code that is detectable from all angles orthogonal to the axis.

In one aspect of this invention there is provided an encoded microparticle including an elongated body with a plurality of alternating, adjacent portions transparent and less transparent material that represent a detectable code.

In another aspect of this invention there is provided a method of detecting an encoded microparticle comprising of providing a microparticle having a spatial code along an axis and a plurality of elongated sides, providing incident light onto the microparticle, and detecting the reflected or transmitted light wherein the code of the microparticle can be detected independent of which of the elongated sides the light is incident on.

In one aspect of this invention there is provided an encoded microparticle including an elongated structure with a detectable spatial code and a substantially square cross section, composed of a material opaque to visible or near visible light and a material transmissive to the visible or near visible light.

In another aspect of this invention there is provided an encoded microparticle comprising of a cuboid with an aspect ratio of a major surface orthogonal to the length of the microparticle greater than 3:1, a substantially square cross section when viewed orthogonally to the length of the microparticle, and with opaque and transparent portions that form the code of the microparticle.

In a further aspect of this invention there is provided an encoded microparticle with an optically identifiable code comprising of a particle body with a length from 5 to 100 microns, a width and height from 0.5 to 10 microns, and where the ratio of width to height ranges from 0.5 to 2.0.

In one aspect of this invention there is provided an encoded microparticle with a longest dimension less than 50 um, an outer surface substantially of glass and a spatial code that can be read with optical magnification.

In another aspect of this invention there is provided an encoded microparticle with a longest dimension less than 50 um, an outer surface substantially of glass and a spatial code comprising of code elements with a maximum size of 1.5 um or less.

In one aspect of this invention there is provided a wafer comprising of a plurality of unreleased encoded microparticles formed on the wafer, where the plurality of microparticles have at least 20 different codes and at least 1 million microparticles for each code.

In another aspect of this invention there is provided a wafer comprising of a plurality of unreleased encoded microparticles formed on the wafer, where the plurality of microparticles have at least 20 differently coded microparticle subsets with each subset comprising of at least 1 million microparticles.

In a further aspect of this invention there is provided a wafer comprising of a plurality of unreleased encoded microparticles where the number of microparticles on the wafer is greater than 1,000 microparticles per sqmm.

In one aspect of this invention there is provided a wafer comprising of a plurality of discrete die areas, with each die area having a plurality of encoded microparticles that are patterned but unreleased from the wafer, where the wafer has a surface area ranging from 12.5 in$^2$ to 500 in$^2$, and there are at least 3 million microparticles per in$^2$ of the wafer.

In one aspect of this invention there is provided a wafer comprising of a plurality of encoded silicon dioxide microparticles bonded to a top surface of the wafer where the top surface is a silicon surface.

In one aspect of this invention there is provided a method for releasing microparticles comprising of providing a silicon wafer with a plurality of encoded microparticles on it, bulk etching the silicon wafer so as to undercut the microparticles, and detach the microparticles from the silicon wafer.

In another aspect of this invention there is provided a silicon wafer with a plurality of unreleased encoded microparticles formed on it, with these encoded microparticles bonded to the silicon and having substantially the entire outer surface comprised of silicon dioxide, with a lower portion of the outer surface directly bonded to the silicon wafer.

In a further aspect of this invention there is provided a substrate having unreleased encoded microparticles comprising of a plurality of encoded microparticles connected to the substrate in the absence of an intervening sacrificial layer with the microparticles comprising a substantially transparent surface.

In one aspect of this invention there is provided a method of forming a plurality of encoded microparticles with a printing process to define a code for identifying the particle including the steps of providing a pattern that defines a single code element per microparticle region, printing a first code element with the pattern, printing a successive code element with the pattern so that the first and successive code elements are within the same microparticle region and provide a code.

In another aspect of this invention there is provided a method for forming a plurality of encoded microparticles comprising of printing at a first time a first portion of the codes of the microparticles; and printing at a second time after the first time a second portion of the codes of the microparticles so that the first portion and second portion form at least part the code for each microparticle.

In a further aspect of this invention there is provided a method of forming a plurality of encoded microparticles with a lithography process to define codes for the microparticles for identifying the microparticles that includes the steps of providing a substrate comprising a plurality of encoded microparticles, providing a pattern comprising identification elements, printing the pattern on the substrate or a portion of the substrate, laterally shifting the substrate by a predefined distance, and again printing the pattern on the substrate or a portion of the substrate.

In one aspect of this invention there is provided a system that includes a step and repeat exposure system capable of performing a method that includes printing at a first time a first portion of a code of a microparticle, printing at a second time after the first time a second portion of a code of the microparticle, and a computer readable medium having a sequence of computer executable instructions for controlling said step and repeat exposure system to perform said method.

In another aspect of this invention there is provided a computer readable medium including computer executable instructions for performing a method that includes directing a printing system to produce a set of encoded microparticles where the set comprises of a plurality of regions, each region includes a plurality of encoded microparticles all having the same code, and the computer program comprises a list of coordinate locations and lateral offsets that define the codes of the different regions.

In a further aspect of this invention there is provided a system comprising of a step and repeat exposure system capable of performing a method that includes the steps of printing at a first time a first portion of a code of a microparticle and printing at a second time after the first time a second portion of a code of the microparticle, wherein a computer readable medium has a sequence of computer executable instructions for controlling the step and repeat exposure system of the method.

In one aspect of this invention there is provided a method of forming a plurality of encoded microparticle with a lithography process to define a code for identifying the microparticles that includes the steps of providing a substrate, depositing a first layer, depositing a second layer, and forming the microparticle codes according to instructions of a step and repeat exposure system.

In another aspect of this invention there is provided a method for forming encoded microparticles that comprises the steps of depositing on a substrate a first layer to be patterned, depositing on the layer to be patterned a second layer that is a photoresist layer, forming an exposure pattern in the photoresist layer with a step and repeat exposure system by stepping a code element pattern across the photoresist layer, selectively removing the photoresist layer and patterning the first layer by the programmed step and repeat exposure system to form different microparticle codes on the same substrate, and separating the microparticles from the substrate.

In one aspect of this invention there is provided a method of forming a complete encoding pattern on a plurality of encoded microparticles with a lithography process to define codes for identifying the particles including the steps of providing a planar substrate on which the microparticles are to be formed, providing a $1^{st}$ pattern having a $1^{st}$ portion of an encoding pattern, exposing the substrate to the $1^{st}$ pattern to print the $1^{st}$ portion of the encoding pattern, and providing a $2^{nd}$ pattern having a $2^{nd}$ portion of an encoding pattern, exposing the substrate to the $2^{nd}$ pattern to print the $2^{nd}$ portion of the encoding pattern.

In another aspect of this invention there is provided a method of forming a complete encoding pattern on a plurality of encoded microparticles with a lithography process to define codes for identifying the particles comprising the steps of providing a planar substrate on which the microparticles are to be formed, performing a first lithography step having a $1^{st}$ portion of an encoding pattern, and performing a second lithography step having a $2^{nd}$ portion of an encoding pattern.

In one aspect of this invention there is provided a set of microparticles representing at least 100 different codes, where the microparticles are elongated microparticles with variable length coding elements that are spaced apart in a row and spaced between the coding elements are spaces having substantially the same space length.

In another aspect of this invention there is provided a kit comprising a plurality of microparticles representing at least 100 different codes where the microparticles are elongated microparticles with variable length coding elements spaced apart in a row, and spaced between the coding elements are spaces having substantially the same space length with the different codes having different probes bound to them.

In a further aspect of this invention there is provided a microparticle comprising of an elongated body with variable length coding elements spaced apart in a row and spaced between the coding elements are spaces having substantially the same space length of 1.5 microns or less.

In one aspect of this invention there is provided a method for differentiating microparticles comprising the steps of providing a set of microparticles representing at least 100 different codes with each microparticle being of elongated form with spaced apart variable length coding elements in a row with spaces therebetween, determining a position but not a length of the spaces in each microparticle in order to determine a code defined by the coding elements in the row, and differentiating microparticles having different codes based on the determined positions of the spaces for each microparticle.

In another aspect of this invention there is provided a coding scheme for encoded microparticles comprising of providing code elements that combine to form a code on an individual microparticle where the code elements are spaced apart from each other by predetermined spaces and where the predetermined spaces are smaller than the length of the code elements.

In one aspect of this invention there is provided a plurality of microparticles comprising of a layer of microparticles arranged on a surface with the microparticles disposed substantially in a monolayer that covers more than 30% of the area of a portion of the surface with the portion of the surface covered comprising an area that is greater than 1,000 square microns, and where the microparticles comprise spatial codes and have biochemical probes attached to them.

In another aspect of this invention there is provided a plurality of microparticles comprising of a layer of microparticles arranged on a surface with the microparticles disposed substantially in a monolayer on a portion of the surface at a density of at least 2,000 microparticles per square millimeter, where the microparticles comprise spatial codes and where the microparticles further comprise biochemical probes.

In a further aspect of this invention there is provided an imaging system comprising of a reservoir including a plurality of microparticles and a liquid, where the microparticles comprise spatial codes, are elongated and are arranged in a two dimensional layer at a density of 2,000 microparticles per square millimeter, a source of electromagnetic radiation, and a detector disposed to detect electromagnetic radiation after it is incident on the microparticles.

In one aspect of this invention there is provided an imaging system comprising of a reservoir including a plurality of microparticles and a liquid, where the microparticles comprise spatial codes, are disposed substantially in a monolayer that covers more than 30% of the surface area of the reservoir and an area greater than 1,000 square microns, a source of electromagnetic radiation, and a detector disposed to detect electromagnetic radiation after it is incident on the microparticles.

In another aspect of this invention there is provided a method of detecting codes of microparticles, comprising of providing a set of microparticles with each microparticle including a spatial code extending in a line or plane and with a layer of the microparticles arranged on an inner surface of a container during analysis that are disposed substantially in a monolayer on the inner surface, transmitting through or reflecting electromagnetic radiation from the microparticles, and detecting the transmitted or reflected electromagnetic radiation in order to detect the spatial codes of the individual microparticles where the microparticles are disposed on a portion of the surface and where the microparticles in the monolayer cover more than 30% of the area of the portion of the surface.

In a further aspect of this invention there is provided a computer readable medium having recorded on it an image comprising of pixels with the image being of a plurality of biochemically active microparticles including spatial codes and where the image comprises 50 microparticles per one million pixels in the image.

In one aspect of this invention there is provided a computer readable medium having recorded on it an image comprising of pixels with the image being of a plurality of biochemically active microparticles including spatial codes and where the pixels representing the microparticles occupy 30% or more of the total number of pixels.

In one aspect of this invention there is provided a method for detecting an analyte in a test fluid comprising of providing a set of biochemically active microparticles with each microparticle including a spatial code, the microparticles being configured such that they undergo substantial Brownian motion and where a layer of the microparticles is arranged on a surface during analysis, and detecting electromagnetic radiation from the microparticles in order to detect the spatial codes of the individual microparticles.

In another aspect of this invention there is provided a method for testing a biochemical sample comprising of providing a set of biochemically active microparticles with each microparticle including a spatial code, where the microparticles undergo a lateral displacement of 20 nm or greater in a time interval of one second or less and where a layer of the microparticles is arranged on a surface during analysis, and detecting electromagnetic radiation from the microparticles in order to detect the spatial codes of the individual microparticles.

In a further aspect of this invention there is provided a method for detecting the spatial codes of elongated microbarcodes comprising of providing the elongated microbarcodes with a biological material, binding the biological material on at least some of the microbarcodes with corresponding biological analyte in a test sample, providing the elongated microbarcodes in a test fluid, detecting electromagnetic radiation from the microbarcodes in order to detect the spatial codes of the individual microbarcodes, detecting fluorescence on at least some of the microbarcodes in order to determine the presence of molecular binding events, and where the microbarcodes undergo Brownian motion in the test fluid during the detection of the spatial codes and during the detection of the molecular binding events.

In one aspect of this invention there is provided a biochemically active, non-spherical microparticle comprising of a spatial code and an elongated shape that is disposed in an environment such that the microparticle undergoes Brownian motion in the liquid.

In one aspect of this invention there is provided a set of particles where the set comprises of at least 200 reservoirs with each reservoir including a group of particles that number at least 100,000 particles and have the same code, but with a code that is different from the codes of the particles in the other reservoirs.

In another aspect of this invention there is provided a set of wafers having unreleased particles with the set comprising of at least 200 different particle codes formed on the wafers in corresponding wafer areas with each wafer having a plurality of wafer areas with different particle codes formed in each area, and where each wafer area comprises at least 100,000 particles.

In a further aspect of this invention there is provided a kit comprising of a container, a buffer in the container, a plurality of microparticles in the buffer where different spatial codes are provided with the different groups of microparticles, with each group of microparticles sharing the same spatial code having on their surface the same oligonucleotide, but differing from oligonucleotides of other groups, and where the number of groups-sharing the same spatial code within the group is at least 1,200 with each group having a spatial code different from the other groups.

In one aspect of this invention there is provided a system for detecting a biologically active analyte including a plurality of microparticles arranged in a layer on a surface where the microparticles comprise probes and spatial codes, are disposed substantially in a monolayer, and where the microparticles are disposed on a portion of the surface such that the microparticles in the monolayer cover more than 30% of the portion of the surface.

In another aspect of this invention there is provided a device for detecting a biologically active analyte including a plurality of microparticles arranged in a layer on a surface where the microparticles comprise probes and spatial codes, are disposed substantially in a monolayer, and where the microparticles are disposed on a portion of the surface at a density of at least 2,000 microparticles per square millimeter.

In a further aspect of this invention there is provided a method of detecting a biologically active analyte including the steps of delivering a sample suspected of containing a biologically active analyte to be detected to a system comprising a monolayer of microparticles disposed on a portion of a surface where the microparticles comprise probes and spatial codes and where the microparticles are disposed on the portion of the surface such that the microparticles in the monolayer cover more than 30% of the portion of the surface, transmitting through or reflecting electromagnetic radiation from the microparticles, detecting the transmitted or reflected electromagnetic radiation in order to detect the spatial codes of the individual microparticles, and determining the presence or absence of a biologically active analyte by quantifying signals from the microparticles.

In one aspect of this invention there is provided a system for low volume detection of multiple biologically active analytes including a plurality of spatially coded microparticles where the plurality of microparticles comprise probes and greater than 200 spatial codes, and where the greater than 200 spatial codes can be optically detected in a sample volume less than 50 ul.

In another aspect of this invention there is provided a method of detecting a biologically active analyte in pooled subject samples including the steps of pooling greater than 50 subject samples suspected of containing a biologically active analyte, delivering the pooled samples to a system comprising a plurality of microparticles wherein the microparticles comprise probes and an encoding scheme, transmitting through or reflecting electromagnetic radiation from the microparticles, detecting the transmitted or reflected electromagnetic radiation in order to detect the spatial codes of the individual microparticles, and determining the presence or absence of a biologically active analyte by quantifying signals from the microparticles.

In a further aspect of this invention there is provided a method of rapidly detecting a biologically active analyte including the steps of delivering a sample suspected of containing a biologically active analyte to be detected to a system comprising greater than 100 differently encoded microparticles where the microparticles comprise probes and spatial codes, transmitting through or reflecting electromagnetic radiation from the microparticles, detecting the transmitted or reflected electromagnetic radiation in order to detect the spatial codes of the individual microparticles where the detection comprises detecting greater than 100 different encoded microparticles in less than 5 seconds, and determining the presence or absence of a biologically active analyte by quantifying signals from the microparticles.

In one aspect of this invention there is provided a method of controlling the quality of a biologically active analyte detection system including the steps of providing a master mixture of encoded microparticles where the microparticles comprise probes and spatial codes, dividing the master mixture into a plurality of sub-mixtures, testing a sub-mixture in a biologically active analyte detection system, determining the quality of the sub-mixture in the system where determining the quality comprises quantifying the reactivity of the microparticle probes with control samples to produce a quality result, recording the quality result, and associating the quality result with each sub-mixture.

In another aspect of this invention there is provided a business method comprising of screening one or more patient test sample for the presence or absence of a biologically active analyte using a system including a plurality of microparticles arranged in a layer on a surface where the microparticles comprise probes and spatial codes, are disposed substantially in a monolayer on the surface on a portion of the surface such that the microparticles in the monolayer cover more than 30% of the portion of the surface and where the screening produces data regarding the analyte, collecting the analyte data, and providing the analyte data to a patient, a health care provider or a health care manager for making a conclusion based on review or analysis of the data regarding a disease diagnosis.

In a further aspect of this invention there is provided a business method comprising screening one or more test sample for the presence or absence of a biologically active analyte using a system including a plurality of microparticles arranged in a layer on a surface where the microparticles comprise probes and spatial codes, are disposed substantially in a monolayer on the surface such that the microparticles in the monolayer cover more than 30% of the portion of the surface and where the screening produces data regarding the analyte, collecting the analyte data, and providing the analyte data to a biomedical or genetic researcher for making a conclusion based on review or analysis of the data regarding a biomedical or genetic study.

In one aspect of this invention there is provided a business method comprising screening patient test samples for the presence or absence of a biologically active analyte using a system including a plurality of microparticles arranged in a layer on a surface where the microparticles comprise probes and spatial codes, are disposed substantially in a monolayer on the surface such that the microparticles in the monolayer cover more than 30% of the portion of the surface and where the screening produces data regarding the analyte, collecting the analyte data into a database, using one or more algorithm to process the collected analyte data to identify one or more diagnostic, therapeutic or marker products, and collaboratively or independently, marketing or commercializing the products.

Such objects of the invention are achieved in the features of the independent claims attached hereto. Preferred embodiments are characterized in the dependent claims. In the claims, only elements denoted by the words "means for" are intended to be interpreted as means plus function claims under 35 U.S.C. §112, the sixth paragraph.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1b is a side view cross-section of the microparticle in FIG. 1a;

FIG. 7 is a perspective view of an array of microparticles on a substrate during the fabrication;

FIGS. 26a to 26c show schematic diagrams of encoded microparticles of the present invention with surface indentations that form a spatial code;

FIG. 26d shows an example of encoded microparticles comprising indentations;

FIGS. 27a to 27c show the non-uniform aerial density measured normal to the particle surface for corresponding particles in FIGS. 26a to 26c;

FIG. 28a to FIG. 29c are top views of microparticles according to another example of the invention during another exemplary fabrication of the invention;

FIG. 30a to 30c show drawings of the 3 mask fields of the preferred embodiment of the microparticle structure and FIG. 30d shows a drawing of a reticle plate;

FIG. 31 shows an alternate example of the general method of generating code using multiple print steps utilizes stamping;

FIG. 32a to FIG. 32m illustrate the microfabrication process steps of the example encoded microparticle of FIG. 1a;

FIG. 33a to FIG. 33m show the corresponding cross sectional views of the microparticle in FIG. 32a to FIG. 32m;

FIG. 36 shows charts of example data that is input into the stepper software to generate different codes on every die on a wafer;

FIG. 50 is a schematic that includes images of particles but is not the result of an actual experiment of this invention;

FIGS. 51a to 51c show flowcharts of examples of the code element patterning and etch steps;

DETAILED DESCRIPTION OF THE INVENTION

Figure 1A:
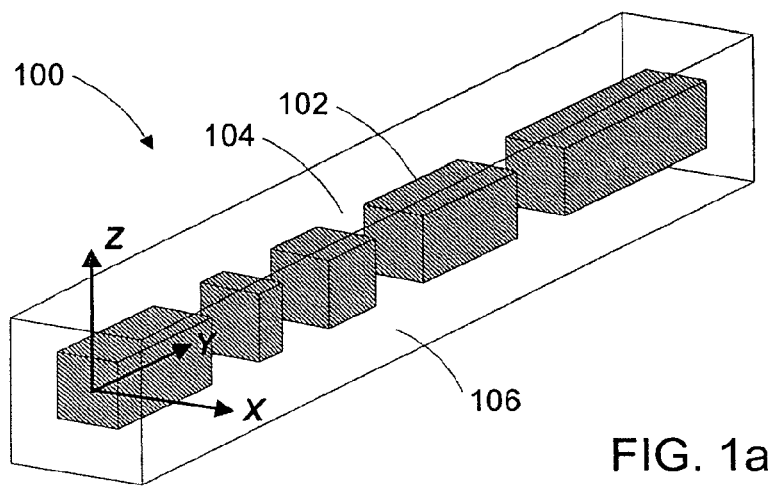
FIG. 1a schematically illustrates an encoded microparticle of the invention.

An encoded microparticle is provided carrying a code, and a set of encoded microparticles are provided with distinguishable codes, wherein the codes comply with a pre-determined coding scheme.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

Definitions

The term "biologically active analyte" when used herein means any substance which can affect any physical or biochemical properties of a biological organism, including but not limited to viruses, bacteria, fungi, plants, animals, and humans. In particular as used herein, biologically active analyte according to the present invention includes without limitation drugs, prodrugs, pharmaceutical agents (e.g. a pharmaceutically active compound), drug metabolites, biomarkers such as expressed proteins and cell markers, antibodies, serum proteins, cholesterol, polysaccharides, nucleic acids, biological analytes, gene, protein, or hormone, or any combination thereof. A biologically active analyte can further include a natural or man-made substance including but not limited to a gas, a chemical agent or a pollutant, or a combination thereof (e.g., from an environmental source). At a molecular level, the biologically active analytes can be polypeptide glycoprotein, polysaccharide, lipid, nucleic acid, and a combination thereof. Biologically active analytes further include various phosphorylation and glycosylation states of biomolecules.

Of particular interest are biomarkers associated with a particular disease or with a specific disease stage. Such biologically active analytes include but are not limited to those associated with autoimmune diseases, obesity, hypertension, diabetes, neuronal and/or muscular degenerative diseases, cardiac diseases, endocrine disorders, any combinations thereof.

Also of interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are biologically active analytes that are indicative of a microorganism. Exemplary microorganisms include but are not limited to bacterium, virus, fungus and protozoa. Biologically active analytes that can be detected by the subject method also include blood-born pathogens selected from a non-limiting group that consists of *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans.*

Biologically active analytes that can be detected by the subject device and methods also encompass a variety of sexually transmitted diseases selected from the following: gonorrhea (*Neisseria gorrhoeae*), syphilis (*Treponema pallidum*), chlamydia (*Chlamydia tracomitis*), nongonococcal urethritis (*Ureaplasma urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional biologically active analytes that can be detected by the subject apparatus and methods encompass a diversity of respiratory pathogens including but not limited to *Pseudomonas aeruginosa*, methicillin-resistant *Staphylococcus aureus* (MSRA), *Klebsiella pneumoniae, Haemophilus influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsiella oxytoca, Pseudomonas fluorsecens, Neisseria meningitidis, Streptococcus pyogenes, Pneumocystis carinii, Klebsiella pneumoniae, Legionella pneumophila, Mycoplasma pneumoniae,* and *Mycobacterium tuberculosis.*

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alpha-fetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancreas markers include without limitation Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx), Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone glaprotein), Alkaline phosphatase, Cathepsin K, COMP (Cartilage Oligomeric Matrix Protein), Osteocrin, Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin. DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, T-suppressor cell antigen, T-cell antigen ratio, T-helper cell antigen, Anti-HCV, Pyrogens, p24 antigen, Muramyl-dipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII:, Antihemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibody markers include those for EGFR, ErbB2, and IGF1R.

Exemplary protein kinase markers include tyrosine-specific kinases and serine/threonine-specific kinases as well known in the art.

Exemplary tyrosine kinase inhibitor markers include without limitation Ab1, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threonine Kinase Inhibitor markers include without limitation AKT, Aurora A/B/B, CDK, CDK (pan), CDK1-2, VEGFR2, PDGFRb, CDK4/6, MEK1-2, mTOR, and PKC-beta.

GPCR target markers include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

For the purposes of this invention, a "therapeutic agent" is intended to include any substances that have therapeutic utility and/or potential. Such substances include but are not limited to biological or chemical compounds such as a simple or complex organic or inorganic molecules, peptides, proteins (e.g. antibodies) or a polynucleotides (e.g. anti-sense). A vast array of compounds can be synthesized, for example, polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters rapidly from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the PD parameters fall outside the desired range during a treatment regime, immediate action may have to be taken as well.

In preferred embodiments physical parameter data is stored in or compared to store profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the microparticle system for improved accuracy in determining drug pathways and efficacy in cancer studies.

The term "binding-pair" includes any of the class of immune-type binding-pairs, such as, antigen/antibody, antigen/antibody fragment, or hapten/anti-hapten systems; and also any of the class of nonimmune-type binding-pairs, such as biotin/avidin, biotin/streptavidin, folic acid/folate binding protein, hormone/hormone receptor, lectin/specific carbohydrate, enzyme/enzyme enzyme/substrate, enzyme/inhibitor, or, vitamin B 12/intrinsic factor. They also include complementary nucleic acid fragments (including DNA sequences, RNA sequences, and peptide nucleic acid sequences), as well as Protein A/antibody or Protein G/antibody, and polynucleotide/polynucleotide binding protein. Binding pairs may also include members that form covalent bonds, such as, sulfhydryl reactive groups including maleimides and haloacetyl derivatives, and amine reactive groups such as isothiocyanates, succinimidyl esters, carbodiimides, and sulfonyl halides.

The term "nucleic acid" when used herein refers to deoxyribonucleotides, deoxyribonucleosides, ribonucleosides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "microorganism" when used herein refers to bacteria, actinomycetales, cyanobacteria (unicellular algae), fungi, protozoa, animal cells or plant cells or virus. Examples of microorganisms include but are not limited to pathogens.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins (i.e., antigens), wherein the amino acid residues are linked by covalent peptide bonds. In addition, proteins that contain multiple polypeptide chains that associate through covalent and/or non-covalent interactions are also encompassed by "protein," as used herein.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "individual" when used herein is not limited to a human being, but may also include other organisms including but not limited to mammals, plants, bacteria or cells derived from any of the above.

Aspects of the invention may include one or more of the following advantageous features. Preferably, the microparticles in the examples below have a volume of 1 $mm^3$ or less. The microparticle of the invention enables fast, precise and less complicated detection of the code. Methods for providing the codes on microparticles, methods for fabricating the microparticles, methods and systems for detecting the microparticle, and methods and systems for using the microparticles are also disclosed.

In the following, the invention will be discussed with reference to specific examples. It will be appreciated by those skilled in art that the following discussion is for demonstration purposes, and should not be interpreted as a limitation. Instead, other variations without departing from the spirit of the invention are also applicable.

Overall Structure of the Microparticle

As an example, FIG. 1a schematically illustrates an encoded microparticle of the invention. Microparticle 100 is a cuboid structure elongated along the Y direction in the Cartesian coordinate as shown in the figure. The cross-sections perpendicular to the length of the microparticle have substantially the same topological shape—which is square in this example.

The microparticle in this particular example has a set of segments (e.g. segment 102) and gaps (e.g. gap 104) intervening the segments. Specifically, segments with different lengths (the dimension along the length of the microparticle, e.g. along the Y direction) represent different coding elements; whereas gaps preferably have the same length for differentiating the segments during detection of the microparticles. The segments of the microparticle in this example are fully enclosed within the microparticle, for example within body 106. As an alternative feature, the segments can be arranged such that the geometric centers of the segments are aligned to the geometric central axis of the elongated microparticle. A particular sequence of segments and gaps represents a code. The codes are derived from a pre-determined coding scheme.

Segments of the microparticle can be any suitable form. In an example of the invention, each segment of the microparticle has a substantially square cross-section (i.e. the cross-section in the X-Z plane of a Cartesian coordinate as shown in FIG. 1a) taken perpendicular to the length (i.e. along the Y direction in the Cartesian coordinate in FIG. 1a) of the microparticle. The segments may or may not be fabricated to have substantially square cross-section. Other shapes, such as rectangular, circular, and elliptical, jagged, curved or other shapes are also applicable. In particular, the code elements—i.e. segments and gaps, may also take any other suitable desired shape. For example, the segment (and/or the gaps) each may have a cross-section that is rectangular (e.g. with the aspect ratio of the rectangular being 2:1 or higher, such as 4:1 or higher, 10:1 or higher, 20:1 or higher, or even 100:1 or higher, but preferably less than 500:1).

The microparticle example of FIG. 1a has six major surfaces, namely surfaces of $(X=\pm x_0, Y, Z)$, surfaces $(X, Y, Z=\pm z_0)$, and surfaces $(X, Y=\pm y_0, Z)$, wherein $x_0$, $y_0$, and $z_0$ are respectively the width, length, and height of the microparticle. According to the invention, at least two of the above six surfaces $X \pm x_0$ (or surfaces $Z=\pm z_0$), more preferably four of the above six major surfaces $X=\pm x_0$, surfaces $Z=\pm z_0$ are substantially continuous, regardless of whether each surface has or does not have indentations. With this configuration, the microparticle exhibits substantially the same geometric appearance and specific properties to the detector—such as an optical imaging apparatus. In fact, the major surfaces can be made substantially flat. For example, even though roughness or varying profiles may be caused during fabrication, substantially flat major surfaces can still be obtained using standard surface machining techniques, such as over-deposit and etch back or chemical-mechanical-polishing (CMP) techniques, as well as proper control of patterning steps to create smooth vertical sidewall profiles.

The code elements, i.e. the segments and gaps, may take any desired dimensions. As an example of the invention, each coding structure has a characteristic dimension that is 5 um (microns) or less, such as 3 microns or less, and more preferably 1 micron or less, such as 0.8 or 0.5 microns or less. In particular, when gaps are kept substantially the same dimension while the segments vary in dimension, each gap preferably has a characteristic dimension that is 1.5 microns or less, such as 0.8 or 0.5 microns or less.

As one example, if forming the microparticles on a 12-inch silicon wafer with 0.13 line widths, the gap areas can be made to have 0.13 um minimum widths, with the less transparent segments having widths of from 0.13 um to much larger (depending upon the desired length of the particle and the encoding scheme and code space desired). Minimum gap widths, as well as minimum segment widths, of from 0.13 to 1.85 um (e.g. from 0.25 to 0.85 um) are possible depending upon the wafer fabrication used. Of course larger minimum gap and segment lengths (e.g. 1.85 to 5.0 um, or more) are also possible. Other sized wafers (4 inch, 6 inch, 8 inch etc.) can of course be used, as well as wafers other than silicon (e.g. glass), as well as other substrates other than silicon (larger glass panels, for example).

Though the microparticle may have the same length in the X, Y and/or Z directions, preferably the encoded microparticle has a ratio of the length to width of from 2:1 to 50:1, e.g. from 4:1 to 20:1. In an example of the invention, the microparticle has a length (e.g. the dimension along the Y direction) of 70 microns or less, 50 microns or less, 30 microns or less, such as 20 microns or less, 16 microns or less, or even 10 microns or less. The width (e.g. the dimension along the X direction), as well as the height (the dimension along the Z direction), of the microparticle can be 15 microns or less, 10 microns or less, 8 microns or less, 4 microns or less, or even 1 microns or less, such as 0.13 micron. Widths as small as from 0.5 to 2 microns are also possible. Other than the shape as shown in FIG. 1a and discussed above, the microparticle may take a form of rod, bar, disk or any other desired shapes.

The coding structures and gaps of the microparticles can take any suitable form as long as the coding structures and gaps together represent detectable codes. The term "detectable code" as used herein means the code of a given microstructure that is not masked, obscured or otherwise cannot be read, for example, optically or otherwise. As mentioned above, the cross-section of the microparticles, as taken perpendicular to the length of the particle, can be square, rectangular, circular, elliptical, or any desired shape such as jagged or curved shapes or other profiles. When the cross-section is rectangular, the rectangle preferably has an aspect ratio (the ratio of the length to the width or height) of 2:1 or higher, such as 4:1 or higher, 10:1 or higher, 20:1 or higher, or even 100:1 or higher, but preferably less than 500:1. The ratio of the width to height can be around 1:1 (square cross section), or have a ratio of from 1:4 to 1:1—preferably a ratio that allows the particle to rest on either the sides defining the width or height of the particle such that the code of the microparticle can be detected regardless of which of the elongated sides the particle rests.

To facilitate fast, cost-effective, reliable, and easy detection of the code represented by the coding structures and gaps, it is preferred that each coding structure is as omni-directional as possible to the detection means. That is—each coding structure exhibits substantially the same geometric appearance or detectable properties when observed from at least two directions, more preferably from four (or all, if not four-sided in cross section) directions perpendicular to the length of the microparticle. Accordingly, the coding structures preferably possess rotational symmetry along the length of the microparticle, such as 2-folded or 4-folded rotational symmetry.

A microparticle of the invention can have any suitable number of coding structures depending upon the shape or length of the particle, and the code space desired. Specifically, the total number of coding structures of a microparticle can be from 1 to 20, or more typically from 3 to 15, and more typically from 3 to 8.

The desired code can be incorporated in and represented by the microparticle in many ways. As an example, the coding elements of the pre-determined coding scheme can be represented by the segment(s)—e.g. segments of different lengths represent different coding elements of the coding scheme. Different spatial arrangements of the segments with the different (or the same) lengths and intervened by gaps represent different codes. In this code-incorporation method, the intervening gaps preferably have substantially the same dimension, especially the length in the direction to which the segments are aligned. As another example, the codes are incorporated in the microparticle by arranging gaps that vary in lengths; while the segments have substantially the same dimension and are disposed between adjacent gaps. In another example, the both segments and gaps vary in their dimensions so as to represent a code. In fact, the code can also be represented in many other alternative ways using the segments, gaps, and the combination thereof.

For representing a code derived from the predetermined coding scheme, the segments and gaps are arranged along the length (the Y direction) of the elongated microparticle (2D, or even 3D, arrangements however are also possible). Specifically, the segments and gaps are alternately aligned along the length with the each segment being separated (possibly fully separated and isolated) by adjacent gaps; and each gap is separated (possibly fully separated and isolated) by adjacent segments, which is better illustrated in a cross-sectional view in FIG. 1b, which will be discussed in the following.

In an example of the invention, any suitable number of segments can be used—e.g. from 2 to 20, or more typically from 3 to 15 segments (more typically from 3 to 8 segments) of less transparent material (as compared to the intervening gaps between the segments) are provided within the encoded microparticle. To form the code, it is possible that the segments of less transparent material are varying lengths. Alternatively, the segments of less transparent material could each have substantially the same length whereas the intermediate segments of more transparent material could have varying lengths. Of course, the segments of more transparent material and the intermediate segments of less transparent material could both have varying lengths in order to represent the code.

Figure 1B:
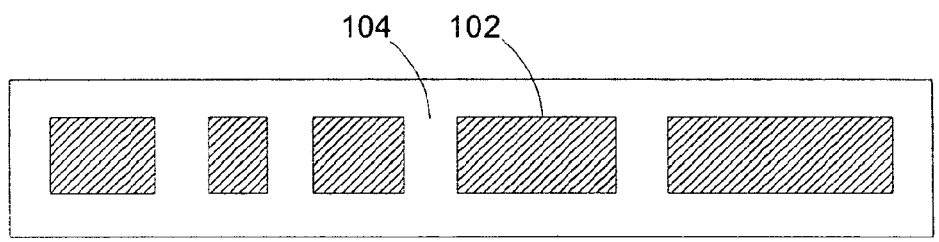

Referring to FIG. 1b, the cross-section is taken in the Y-Z plane (or equivalently in the X-Y plane) of the particle in FIG. 1a. Segments (e.g. segment 102) and gaps (e.g. gap 104) alternate along the length of the microparticle.

In order to enable detection of codes incorporated in microparticles, the segments and gaps in each microparticle can be composed of materials of different optical, electrical, magnetic, fluid dynamic, or other desired properties that are compatible with the desired detection methods. In one example the segments and gaps are directly spatially distinguishable under transmitted and/or reflected light in the visible spectrum. For example, when the code detection relies upon optical imaging, the distinguishable property (segments vs. gaps) can be a difference in transmissivity to the particular light used for imaging (which can be any desired electromagnetic radiation—e.g. visible and near-visible light, IR, and ultraviolet light. The segments can be made to be more light absorbing (or light reflecting) than the intervening spacing material (or vice versa). When the code detection relies upon the electrical property measurements, the property can be resistance and conductance. When the code detection involves magnetic methods, the properties can be inductance and electro-inductance. When the code detection involves fluid dynamic methods, the property can be viscosity to the specific fluid used in the code detection. Regardless of which specific property is relied upon, the segments and gaps are preferred to exhibit sufficient difference in the specific property such that the difference is detectable using the corresponding code detection method. In particular, when the code is to be detected by means of optical imaging, the segments and gaps are composed of materials exhibiting different transmissivity (in an optical transmittance mode) or reflectivity (in optical reflectance mode) to the specific light used in imaging the microparticles. For example, the segments of the microparticle of the less transparent material can block and/or reflect 30% or more, preferably 50% or more, or e.g. 80% or more, of the visible light or near visible light incident thereon.

Given the fact that transmissivity of electromagnetic radiation through an object varies with the thickness of the object, it is preferred that the segments that are capable of blocking and/or reflecting 30% or more, preferably 50% or more, or e.g. 80% or more (or even 90% or more), of the detection light; while the gaps between the coding structures are provided from materials and at dimensions that are capable of transmitting 50% or more, 70% or more, 80% or more, or even 90% or more of the detecting light. Alternatively, the segments and gaps are composed of different materials such that the ratio of the transmissivity difference is sufficient to detect the code$\gamma$, e.g. is 5% or more, 10% or more, 20% or more, 50% or more, and 70% or more. The transmissivity is defined as the ratio of the light intensities of the passed light to the incident light.

The microstructure can be made of organic and/or inorganic materials or a hybrid of organic and inorganic material. Specifically, the gaps (which are preferably more transmissive to visible or near-visible light) and segments (which are preferably less transmissive to visible or near-visible light as compared to gaps) each can be composed organic or inorganic materials, or a hybrid organic-inorganic material. The segments can be composed of a metal (e.g. aluminum), an early transition metal (e.g. tungsten, chromium, titanium, tantalum or molybdenum), or a metalloid (e.g. silicon or germanium), or combinations (or nitrides, oxides and/or carbides) thereof. In particular, the segments can be composed of a ceramic compound, such as a compound that comprises an oxide of a metalloid or early transition metal, a nitride of a metalloid or early transition metal, or a carbide of a metalloid or early transition metal. Early transition metals are those from columns 3b (Sc, Y, Lu, Lr), 4b (Ti, Zr, Hf, Rf), 5b(V, Nb, Ta, Db), 6b (Cr, Mo, W, Sg) and 7b (Mn, Tc, Re, Bh) of the periodic table. However, preferred are early transition metals in columns 4b to 6b, in particular tungsten, titanium, zirconium, hafnium, niobium, tantalum, vanadium and chromium.

The gaps which are in this example more transparent, can comprise any suitable material that is more transparent than the segments. The spacing material can be a siloxane, siloxene or silsesquioxane material, among others, if a hybrid material is selected. The spacing material, if inorganic, can be a glass material. Thin film deposited silicon dioxide is a suitable material, with or without boron or phosphorous doping/alloying agents. Other inorganic glass materials are also suitable such as silicon nitride, silicon oxynitride, germanium oxide, germanium oxynitride, germanium-silicon-oxynitride, or various transition metal oxides for example. A spin on glass (SOG) could also be used. If an organic material is used for the gap material, a plastic (e.g. polystyrene or latex for example) could be used.

Both the segments and the gaps can be deposited by any suitable methods such as CVD (chemical vapor deposition), PVD (physical vapor deposition), spin-on, sol gel, etc. If a CVD deposition method is used, the CVD could be LPCVD (low pressure chemical vapor deposition), PECVD (plasma enhanced chemical vapor deposition), APCVD (atmospheric pressure chemical vapor deposition), SACVD (sub atmospheric chemical vapor deposition), etc. If a PVD method is used, sputtering or reactive sputtering are possible depending upon the desired final material. Spin on material (SOG or hybrid organic-inorganic siloxane materials As a more specific example, the segments can be comprised of a any suitable silicon material such as CVD (chemical vapor deposition) deposited amorphous silicon. Polysilicon or single crystal silicon area also suitable as are a wide range of other materials as mentioned above. It is preferred, but not necessary, that the material selected for the segments has a high degree of deposition thickness control, low surface roughness, control of etching—both patterning and release (e.g. using a dry plasma etch for patterning and a wet or dry chemical etch for release), and CMOS process compatibility. The gap material can be CVD deposited silicon dioxide. The silicon dioxide may include doping/alloying materials such as phosphorous or boron. Temperature considerations may be taken into account in choosing a combination of more and less transparent materials for the segments and gaps.

Figure 2:
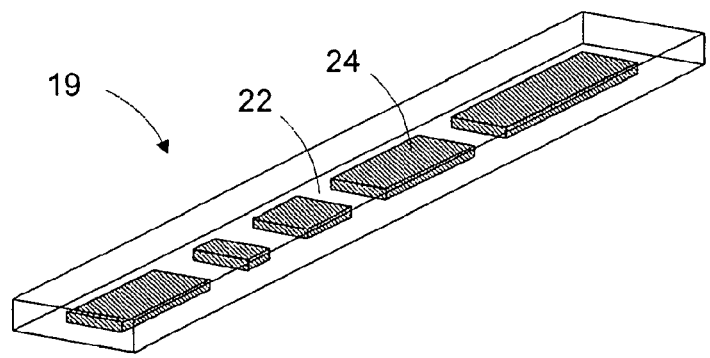
FIG. 2 schematically illustrates another example encoded microparticle of the invention.

FIG. 2 schematically illustrates another example encoded microparticle of the invention. Particle 20 has a rectangular cross section and is of a substantially flat shape. For example the ratio of the height to the width of the microparticle can be any desired ratio, e.g. can be from 1:1.2 to 1:4 or more, etc.

Figure 3A:
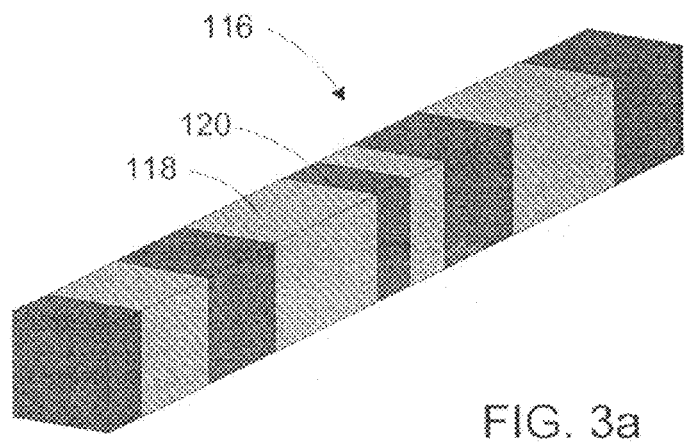
FIG. 3a schematically illustrates another example encoded microparticle of the invention.

FIG. 3a schematically illustrates another example encoded microparticle of the invention. Referring to FIG. 3a, microparticle 116 is composed of a $1^{st}$ material 118 and $2^{nd}$ material 120. The two materials can be chemically different or have the same chemical composition but be different in another respect such as grain structure or thickness. The two materials are distinguishable with the desired detection scheme. In this example each material preferably fully traverses the cross section of the particle. An example process for creating this structure involves fabrication methods as described, including those from the IC/MEMS (Integrated Circuit/Micro-Electro-Mechanical Systems) fields, including variations on the patterning and etching methods disclosed herein below, and/or with high energy ion implantation.

Figure 3B:
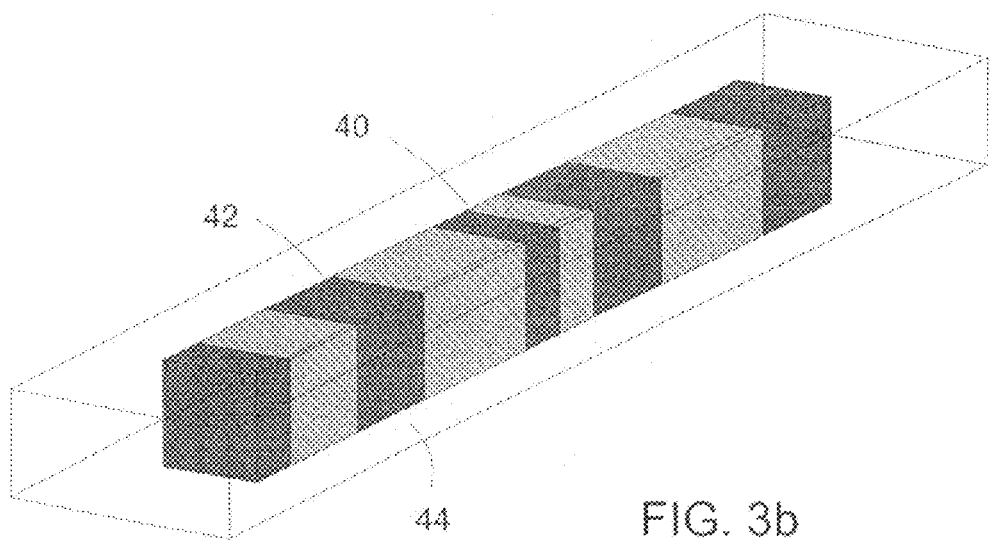
FIG. 3b schematically illustrates an another example encoded microparticle of the invention.

FIG. 3b schematically illustrates an another example encoded microparticle of the invention. Referring to FIG. 3b, the microparticle is comprised of alternating segments of two different materials 40 and 42 that are surrounded by a third material 44, whereby the pattern of alternating segments forms a detectable code. Other example microparticles may contain more than two different materials in the interior of the particle. The particle may have any suitable cross sectional shape and in the example shown, is elongated.

Figure 4A:
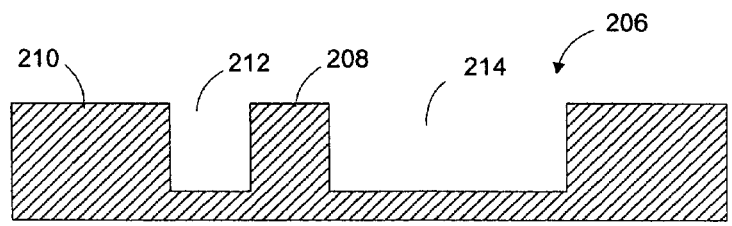
FIG. 4a and FIG. 4b schematically illustrates an exemplary microparticle whose coding structures are derived from a single material.
Figure 4B:
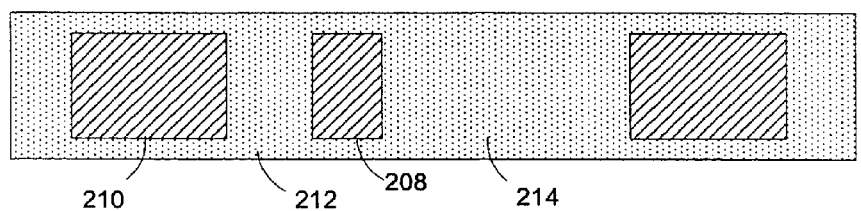

In the examples as discussed above, the microparticle is composed of materials of selected distinguishable properties, such as distinguishable optical properties. In the example above, one material has a greater transparency or optical transmissivity than the other material, which difference is detectable under magnification. A specific example of the above is where one material is a light absorbing material, and the other material is a translucent or transparent material with greater light transmittance in the visible spectrum (or in another spectrum should a different detection system be used—e.g. UV, IR etc). In another example, one material is a light reflecting material whereas the other material is either light absorbing or light transmitting. A detectable difference where one material is more opaque and the other material is less opaque, or where one material is more reflective and the other material is less reflective, are within the scope of this example. As mentioned above, the alternating portions of opaque and transparent materials can be made of silicon and glass among other materials. Given the fact that transmissivity (and reflectivity) of almost all materials exhibit dependencies from the thickness of the material, the microparticle may be formed such that the coding structures (i.e. the structures representing coding elements of a code) are derived from a single material. FIG. 4a and FIG. 4b schematically illustrates an exemplary microparticle whose coding structures are derived from a single material, such as silicon.

Referring to FIG. 4a wherein a cross-sectional view of an exemplary microparticle is illustrated therein. Microparticle 206 comprises a set of coding structures (e.g. 210, 212, 208, and 214), the combination of which represents a code derived from a coding scheme. For incorporating the code, the coding structures have different profiles, such as widths while different structures with different widths are positioned at particular locations. For defining the coding structure and code detection afterwards, a set of gaps (e.g. gaps 212 and 214) with thicknesses less than the transmissivity threshold thickness (the threshold below which the material is visible to the particular light such as visible and near-visible light). Different from the example as shown in FIG. 1a, the coding structures are not fully separated or isolated. The code incorporated in the microparticle can be read based on the different transmissivity of the coding structure (e.g. 210 and 208) which, for example, are less transmissive than the adjacent gaps (e.g. 212 and 214) between the coding structures.

For facilitating the application of the microparticles, especially biological/biochemical/biomedical/biotechnology applications wherein the sample bio-molecules are to be attached to the surfaces of the microparticles, an immobilization layer may be desired to be coated on the surfaces of the microstructures. As such a functionalized surface can be provided. Examples of such functionalized surfaces include, but are not limited to, surfaces derivatized with carboxyl, amino, hydroxyl, sulfhydryl, epoxy, ester, alkene, alkyne, alkyl, aromatic, aldehyde, ketone, sulfate, amide, urethane group(s), or their derivatives thereof.

Figure 4C:
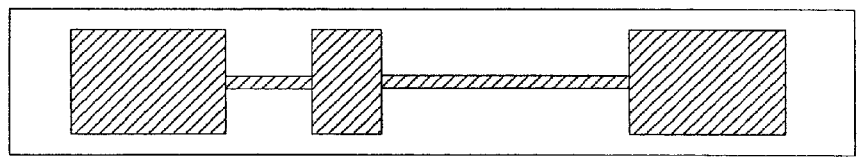
FIG. 4c schematically illustrates an another example encoded microparticle of the invention.

FIG. 4b schematically illustrates a transmissive-mode image of the microparticle in FIG. 4a. Referring to FIG. 4b, dark regions 210, 208 respectively correspond to the coding structures 210 and 208 in FIG. 4a. White regions 212 and 214 respectively correspond to the coding structures 212 and 214 in FIG. 4a. Even though the material used in the more light transmitting and less light transmitting sections is the same, the transmittance profile can still allow for a detectable code. Such a microparticle in FIG. 4a can be formed with a bottom layer of another material (e.g. silicon dioxide), and be coated with a second layer of another material (e.g. silicon dioxide) if desired. Such a microparticle can also be fully encased in a material (e.g. silicon dioxide) such that it has substantially the same rectangular parallel piped shape as the structure in FIG. 1a. FIG. 4c schematically illustrates an another example encoded microparticle of the invention. Referring to FIG. 4c, the microparticle comprises larger regions connected by narrower regions. The microparticle is surrounded by a material such that a code is detectable.

Figure 4D:
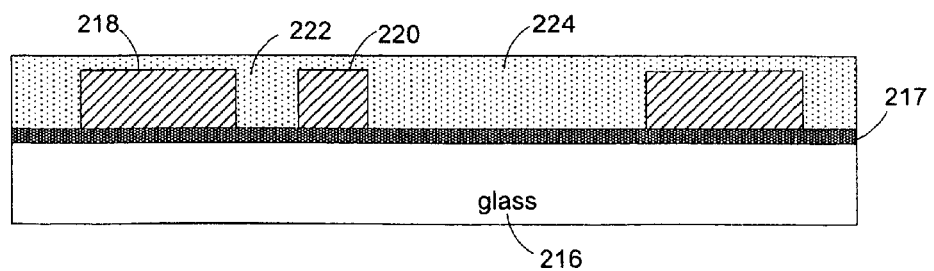
FIG. 4d is a cross-sectional view of another exemplary microparticle during an exemplary fabrication of the invention.

The microparticle of FIG. 4a and FIG. 4c can be fabricated in many ways, one of which is schematically demonstrated in a cross-sectional view of the microparticle during the exemplary fabrication in FIG. 4d. Referring to FIG. 4d, substrate 216 composed of material (e.g. glass, quartz, or other suitable materials) that is transmissive to a particular light (e.g. visible or near-visible light) is provided. Detaching layer 217 is deposited on substrate 216. The detaching layer is provided for detaching the microparticles from the glass substrate afterward by etching or other suitable methods. The etching can be wet, dry, or plasma etching; and the detaching layer is thus desired to be composed of a material etchable with the selected etching method, as discussed hereinabove. As described for previous embodiments of the particle structures, the detaching layer may be omitted such that the particle is formed directly on the substrate and is subsequently released by a bulk etch of the substrate.

A coding structure layer is deposited and patterned so as to form the coding structures, such as structures 218, 222, 220, 224. After forming the coding structures, surrounding layer 224 is deposited on the formed coding structures. Because the surrounding layer will be exposed to the target sample in the assay, it is desired that layer 224 is composed of a material that is resistant to chemical components in the assay solution wherein the microparticles are to be dispensed. Moreover, for holding the probe molecules, such as nucleic acids (e.g. DNA or RNA), proteins, antibodies, enzymes, drugs, receptors, or ligands, molecules on the surface of the layer, layer 224 is desired to be capable of immobilizing the probe molecules.

Fabrication Process

The following exemplary fabrication processes will be discussed in reference to microparticles with segments and gaps, however it should be noted that the following methods are applicable to many other types of code elements.

The microstructure of the invention can be fabricated with a method that fall into the broad field of micro-machining, such as MEMS fabrication methods. MEMS use the techniques of the semiconductor industry to form microscale structures for a wide variety of applications. MEMS techniques typically, but not in all circumstances, include the deposition of thin films, etching using dry and/or wet methods, and lithography for pattern formation. Because MEMS is an offshoot of the semiconductor industry, a vast worldwide manufacturing infrastructure is in place for cost-effective, high volume, precision production. Generally speaking, the more similar the full MEMS process is to existing integrated circuit processes, e.g. CMOS compatible, the more accessible this infrastructure is.

The microstructure of the invention can be fabricated in many ways, such as fabrication methods used for integrated circuits (e.g. interconnects) or MEMS. In the following, an exemplary fabrication method compatible with the MEMS fabrication for making a microparticle will be discussed with reference to FIG. 5 and FIG. 6a to FIG. 6m, wherein the microparticle comprises opaque segments that are composed of amorphous silicon, and visible light transmissive gaps that are comprised of silicon dioxide. It will be appreciated by those skilled in the art that the following fabrication discussion is for demonstration purposes only, and should not be interpreted as a limitation on the scope of the invention. In fact, many fabrication methods could be used without departing from the spirit of the invention.

Figure 5:
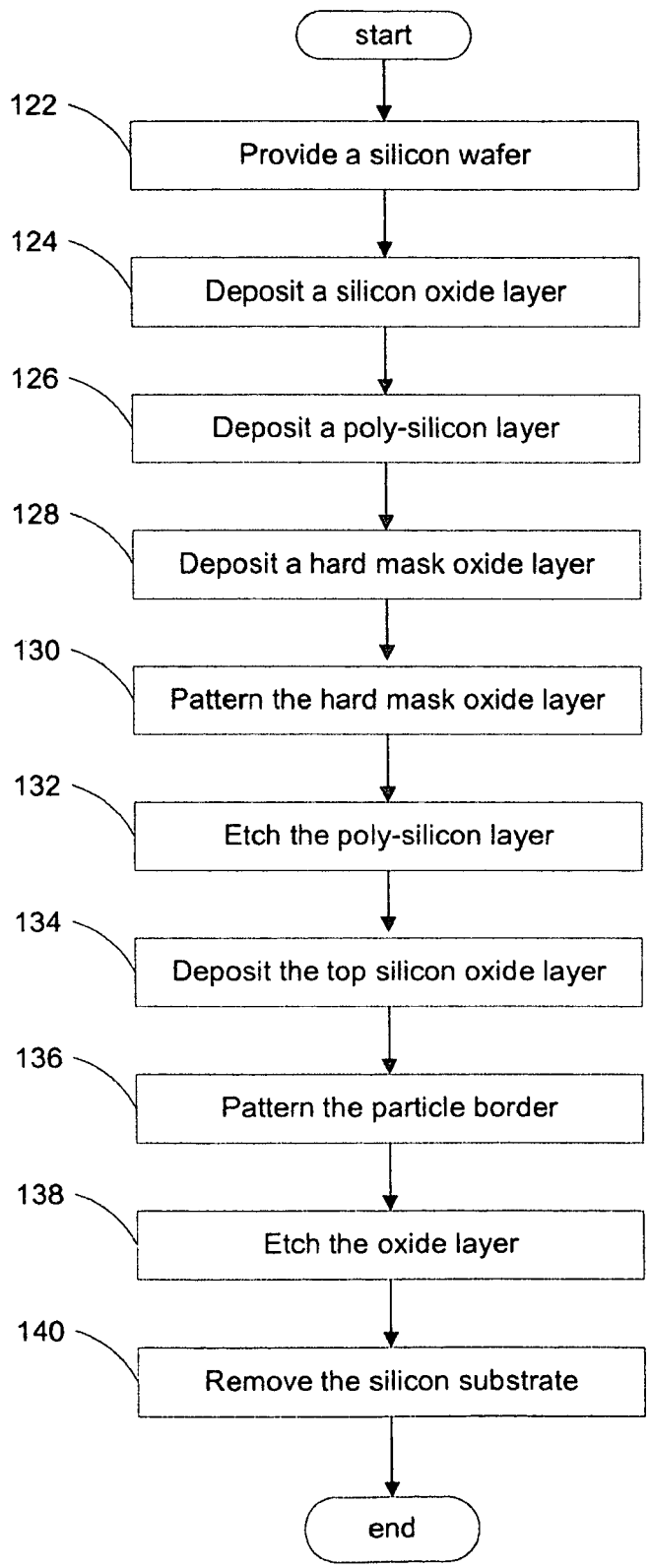
FIG. 5 is a flow chart showing the steps executed in an exemplary fabrication method of the invention.

Referring to FIG. 5, a silicon substrate is provided at step 122. Other substrates, such as glass wafers or glass panels could also be used (as will be discussed further herein below). Assuming a silicon substrate, on the substrate is deposited a silicon dioxide layer at step 124. The deposition can be performed with many suitable thin film deposition techniques, such as CVD, PVD, spin-on etc. as mentioned above. An amorphous silicon layer is then deposited on the $SiO_2$ layer at step 126 followed by deposition of a hard mask oxide layer at step 128. Though not needed the use of a hard mask reduces photoresist coating problems cause by topology, particularly when the amorphous silicon layer is relatively thick (e.g. 1 um or more in thickness). The hard mask oxide layer is then patterned at step 130. With the patterned hard mask layer, the amorphous silicon layer is etched with a plasma etch so as to form the desired pattern at step 132. A top $SiO_2$ layer is then deposited on the patterned silicon layer at step 134 followed by patterning the silicon dioxide layer at step 136 to form separate (but still unreleased) microparticles. Then the microparticles are released from the silicon substrate at step 140 by a non-direction silicon etch that etches into the silicon substrate and causes the microparticles to be separated as individual particles. The flow chart in FIG. 5 as discussed above can be better demonstrated in cross-sectional views and top views of the microparticle at different steps. The cross-sectional and top views are schematically illustrated in FIG. 6a to FIG. 6m.

Figure 6A:
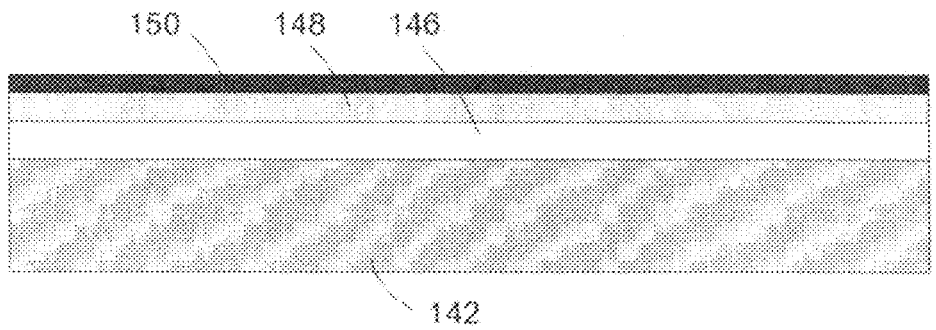
FIG. 6a to FIG. 6m are cross-section views and top views of a microparticle in an exemplary fabrication process of the invention.
Figure 6B:
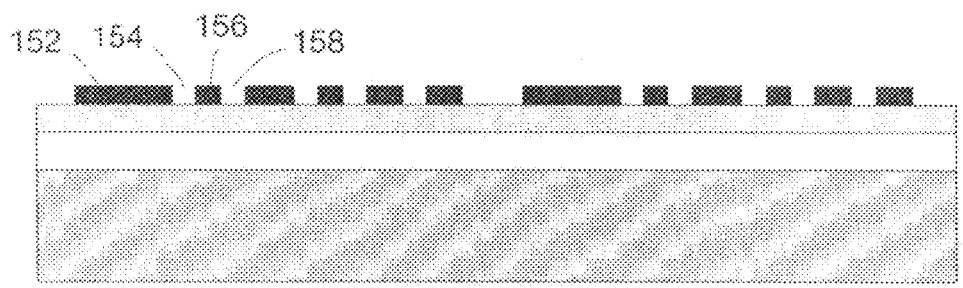
Figure 6C:
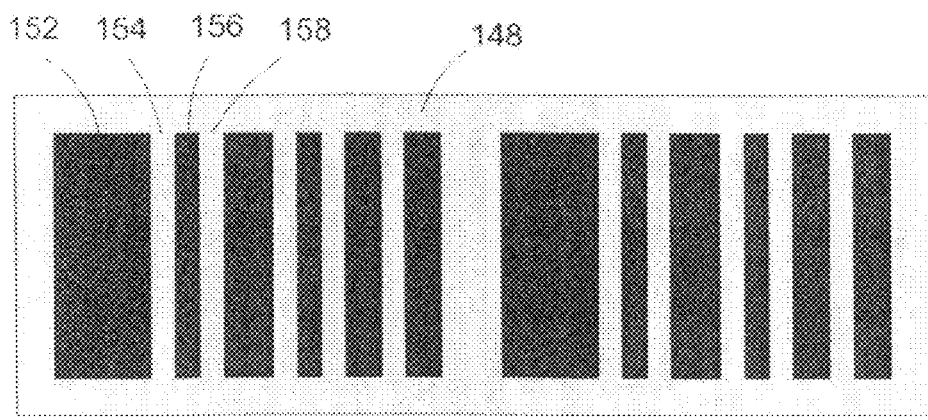

Referring to FIG. 6a, $SiO_2$ layer 146, silicon layer 148, and hard mask layer 150 are sequentially deposited on silicon substrate 142. Hard mask layer 150 is then patterned so as to form segment strips (e.g. 152 and 156) and gap strips (e.g. 154 and 158), as shown in FIG. 6b. The segment and gap strips formed from the patterning of the hard mask layer correspond to the segments and gaps of the target microparticle. The segment and gap strips are better illustrated in a top view of the microparticle in FIG. 6c. Referring to FIG. 6c, segment strips (e.g. 152 and 156) and gap strips (e.g. 154 and 158) are formed with layer 148 that is visible from the top.

The patterning of the layers can be done in many methods, one of which is photolithography that is widely used in standard fabrication for semiconductor integrated circuits and MEMS devices. The most common form of photolithography used in the MEMS industry is contact photolithography. A reticle (aka mask) is typically composed of a binary chrome pattern on a glass plate. The reticle is placed very near or in contact with a photoresist covered wafer (or other substrate). UV light is shone through the mask, exposing the photoresist. The wafer is then developed, removing the photoresist in the exposed regions (for positive-tone photoresist). The pattern on the reticle is thus transferred to the photoresist where it serves as a mask for a subsequent etching step.

Projection photolithography is another type of photolithography that is used exclusively in modern integrated circuit manufacturing. Instead of bringing the mask into physical contact, projection photolithography uses a system of lenses to focus the mask pattern onto the wafer. The primary advantage of this system is the ability to shrink the mask pattern through the projection optics. A typical system has a five times reduction factor. In general, much smaller feature sizes can be printed with projection as compared to contact lithography. A projection photolithography system is also known as a step-and-repeat system (or stepper for short). The maximum pattern or field size on the mask is significantly smaller than the wafer diameter. The mask pattern is repeatedly exposed ("stepped") on the wafer forming an array of "dies". The stepping distance is the distance the wafer stage travels in X and Y between exposures and is usually equal to the die size. This typical scheme produces a non-overlapping array of identical dies, allowing for subsequent parallel processing of the dies on the wafer.

Figure 6D:
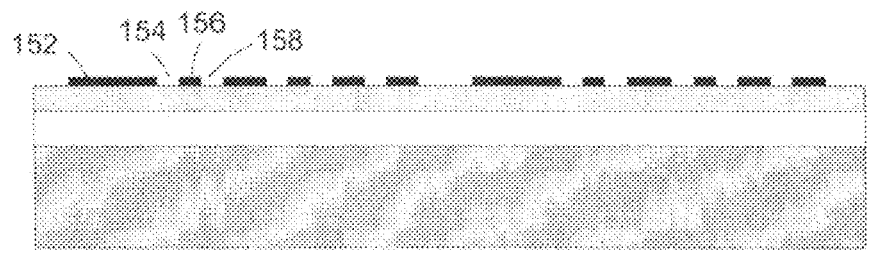
Figure 6E:
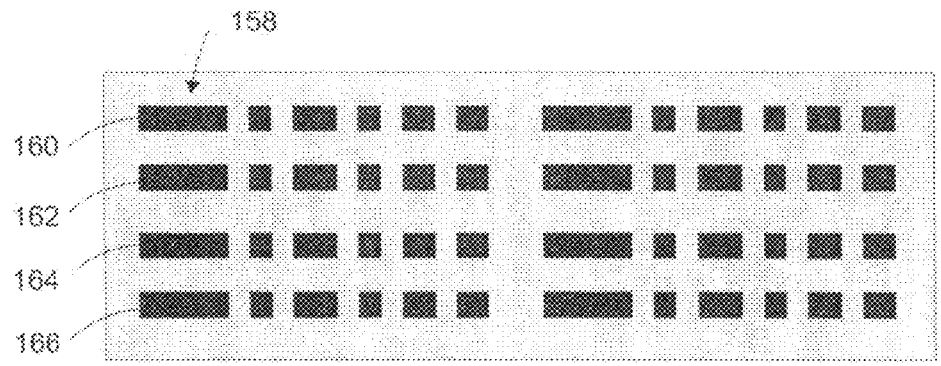

The hard mask layer (150) is further patterned so as to form discrete areas, as shown in FIG. 6d and FIG. 6e. As shown in FIG. 6d, the hard mask layer 150 is patterned in the X and Y directions so as to form discrete hard mask areas (e.g., areas 160, 162, 164, and 166 in FIG. 6e). These discrete hard mask areas will in turn be used to form discrete silicon areas in the layer below.

In the example above, the patterning of the hard mask layer is performed in two separate lithography steps. In an alternative example, the reticle may comprise a pattern such that the patterning of the hard mask can be accomplished with a single lithography step. As a further alternative, the hard mask can be omitted and either a two step or single step lithography process used.

Figure 6F:
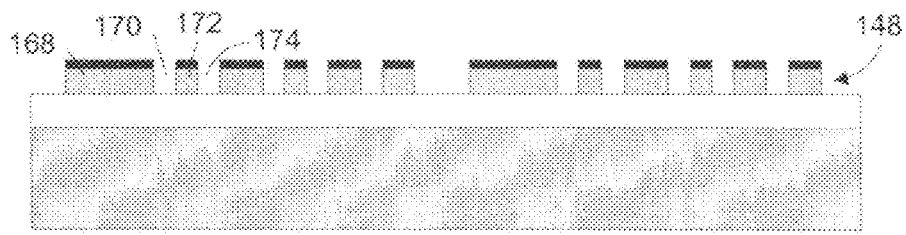
Figure 6G:
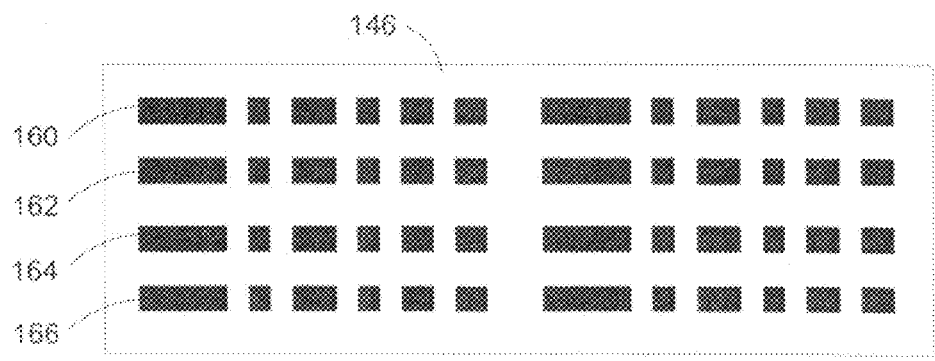

After patterning the top hard mask layer, silicon layer 148 is etched so as to form corresponding discrete silicon areas on the substrate, such as silicon segments 168 and 172, with areas there between for material of greater transparency (e.g. gap areas 170 and 172, as shown in FIG. 6f). The top view of the microparticle as shown in FIG. 6f is schematically illustrated in FIG. 6g. As seen in FIG. 6g, transmissive layer 146 is now exposed when viewed from the top, with segments 160, 162, 164, and 166 formed on transmissive layer 146. SEM images of the structures at this point in the fabrication process are shown in FIG. 8a and FIG. 8b. The structures have a very high degree of precision, e.g. vertical sidewalls and sharp corner. Of course more rounded structures are also in the scope of these methods.

Figure 6H:
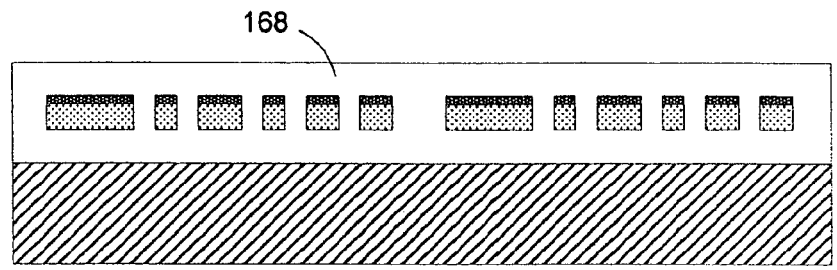
Figure 6I:
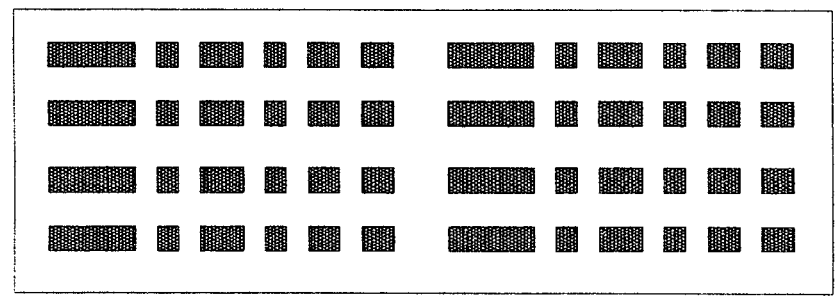

After patterning silicon layer 148, transmissive layer 168 is then deposited as shown in FIG. 6h. The more light transmissive layer 168 may or may not be composed of the same material as the more light transmissive layer 146. A top view of the microparticles in FIG. 6h is schematically illustrated in FIG. 6i. A perspective view of the particles on the substrate is shown in FIG. 7.

Figure 6J:
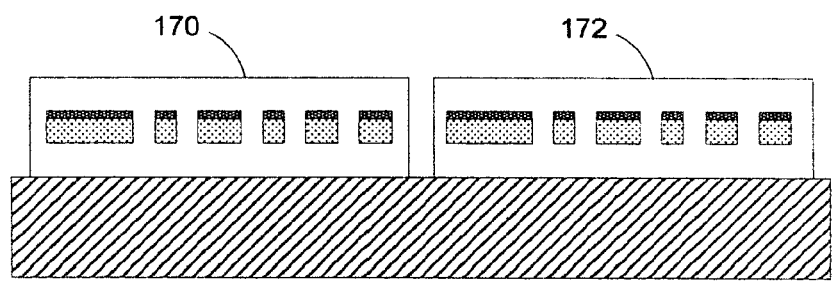
Figure 6K:
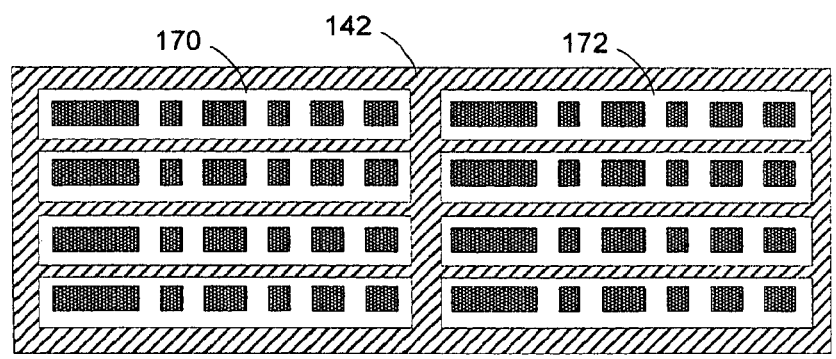
Figure 6L:
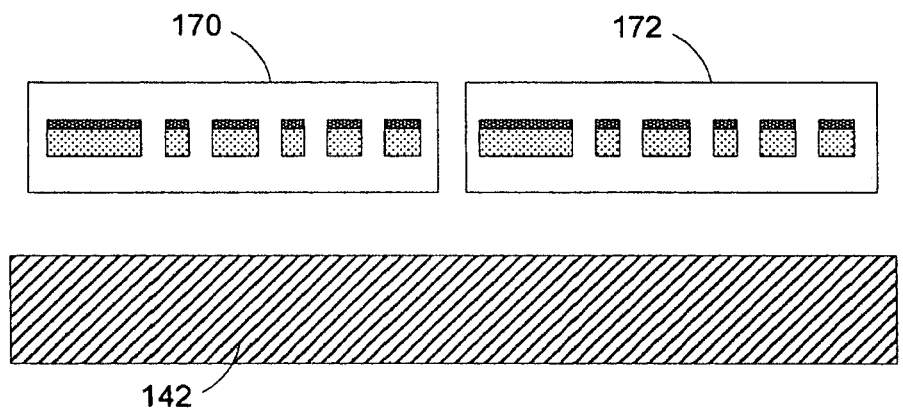
Figure 6M:
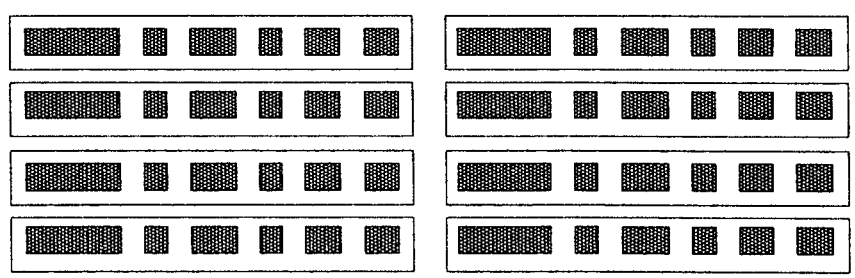

The microparticles are then separated from each other, while still attached to the underlying substrate, as shown in FIG. 6j. FIG. 6k schematically illustrates a top view of the microparticle in FIG. 6j, wherein each microparticle is separated from adjacent microparticles, but surrounded by the light transmissive layer (i.e. layer 168 in FIG. 6h). Finally, the separated microparticles are detached from the silicon substrate 142, as shown in a cross-sectional view in FIG. 6l. A top view of the detached microparticles from the silicon substrate is illustrated in FIG. 6m. The detaching of the microparticles from the underlying substrate (the "release" step) can be performed with any suitable etchant—preferably a gas or liquid matched to etch in all directions and undercut the microparticles. An additional sacrificial layer can be provided on the substrate in place of etching into the substrate itself. The etching can be wet, dry, or plasma etching; and the detaching layer is thus desired to be composed of a material etchable with the selected etching method. In particular, the etchant can be a spontaneous vapor phase chemical etchant such as an interhalogen (e.g. $BrF_3$ or $BrCl_3$), a noble gas halide (e.g. $XeF_2$), or an acidic vapor such as HF. A liquid could also be used to release the microparticles, such as TMAH, KOH (or other hydroxides such as NaOH, CeOH, RbOH, $NH_4OH$, etc.), EDP (ethylene diamine pyrocatechol), amine gallate, —HF etches glass so that won't work HNA (Hydrofluoric acid+Nitric acid+Acetic acid), or any other suitable silicon etchant (when the substrate or layer to be removed in the release is silicon (amorphous silicon or polysilicon or single crystal silicon—or tungsten, tungsten nitride, molybdenum, titanium or other material that can be removed in a silicon etchant such as $XeF_2$). If the material to be removed is not silicon, then the etchant is naturally matched to the sacrificial material (e.g. downstream oxygen plasma for a photoresist or polyimide sacrificial layer, etc.).

The indentations are as a result of the particular fabrication method; and can remain in the final product, or can be removed by, for example, planarization—e.g. chemical-mechanical-polishing (CMP) techniques. In fact, the indentations in some situations can be beneficial for code detection and/or fluorescence quantitation using fluorescent methods because the binding of a fluorescently tagged material to the surface of the microbarcode is greater in the indentation areas (per unit length of the microbarcode), the so called indentation signal enhancement, fluorescence can be greater in the indentation areas and can be used to determine the code (with or without other transmissive or reflective techniques discussed herein below). The same indentation signal enhancement would be applicable with reporter systems other than fluorescence, e.g. radioactive reporters, etc.

Though a silicon wafer was mentioned as the substrate in the example given above, a glass substrate, such as a glass wafer or larger glass sheet or panel (e.g. like those used in the flat panel display industry) could be used. Glass (or silicon) wafers can be of any suitable size—e.g. 4 in., 6 in., 8 in. or 12 in. When a glass wafer is used, typically an additional sacrificial layer will first be deposited (for later removal during the release step). The sacrificial layer can be semiconductor material, such as silicon, an early transition metal, such as titanium, chromium, tungsten, molybdenum, etc. or a polymer, such as photoresist, as mentioned earlier herein.

SEMs

Figure 8C:
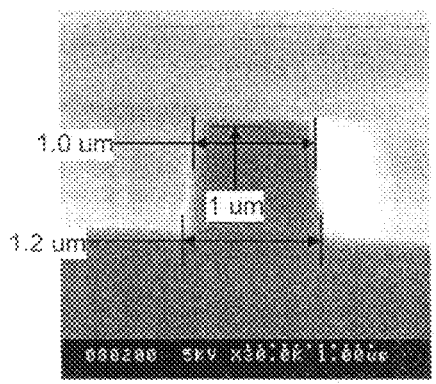
FIG. 8a to FIG. 9 are SEM images of a plurality of microparticles during the fabrication of an exemplary fabrication method of the invention.

A scanning-electron-microscopy (SEM) image of a segment (e.g. segment 102) in FIG. 1a is presented in FIG. 8c. As can be seen in the figure, the cross-section of the segment is substantially square. The top of the segment has a width of 1.0 micron; and the bottom width of the segment has a width of 1.2 microns. The height of the segment is approximately 1 micron. Of course larger or smaller dimensions are possible.

Figure 9:
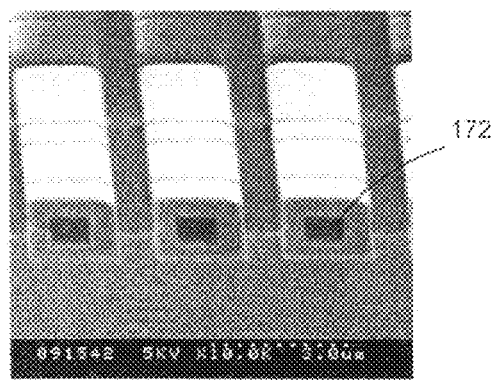

An SEM image of a multiplicity of microparticles fabricated with the exemplary fabrication method as discussed above is presented in FIG. 9. The SEM image clearly illustrates the opaque segment 172 surrounded by transmissive material of the microparticle. Also, the indentations mentioned previously are clearly visible. It is envisioned that the transmissive material can be glass surrounding an opaque segment embedded therein. In one embodiment the glass surrounding the segment is between 0.01 to 2 microns in thickness. In a particular embodiment the glass has a minimum thickness of 0.1 microns. In another embodiment the glass has a minimum thickness of 0.3 microns. The sample in the SEM image of FIG. 9 was prepared for characterization by cleaving a chip perpendicular to the long axis of the particles, followed by a timed silicon etch to provide higher contrast between the inner silicon and outer silicon dioxide, purely for imaging purposes.

Release

The microparticles of the invention can be fabricated at the wafer-level, and released either at the wafer level or die level. Specifically, a plurality of dies each comprising a set of microparticles can be formed on a wafer. The microparticles on each die may or may not be the same—that is the microparticles on each die may or may not have the same code. After forming the microparticles, the dies can be separated from the wafer; and the wafer(s) on the singulated dies can be then removed. An exemplary wafer-level fabrication method is demonstrated in FIG. 12a to FIG. 12c.

Figure 12A:
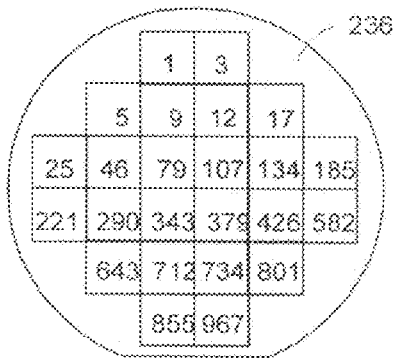
FIG. 12a to FIG. 12c schematically illustrate an exemplary wafer level fabrication method according to an exemplary fabrication method of the invention.

Referring to FIG. 12a, a plurality of dies is formed on wafer 236. In this particular example, multiple microparticles are formed on each die. The number, such as 3, 221, or 967 on each die represents the code incorporated in the microparticles in the die. The microparticles can be formed with a method as discussed above with reference to FIG. 6a to FIG. 6m. After formation of the microparticles but prior to release, the wafer can be partially cut, preferably to a depth about half the wafer thickness. The wafer is then cleaned, for example with solvents and/or a strong acid (sulfuric, hydrogen peroxide combination). The clean is an important step as it prepares a fresh glass surface for later functionalization and biomolecule attachment. The clean can also be performed after the wafer is separated into individual dies, or on the particles once they have been released.

Figures 12B, 12C:
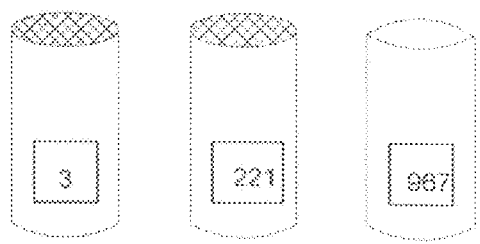

After the formation of the microparticles, the wafer is then broken into dies as shown in FIG. 12b, where each die preferably, but not necessarily, contains a single code. The dies are then placed in separate vessels such as test tubes or the wells of a well plate for release, shown in FIG. 12c. The well plate can be a typical 96-well plate (or 24-well, 384-well, etc.), or any other suitable set of holding areas or containers. For example, dies containing the numerically represented codes: 3, 221, and 967, are placed in different tubes for release. By releasing, the microparticles are detached from the wafer; and the particles can fall into the solution in the releasing liquid when a wet etch is used. The microparticles over time settle to the bottom of the tube or well due to gravity (or the tubes can be centrifuged). In some applications, it may be desirable to release multiple dies comprising one or more codes into a single container.

Figures 11A, 11B:
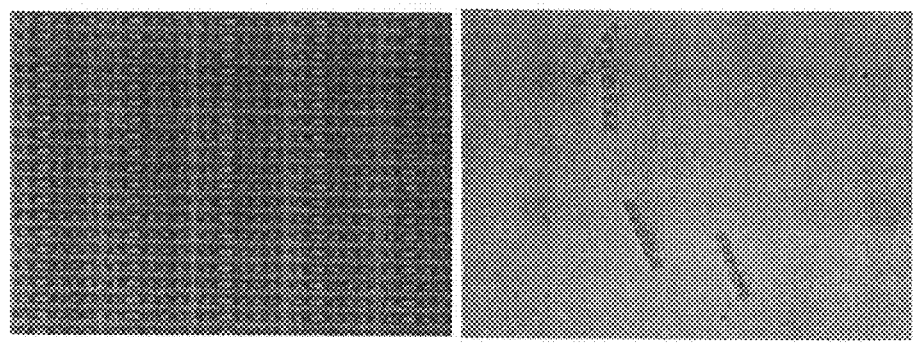
FIG. 11a and FIG. 11b are images of a plurality of microparticles of the invention.

FIG. 11a shows particles before release, and FIG. 11b shows the same particles (i.e. particles from the same die) after release. Both images are optical microscope images taken with a 100× air objective on a non-inverted inspection microscope. In FIG. 11b the particles are dried on a silicon chip.

Figure 10A:
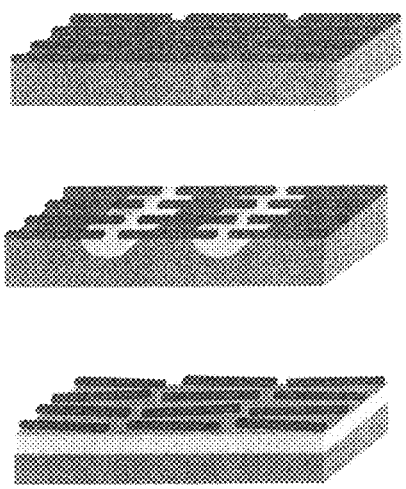
FIG. 10a and FIG. 10b illustrate an exemplary etching method that can be used in the fabrication method of the invention.
Figure 10B:
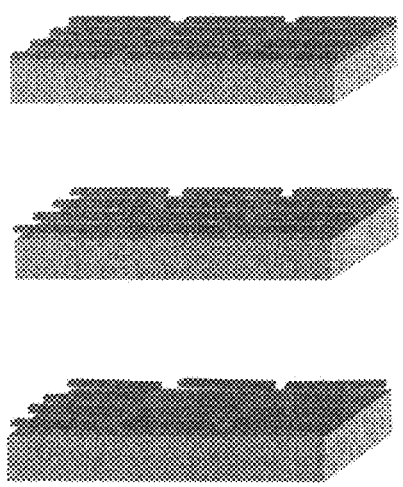

The releasing step can be performed in many ways, such as dry etch, wet etch, and downstream plasma etch. In an exemplary bulk wet etch, shown schematically in FIG. 10a tetramethyl ammonium hydroxide (TMAH) is used as the etching agent. TMAH can be heated to a temperature approximately from 70-80 C. Other chemical etchants can also be used and may work equally well, such as interhalogen (e.g. $BrF_3$ and $ClF_3$) and noble gas halide (e.g. $XeF_2$), HF in spontaneous vapor phase etch, potassium hydroxide in a gas phase etch, KOH, and other suitable etchants. A screen having characteristic apertures (or filter membrane with pores) less than the smallest microparticle dimension can be placed on the top of each well or container, whether liquid or gas release is used, to keep the codes safely within each container and avoid contamination of microparticles into adjacent wells. During the etching, especially the gas phase etch or dry etch, a mesh can be attached to each tube, whether on one end of the tube, well or container, or multiple mesh covering on more than one side of a tube, well or container, such that gas etchant and etching products can flow freely through the mesh while the microparticles are stopped by the mesh. A mesh or other filter can help to drain the liquid release etchant as well, without releasing the microparticles. Another example of a release etch process is shown in FIG. 10b and involves the deposition or formation of a sacrificial layer, as has been previously described.

After pelleting the particles through centrifugation or lapse of time, the liquid (so called supernatant) is removed and the particles are washed several times in water or a solvent. "Washing" refers to the successive replacement of the supernatant with a new liquid, usually one involved in the next chemical processing step. After detaching the microparticles from the substrate (or wafer), the substrate can be removed from etchant—leaving the microparticles in tubes. The released microparticles can then be transferred to containers for use.

The microparticles can be fabricated on the wafer level, as shown in FIG. 12a to FIG. 12c. Referring to FIG. 12a, wafer 236, which is a substrate as discussed above with reference to step 122 in FIG. 2, comprises a plurality of dies, such as dies 1 and 3. In an example of the invention, the wafer has 10 or more, 24 or more, 30 or more, or 50 or more dies. Each die comprises a number of microparticles of the invention, wherein the number can be 10000 or more, 20000 or more, or 50000 or more. The microparticles in the same die are preferably the same (though not required); and the microparticles in different dies are preferably different (again, not required) so as to represent different codes. In the instance when different dies comprise microparticles of different codes, the dies are preferably assigned with unique identification numbers, as shown in the figure so as to distinguish the dies and codes in dies.

Detection

Figure 13:
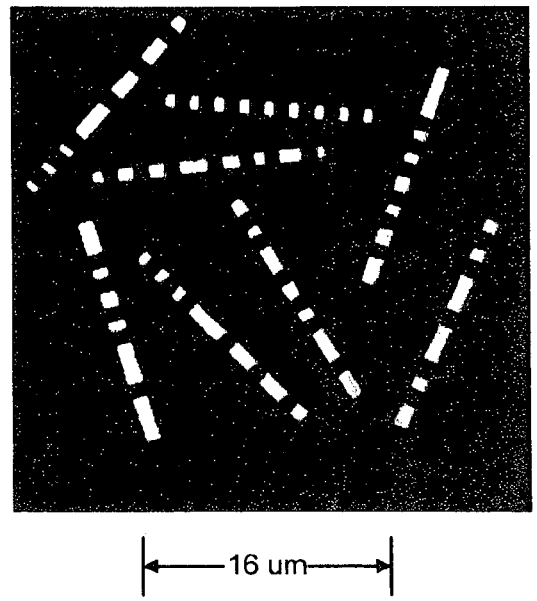
FIG. 13 presents a reflectance-mode inverted microscope image of 8 encoded microparticles of the present inventions.

FIG. 13 presents a reflectance-mode inverted microscope image of 8 encoded microparticles of the present inventions. All such black and white microscope images with a black background are taken on an inverted epi-fluorescence microscope with the released particles in the well of a well plate. The particles are dispensed into the well in a liquid and settle by gravity onto the bottom surface where they are imaged from below. Each particle in FIG. 13 has a different code. Segments of the less transparent material (e.g. opaque material in the visible spectrum), in this case amorphous silicon, reflect light and are the brighter regions in the image. The surrounding transparent material, in this case silicon dioxide, is not visible in the reflectance-mode images. The particles are 16 um long by 2 um wide and approximately square in cross section. The image is a combination of selections from 8 images, one for each code. The illumination light is at 436 nm, and the objective used is a 60× magnification oil immersion lens.

Figure 15:
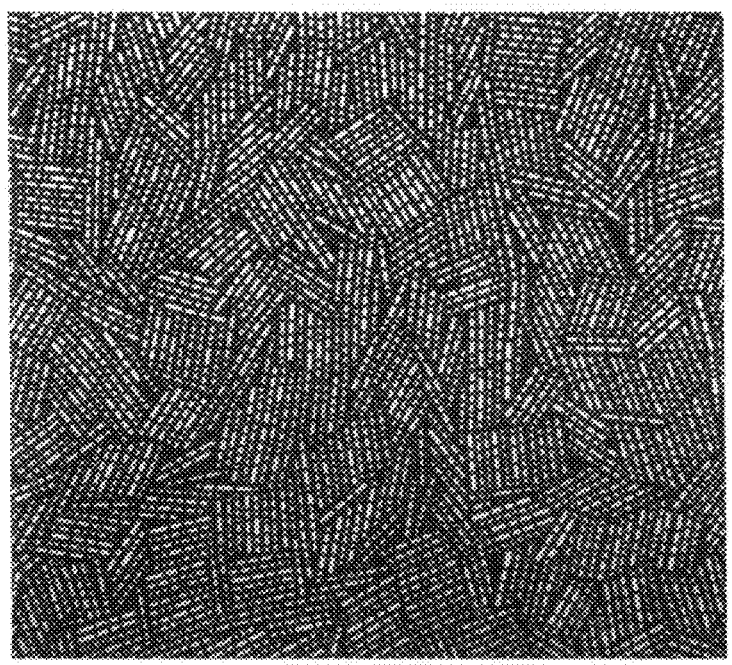
FIG. 15 presents a full field, single image taken at the same magnification as that in FIG. 13.
Figure 16:
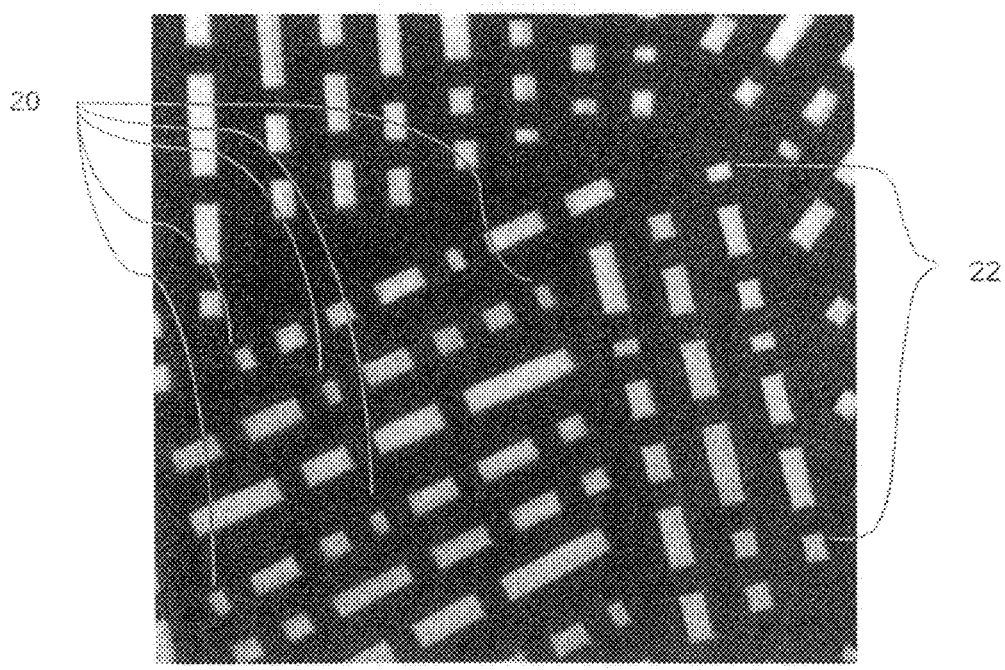
FIG. 16 shows a high magnification image of encoded microparticles.

FIG. 15 presents a full field, single image of a mixture of many different codes. All particles form a high density monolayer—that is, there is no particle aggregation or clumping. The characteristic of the monolayer formation is one of the key advantages of the microparticles of the invention. When the microparticles are overlapped, aggregated, or clumped, the microparticles can not be properly identified. As a consequence, microparticles that do not readily form monolayers as herein, are forced to be used at relatively low densities (the total microparticles per unit area on the imaging surface). Low density imaging translates to correspondingly low throughput for the number of particles measured per unit time. This low throughput can be a limitation in many applications The tendency of the microparticles to form a monolayer is not trivial. Monolayer formation involves many factors, such as the surface charge state (or zeta potential) of the microparticles, the density of microparticles in a specific solution, the fluid in which microparticles are contained, and the surface onto which the microparticles are disposed. Accordingly, the microparticles of the invention are comprised of materials and are constructed in a form that favors the maintenance of a charged state sufficient to substantially overcome stiction forces; and thus microparticles are capable of undergoing Brownian motion which facilitates the formation of a reasonably dense monolayer of particles.

In biological applications, the microparticles are often used to carry biochemical probe molecules. For immobilizing such probe molecules, the microstructure preferably comprises a surface layer, such as a silicon dioxide layer, which can be chemically modified to attach to the probe molecules. In accordance with an example of the invention, the microparticles are constructed such that the microparticles are capable of forming a monolayer, for example, at the bottom of a well containing a liquid; and the monolayer comprises 500 or more particles per square millimeter, more preferably 1,000 or more, 2,000 or more, or 3,000 or more microparticles per square millimeter. In an alternative example, the microparticles can form a monolayer that such that the detectable particles occupy 30% or more, 50% or more, or 70% or more of the total image area (i.e. the image field of view). In connection with the example mechanism of self-assembled monolayer formation, it is preferred that the 2D diffusion coefficient of the microparticles of the invention is greater than $1 \times 10^{-12}$ cm$^2$/s. For accommodating the monolayer of the microparticles, the container for holding the microparticles in detection preferably has a substantially flat bottom portion.

In one embodiment a plurality of microparticles are arranged on a portion of a surface in a monolayer. It is envisioned that the microparticles in the monolayer can cover more than 30% or more, 50% or more, or 70% or more by area of a portion of a surface. In a particular embodiment the portion of the surface covered includes an area greater than 1000 μm. In another embodiment the portion of the surface covered includes an area greater than 1 mm$^2$. In yet another embodiment the portion of the surface covered includes an area greater than 10 mm$^2$. In a particular embodiment the portion of the surface covered is a potion of the bottom surface of a microtiter plate well (a.k.a. a reservoir) filled with a liquid.

Figure 14:
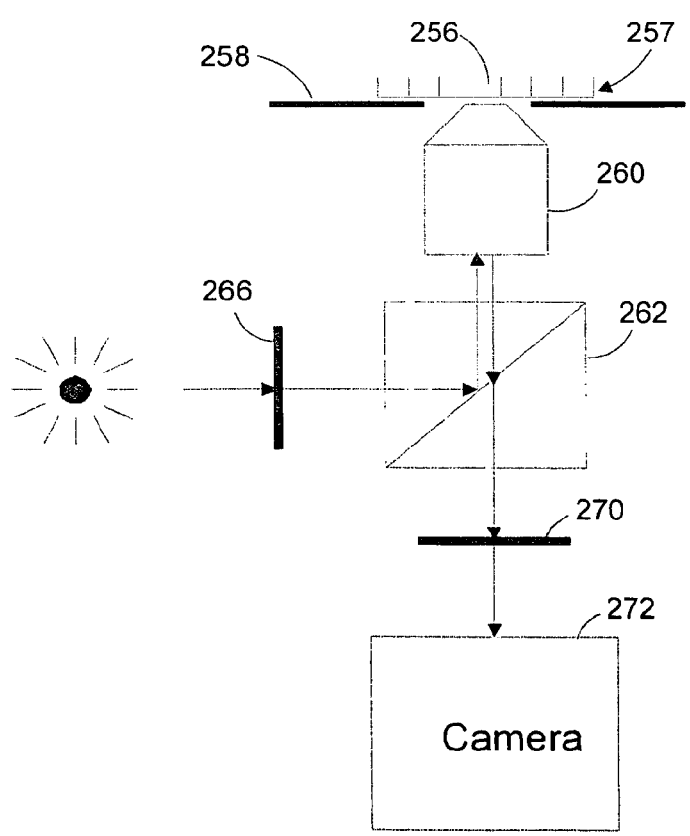
FIG. 14 shows a diagram of an optical system used to image the encoded microparticles of the invention.

FIG. 14 shows a diagram of an optical system used to image the encoded microparticles of the invention. The optical system 254 can be used to read the microparticle codes, including for bioassay applications. The system is an inverted epi-fluorescence microscope configuration. Other exemplary optical microscopy systems for the detection of the microparticles of the invention include but are not limited to confocal microscope systems, Total Internal Reflection Fluorescent (TIRF), etc. Well plate 257 contains many wells of which a single well 256 is imaged. The well plate sits on microscope stage 258. Microparticles that have been dispensed into well 256 in a liquid settle by gravity to the bottom surface. Light coming from light source 268 passes through excitation filter 266 which selects the illuminating wavelength. The illuminating light reflects off beam-splitter 262 and travels up through objective 260. Typically, only a fraction of well 256 bottom surface area is imaged. The imaged area is referred to as the "field" or "field area". Reflected or emitted light (know together as collection light) travels back down the objective and passes through the beam-splitter 262. Emission filter 270 selects for the collection wavelength. Finally the collected light is recorded with a detector 272, such as a CCD camera. This simplified version of the optical system is not meant to be complete. In practice, the actual microscope may have many more features, preferably including an automated stage and auto focus system for high throughput imaging. The excitation filter and emission filter can be mounted on computer controlled filter wheels and are automatically changed for the reflectance and fluorescence images. A computer controlled shutter controls the exposure times.

Figure 42:
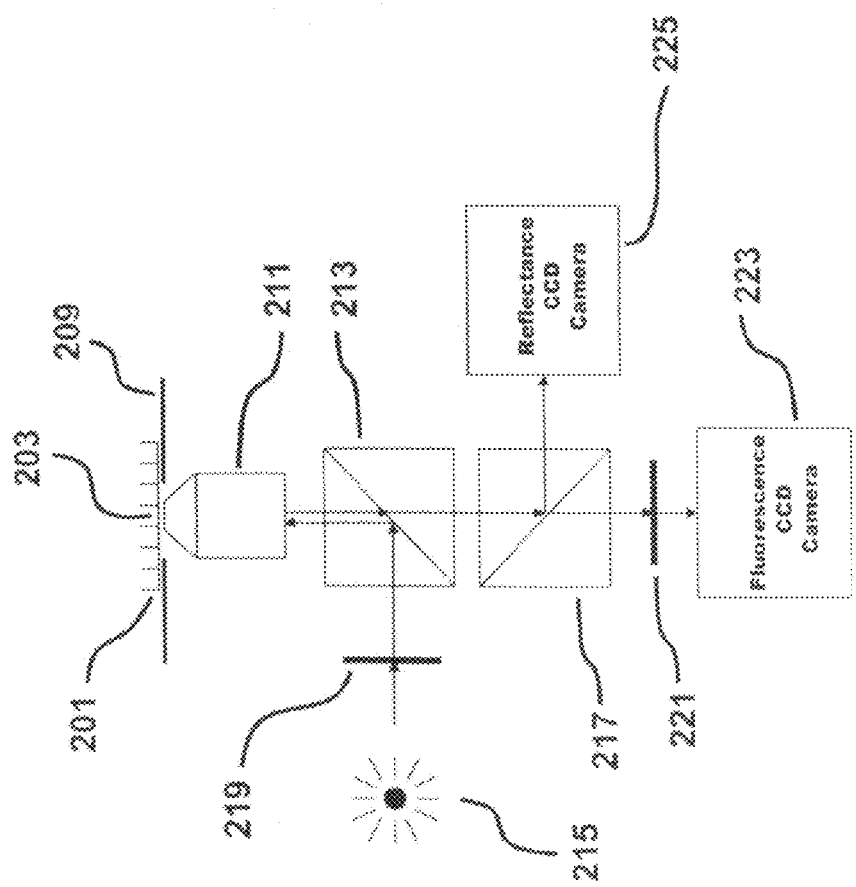
FIG. 42 shows a diagram of an optical system used to image encoded microparticles that utilizes two CCD cameras for the simultaneous acquisition of a reflectance and fluorescence image.

FIG. 42 shows a diagram of an optical system used to image encoded microparticles that utilizes two CCD cameras for the simultaneous acquisition of a reflectance and fluorescence image. The optical system is used for detection in bioassays. The system is an inverted epi-fluorescence microscope configuration. In the preferred embodiment, a wellplate 201 contains many wells of which a single well 203 is imaged. The wellplate 201 sits on the microscope stage 209. Particles that have been dispensed into the well 203 in a fluid settle by gravity to the bottom surface. Light coming from the light source 215 goes through the excitation filter 219 which selects the illuminating wavelength. The illuminating light reflects off the beam splitter 213 and travels up through the objective 211. Typically, only a fraction of the well 203 bottom surface area is imaged. The imaged area is referred to as the "field" or "field area". Reflected or emitted light (know together as the collection light) travels back down the objective and passes through the first beam splitter 213. The collection light then passes through the second beam splitter 217 which breaks it into the reflectance path and the fluorescence path. The emission filter 221 is located in the fluorescence path and selects for the appropriate fluorescence emission wavelength. The light in the fluorescence path is recorded with the fluorescence CCD camera 223. The light in the reflectance path is recorded with the reflectance CCD camera 225. This simplified version of the optical system is not meant to be complete. In practice, the actual microscope system may have more features, preferably including an automated stage and auto focus system for high throughput imaging. The excitation filter 219 and emission filter 221 may be mounted on computer controlled filter wheels to be automatically changed for multi-fluorophore experiments. A computer controlled shutter may be used to control the exposure times.

The system depicted in FIG. 42 is an improvement over the standard one camera system that utilizes filter wheels (or filter cube wheels) to acquire reflectance and fluorescence images in succession. The invention is accomplished by splitting the outgoing beam path into two components with a beam splitter. One component is the reflectance path, which is captured with one CCD camera. The other component is the fluorescence path, which is filtered for the appropriate wavelength and captured with a second matched CCD camera. The beam splitter can be designed such that more light is directed into the fluorescence path such that the exposure times on the two cameras are approximately equal. The two camera system invention offers the advantage of increased throughput. Additionally, the invention offers the advantage of eliminating the positional shifts between reflectance and fluorescence images pairs that may be present in those of the one camera system. This simplifies the computer software based processing of image pairs because the particles are in the same physical locations in both images of the image pair. In a further embodiment, the optical system is used for detection in bioassays.

FIG. 17 shows a high magnification image of encoded microparticles. The imaged particles consist of discrete segments of varying sizes. The smallest size segments 20 are 0.6 um. End segments 22 form the end of a single particle. An exemplary example of the invention consists of encoded microparticles with spatial encoding features less than 1.5 um in size.

Figure 17A:
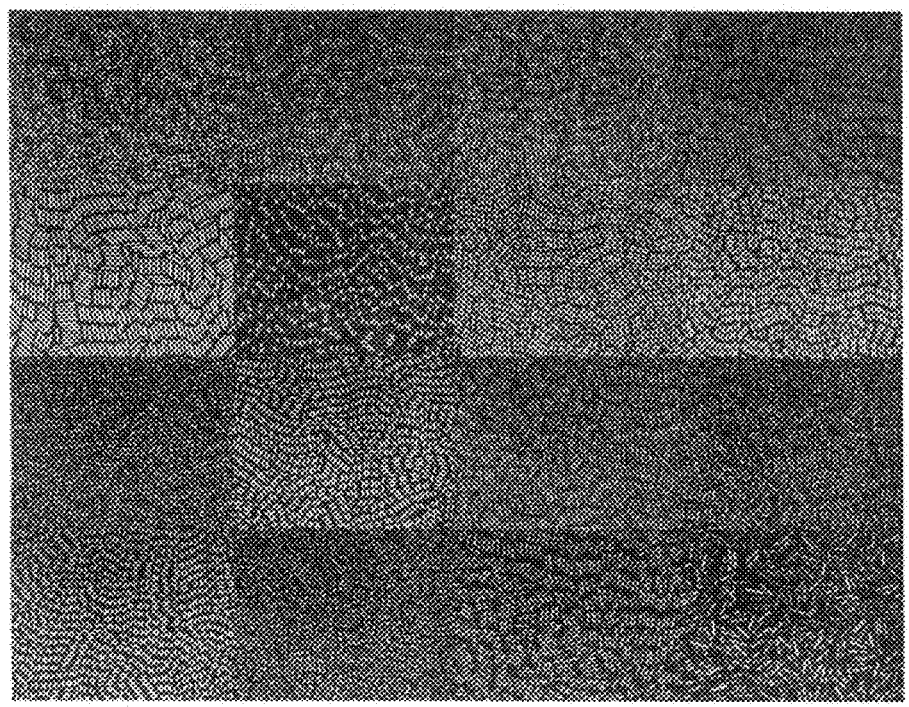
FIG. 17a shows a montage of 16 dense reflectance images of encoded microparticles.

FIG. 17a shows a montage of 16 dense reflectance images of encoded microparticles. Approximately 6,000 particles are in the images. The particles are a small fraction of the approximately 200,000 particles total in a well of a 384 wellplate. The total particles are approximately 10% of a set that contains 1035 codes (batches). The set was formed by combining approximately 2,000 particles from each of the 1035 batches where each batch contained approximately 2 million particles of a single code. These images are a subset of a larger image set from which data regarding identification accuracy is presented below.

Figure 17B:
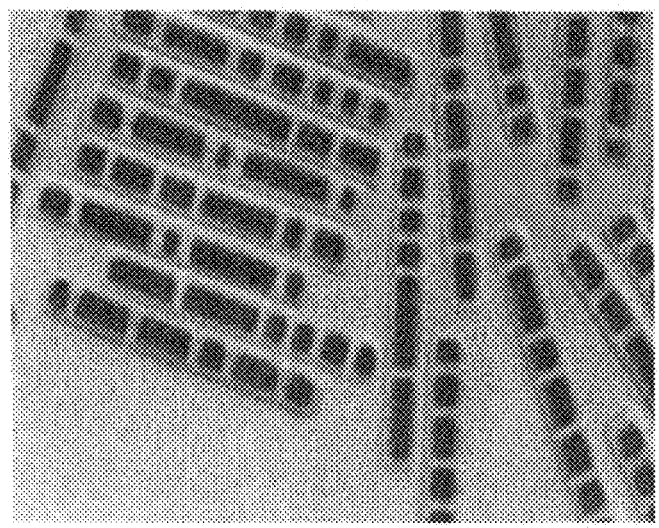
FIG. 17b shows a transmission fluorescence microscope image of example microparticles of the invention.

FIG. 17b shows a transmission fluorescence microscope image of example microparticles of the invention. Shown are here, in addition, small, elongated, encoded microparticles with an outer surface that is entirely glass. Shown are a multiplicity of non-spherical encoded particles with a silica (e.g. glass or silicon dioxide) outer surface and a length less than 70 um (e.g. less than 50 um.). The length of the example particles in this particular example is 15 um.

In this image, the particles are in a solution that contains suspended fluorescent molecules. The fluorescent molecules, when excited by the microscope light source, provide illumination from above (i.e. behind with respect to the collection optics, see FIG. 14 for a diagram of the basic optical system) the particles. This image is similar to one that would be provided in transmission mode imaging configuration, and unlike the reflectance mode images of FIG. 15 to FIG. 17a, clearly shown the outer glass surface of the particles.

For successfully identifying the microparticles, e.g. reading the codes incorporated therein, the images of the microparticles may be processed. Such image processing can be performed with the aid of software programs. According to exemplary examples of software programs and algorithms, pairs of raw and processed image are presented in FIG. 18a and FIG. 18b and in FIGS. 19a and 19b.

Figures 18A, 18B:
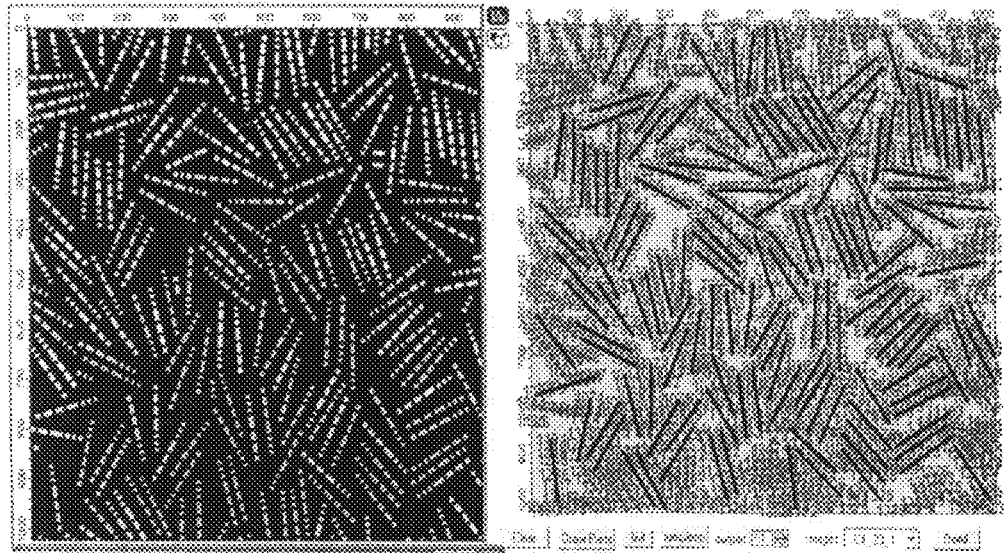
FIG. 18a shows a full field reflectance image.
FIG. 18b shows the same image selection of FIG. 18a after the image processing to associate discrete segments into full microparticles.

FIG. 18a shows a full field reflectance image; and FIG. 18b shows the same image selection of FIG. 18a after the image processing to associate discrete segments into full microparticles. The particles shown in the images are of a single code.

Images of encoded microparticles of the present invention consist of discrete segments that appear white in the reflectance imaging. The gaps, which are between segments of individual microparticles consist of glass, are transparent, and therefore appear black in the reflectance image. The background of the images is also black. The segments are associated together into the particles by an algorithm. The algorithm finds the long axis of a long segment and searches along that axis for segments. Segments are accepted or rejected based on predefined parameters. The black lines in FIG. 18b correspond to particles for which segments have been associated together. In an exemplary example of the aforementioned algorithm, a computer program product that identifies the codes of encoded particles by associating discrete regions in an image into individual particles.

Figures 19A, 19B:
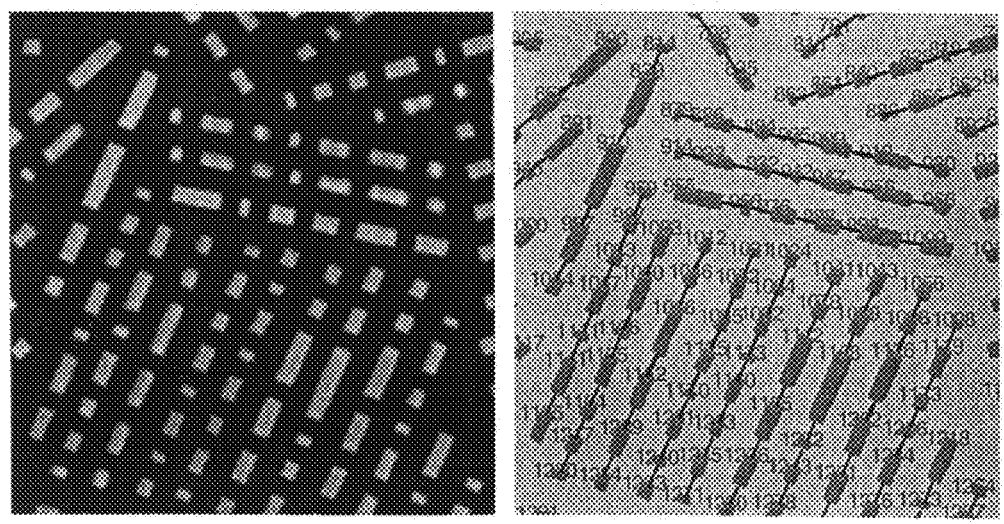
FIG. 19a shows a selection of a reflectance image.
FIG. 19b shows the same image selection of FIG. 19a after the image processing to associate discrete segments into full microparticles.

FIG. 19a shows a selection of a reflectance image; and FIG. 19b shows the same image selection of FIG. 19a after the image processing to associate discrete segments into full microparticles. The particles shown in the images are of a multiplicity of codes. The segments of the particles are numbered. The black lines in FIG. 19b are drawn to illustrate the segments that have been grouped together into particles by the image processing software.

Figure 20:
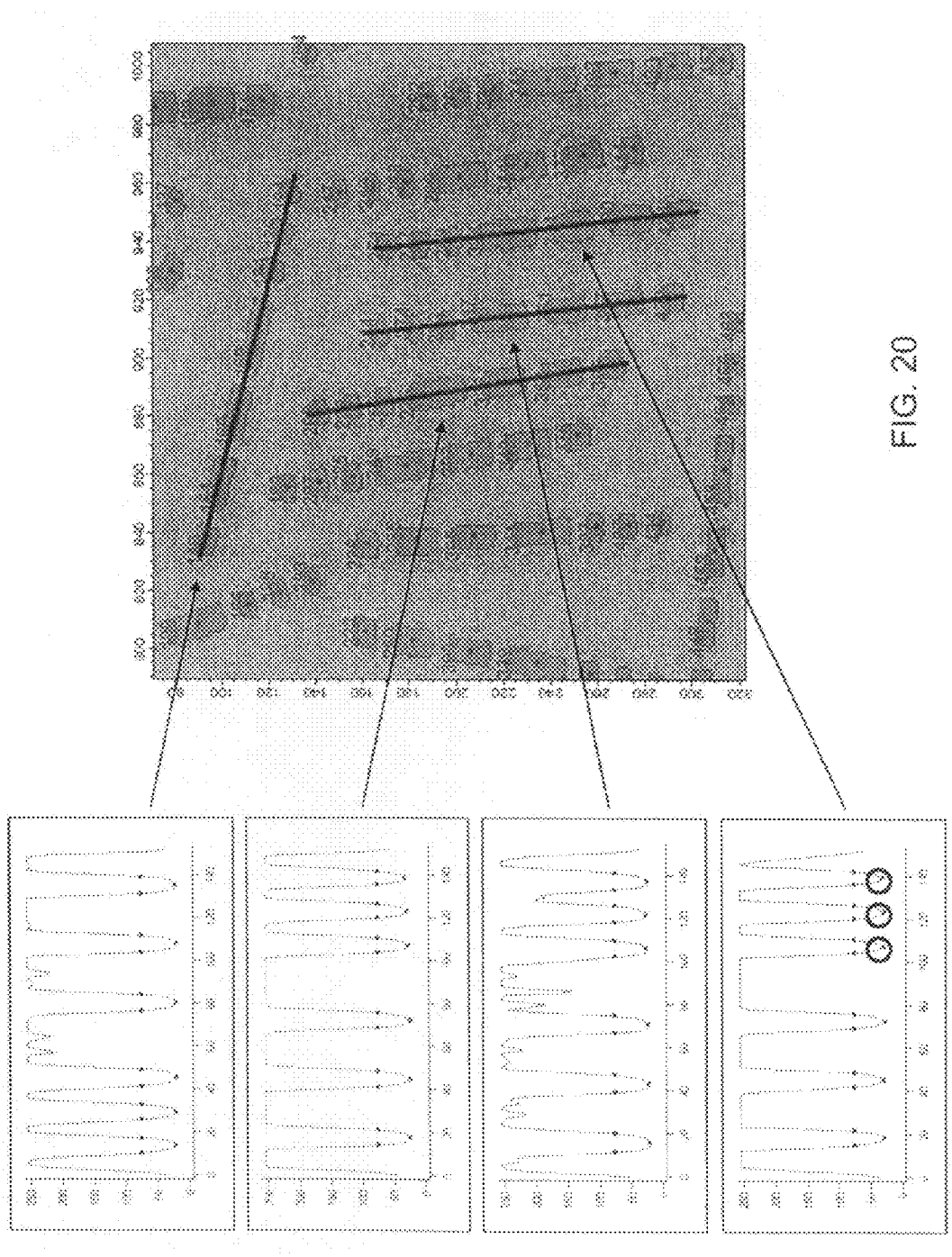
FIG. 20 illustrates a processed image is shown on the right and pixel intensity profiles from 4 example microparticles are shown on the left.

Referring to FIG. 20, a processed image is shown on the right and pixel intensity profiles from 4 example microparticles are shown on the left. The pixel intensity profiles are further processed by a computer software program to determine the codes of the microparticles. By identifying the center locations of the gaps, as indicated by circles in the pixel intensity profile in the lower left, the codes of the microparticles can be identified. As mentioned previously, the center gap locations are not sensitive to variations in both the particle fabrication process or image processing, i.e. variations in the dimensions of the actual segments and gaps that make up the exemplary example structure of FIG. 1a. This feature is highly advantageous as it provides robust and accurate code identification of the encoded microparticles.

Table 1 shows identification data for image sets that include those images shown in FIG. 17a.

TABLE 1

| Images | Full ID %<br>30,069<br>Codes | Limited<br>ID %<br>1,035 Codes |
|---|---|---|
| 40x objective<br>~500 particles/image<br>9866 particles<br>measured | 99.5% | 99.98% |
| 60x objective<br>~250 particles/image<br>2733 particles<br>measured | 99.85% | 99.995% |

The microparticles included in Table 1 have a codespace of 30,069, wherein the codespace is defined as the total number of possible codes with the particular particle design, i.e. with the chosen coding scheme and coding scheme parameters. A pre-determined identification method assigns one of the 30,069 possible codes based on the analysis of the particle segment information. 1035 codes were randomly selected, manufactured, and mixed to form the collection. When analyzing the identification of the collection, if the software assigned code is one of the 1035, it is assumed to be correct. The number of "correctly" identified particles divided by the total is called the "ID %". This assumption underestimates the error rate (1—ID %) by the probability that a random error falls within the 1035 present codes, or 1035 divided by 30,069=about 3%. The assumption therefore ignores this 3% deviation and provides a close approximation to the true identification accuracy.

Figure 21:
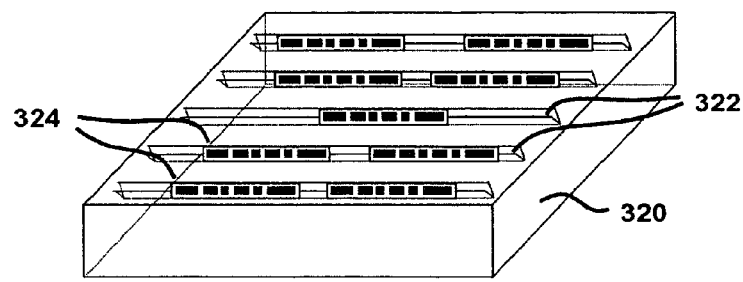
FIG. 21 shows a schematic of a specially prepared surface that have features designed to immobilize and separate the encoded microparticles for imaging.

FIG. 21 shows a schematic of a specially prepared surface that have features designed to immobilize and separate the encoded microparticles for imaging. The surface includes features, e.g. grooves and/or pits that trap the particles. Such surfaces could be useful in applications where the particles experience increased aggregation due to the nature of molecules coated on the surface or properties of the imaging medium. FIG. 21 shows an example of such a substrate 320 with grooves 322 designed to capture the particles. The substrate 320 is preferred to be glass, but may be other materials, for example other transparent materials. The grooves 322 shown in FIG. 21 have a V-shape but may take on any shape such as having a square or U-shaped bottom that accomplishes the task of capturing the particles. When particles are placed onto the surface, particles 324 fall into the grooves and are immobilized. In an exemplary example, encoded microparticles of the present invention, having an elongated and substantially square cross section, may be immobilized in grooves having a flat bottom.

Figure 22:
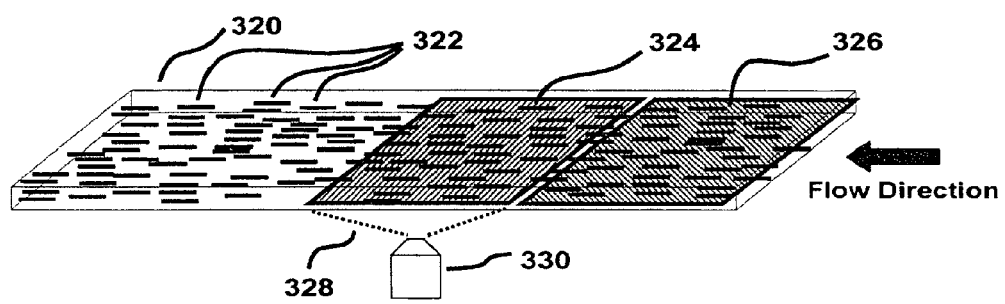
FIG. 22 and FIG. 23 show a flow-cell enabling the microparticles flowing in a fluid can be provided for detection by continuous imaging.
Figure 23:
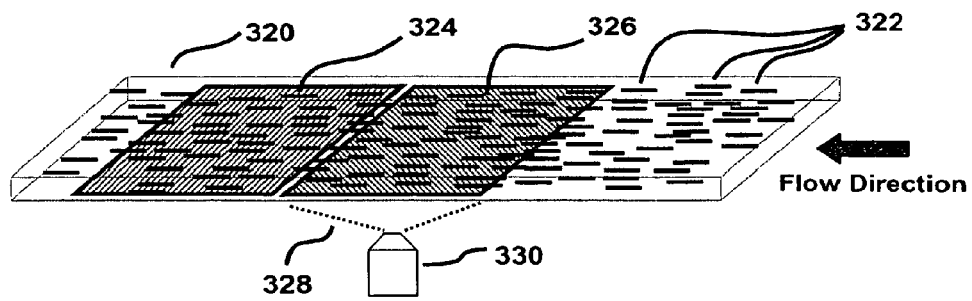

In an alternate example, a flow-cell enabling the microparticles flowing in a fluid can be provided for detection by continuous imaging, as shown in FIG. 22 and FIG. 23. Referring to FIG. 22, reflectance and fluorescence image pairs are acquired with the optical system depicted in FIG. 6 while the well plate is replaced with flowcell 320. Encoded microparticles 322 flow in a carrier fluid. Flow may be driven by pressure (hydrodynamic) or electrical means (electrophoretic or electro-osmotic). Further, microparticles may be aligned with electric or magnetic fields. The flow is from the left to the right as indicated by the arrow. The upper figure of FIG. 22 shows the flow cell at a given time and the lower figure of FIG. 23 shows the same flow cell at a subsequent time such that the particles have displaced a distance equal to approximately the length of the field of view. The optical system objective 330 is shown below the flow cell but may also be placed above the flow cell. In addition, the flow cell can be placed in other configurations with, for example, the flow being directed vertically. The objective 330 images the capture field area 328. The first field area 324 and the second field area 326 are shown as shaded regions. In the upper figure the first field area 324 overlaps with the capture field area 328 and therefore the first field area 324 is imaged. In the lower figure the second field area 326 overlaps with the capture field area 328 and therefore the second field area 326 is imaged. By appropriately matching the flow speed, flow cell size, and optical system, all particles passing through the flow cell can be imaged, thereby providing a system for high throughput detection. Another exemplary system for high throughput flow based detection of the encoded microparticles of the invention is a flow cytometer, the methods and applications thereof are well known in the art.

Other Structures

Figure 24:
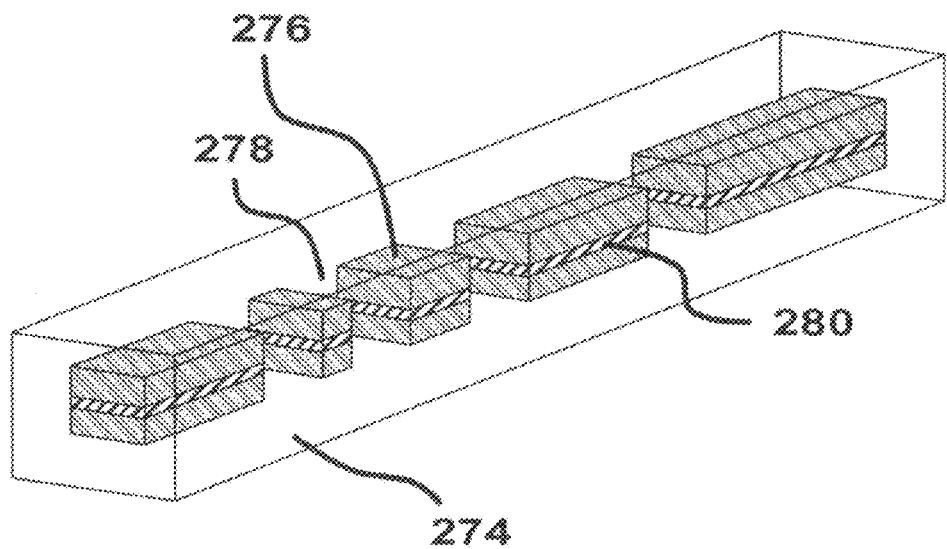
FIG. 24 illustrates another alternative microparticle of the invention.

Another alternative microparticle of the invention is schematically illustrated in FIG. 24. Referring to FIG. 24, microparticle 274 comprises opaque segments, such as 276, and gaps, such as 278, which are transmissive to the visible or near-visible light. The opaque material can be composed entirely or partially of a substantially magnetic material such as (but not limited to) nickel, cobalt, or iron. The substantially magnetic material may comprise a material selected from the group consisting of a magnetic, ferromagnetic, diamagnetic, paramagnetic, and a superparamagnetic material. The substantially magnetic material could be incorporated as a thin layer 280 sandwiched between another material that forms the majority of the opaque material. The substantially magnetic material gives the particles magnetic properties such that they can be manipulated by magnetic fields. This can aid in particle handling or facilitate the separation of biomolecules.

Figure 25:
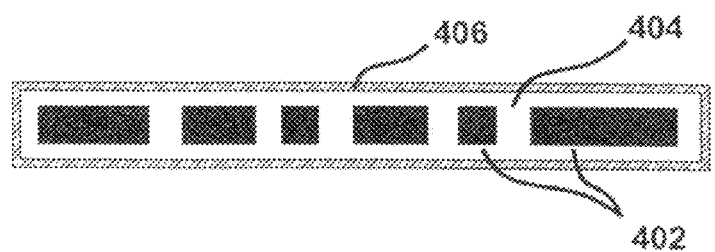
FIG. 25 shows a diagram of a spatially optically encoded microparticle with a fluorescent outer layer.

FIG. 25 shows a diagram of a spatially optically encoded microparticle with a fluorescent outer layer 406. This invention has utility in the tagging of material goods whereby the fluorescent layer improves the ability to easily find and identify the particles against diverse backgrounds. In an exemplary example, the fluorescent outer layer 406 is grown using a modified version of the Stöber process [Van Blaaderm, A.; Vrij, A.; *Langmuir.* 1992. Vol. 8, No. 12, 2921]. The fluorescent outer layer 406 makes the entire particle fluorescent and facilitates the finding of the particles during detection. The reading of the particle code can be accomplished by imaging the particle in reflectance or fluorescence mode. One may be preferred over the other depending on the application, medium in which or surface to which the particles are applied. Particles of a single code can be used or mixtures of particles of different codes can be used. The particles can be applied in a medium such as a lacquer, varnish, or ink. The particles may be used to tag paper or fibers. The particles may be used to tag objects made of metal, wood, plastic, glass or any other material.

In another example, the fluorescent layer may be comprised of fluorophores, or other luminescent materials. The fluorescent layer may interact with molecular species in an assay, for example with fluorescently labeled nucleic acids or protein samples via Fluorescence Resonant Energy Transfer processes. In yet another example, the microparticles may have a non-fluorescent layer, wherein incorporated in or on the layer are molecules, for example quenchers that interact with luminescent emitter molecules.

FIGS. 26a to 26c show schematic diagrams of encoded microparticles of the present invention with surface indentations that form a spatial code. The microparticle may be fabricated by many methods including the aforementioned examples. FIG. 26a has surface indentations, aka divots, e.g. grooves, only on the of face of the structure. FIG. 26b has divots on two faces. In other examples, divots and other desirable surface features may be placed on one or more surfaces of the microparticle structures, so as to provide a spatial code. FIG. 26c shows another example of such a structure, whereby the overall shape of the microparticle is substantially cylindrical. In an example method of making the microparticle of FIG. 26c, optical fibers having a diameter less than 1 mm may be laser or tip scribed to form the indentations. The composition of the structures of FIGS. 26a to 26c may be selected from a wide variety of materials, with glass being a preferred example.

In exemplary examples of encoded microparticles comprising indentations, the surface of the particles have fluorescent, or otherwise emitting, molecules attached to or in the surface, as shown in FIG. 26d. The emitting molecules may be covalently attached to the surface, adsorbed to the surface, or otherwise bound to the surface. In an exemplary example, the emitting molecules are incorporated into a layer which is deposited onto the microparticle. A uniform surface coverage of emitting molecules, e.g. a constant number of fluorophores per unit area, results in a nonuniform aerial density. Aerial density is defined as an intensity per unit length or per unit area that is integrated through a depth of field in an optical image plane. In this example, the aerial density is measured as an intensity profile measured by a detector, for example a CCD camera or photomultiplier tube. FIGS. 27a to 27c show the nonuniform aerial density measured normal (i.e. perpendicular) to the particle surface for corresponding particles in FIGS. 26a to 26c. The signal intensity profile has peaks corresponding to the location of the surface indentations of the particles, which thus provide a detectable and useful code. The surface features of the encoded microparticles of FIGS. 26a to 26c may be detected by methods other than the use of emitting molecules, including but not limited to the measurement of light scattering, e.g. darkfield optical microscopy, etc.

Method for Producing Codes

The invented general method of generating the codes on microparticles consists of the use of multiple lithographic printing steps of a single code element per particle region. The multiple printing steps create multiple code elements per particle region. The code elements taken together form the code for the microparticle. In a preferred example, the printing steps are performed on many particles in parallel using a master pattern. A master pattern comprises an array of single code elements per particle region. A code element may represent more than one physical feature, such as holes, stripes, or gaps. The master pattern is printed multiple times such that a multiplicity of microparticles with complete codes is formed, wherein the multiplicity of microparticles comprises identical particles (e.g. all particles have the same code). Variations upon this theme, for example wherein the multiplicity of microparticles are not identical, are anticipated and will be described in detail below. Between multiple print steps, a component of the overall printing system changes to translate the code element within the particle region. In a most preferred example, this change is a movement of the substrate on which the particles are formed. In another preferred example, this change is the movement of the master pattern. In yet other examples this change is the movement of an optical element such as a mirror.

An exemplary example of the general method of generating code using multiple print steps involves photolithography as the printing mechanism, e.g. contact photolithography and projection photolithography. An exemplary example of projection photolithographic utilizes a step and repeat system (aka stepper). A reticle contains a code pattern that has a single code element per particle. Through multiple exposures of this code pattern at different lateral offsets, a multiplicity of code elements (per particle) is created. Combined, these code elements form a complete code. The lateral offsets define the code and are programmed into the stepper software. The offsets, and therefore the code, can be changed on a per die or per wafer basis. The codes printed on different dies on a wafer and/or different wafers in a lot are thus controlled by software and can be arbitrarily changed. This enables a powerful flexibility in the manufacture of large sets of codes. A single mask set, having one to a few masks, can be used to generate an arbitrary number of codes, numbering into the $10^5$ range and beyond.

FIG. 28a to FIG. 28c shows an exemplary example of the invented method of producing the codes for microparticles. The microparticle regions 290 are areas that, upon completion of the fabrication process, will be discrete particles. FIG. 28a shows the status after the printing of the first code element 292 in each microparticle region 290, in this exemplary example the code elements are vertical stripes. FIG. 28b shows the status after the printing of a successive code element 294 in each microparticle region 290. FIG. 28c shows the status of the printing of three more code elements 296 in each microparticle region 290. The multiple printing steps thus provide codes on the microparticles.

FIG. 29a to FIG. 29c shows another example of the invented method of producing the codes for microparticles.

The microparticle regions 300 are areas that, upon completion of the fabrication process, will be discrete particles. FIG. 29a shows the status after the printing of the first code element 302 in each microparticle region 300, in this exemplary example the code elements are circular. FIG. 29b shows the status after the printing of a successive code element 304 in each microparticle region. FIG. 29c shows the status of the printing of three more code elements 306 in each microparticle region 300. The multiple printing steps thus provide codes on the microparticles.

FIG. 30a to 30c show drawings of the 3 mask fields of the preferred embodiment of the microparticle structure and FIG. 30d shows a drawing of a reticle plate. FIG. 30a to 30c are small representative areas of the much larger full field (only 46 of approximately 2 million particles are shown). In these drawings, the regions that are gray have chrome on the actual reticle (so called "dark" in reticle terminology), and the regions that are white have no chrome (so called "clear"). Physically, the reticles are glass plates that usually measure 5" to 6.25" square and are about 0.09" thick. They are coated with a thin (a couple hundred nm) layer of chrome. The chrome is patterned with a resist through a serial lithography process, usually using a laser or ebeam system. The reticle is then wet etched which selectively removes the chrome. The final reticle then consists of a glass plate with chrome on one side in the desired pattern.

The code pattern, shown in FIG. 30a, has vertical stripes 110 that are clear. There is one vertical stripe per particle. FIG. 30b shows the bar pattern, which consists of horizontal stripes 112 that are dark (or equivalently wider horizontal stripes that are clear). The outline pattern, shown in FIG. 30c, consists of rectangles 114 that are dark. Clear streets 116 extend in the horizontal and vertical directions, separating the rectangles 114. The rectangles 116 will form the outer border of the particles. The horizontal stripes 112 define the width of the inner segments of opaque material. The vertical stripes 110 form the gaps in the segments. The gaps both form the code in the particle and separate two adjacent particles. FIG. 30d shows a full reticle plate. The reticle field 118 is the center region of the reticle which contains the pattern to be exposed. Alternate examples of the patterns described are also envisioned, including combining the code and bar pattern into a single pattern that can used according to the described multi print method.

An exemplary example of the invented method for producing codes uses photolithography and positive-tone photoresist. Positive-tone means that the areas exposed to light are developed away. For a negative-tone resist, exposed regions are what remain after development. The photocurable epoxy SU-8 is an example of a negative-tone resist. In an alternate example using a negative-tone resist such as SU-8, the regions that are to be segments are exposed to light instead of the regions that are to be gaps.

FIGS. 51a to 51c show flowcharts of examples of the code element patterning and etch steps. FIG. 51a shows the case where a hard mask is not used. This process is simpler but may produce segments with rounded corners because of the proximity effect of the photoresist exposures. At the corners of the segments, the photoresist gets some residual exposure from both the vertical stripes of the code pattern and the horizontal stripes of the bar pattern. The resulting rounding of the corners, though within the scope of the invention, is less desirable because it produces final particles that look different from the side vs. the top and bottom surfaces. The extent to which the rounding occurs depends on the specifics of the photolithography process including the pattern on the reticles, wavelength of the light source, and photoresist. FIG. 51b shows an exemplary example of the multi print method based patterning process and is described in detail in the below FIGS. 32a to 32m and FIGS. 33a to 33m. FIG. 51c shows another example of the particle fabrication process where instead of transferring the bar pattern to the hard mask, the bar pattern photoresist is used as the mask in conjunction with the hard mask oxide. This example method eliminates a few steps but may not be appropriate depending upon the specifics of the poly etch chemistry.

An alternate example of the general method of generating code using multiple print steps utilizes stamping (aka imprint lithography) as the printing mechanism, and is schematically depicted in FIG. 31. FIG. 31 schematically shows a small region of an example master pattern for stamp printing according to the invented multi-print-steps-to-build-the-code-up method, e.g. 1) stamping or pressing a stamper apparatus into the particle containing substrate, followed by 2) moving either the stamper apparatus or the substrate, and 3) stamping at least one more time in a nearby location, such that a complete code on the microparticles is formed. The substrate on which the microparticles can be formed using imprint lithography may be a wafer, such as a 100 mm, 150 mm, 200 mm, or 300 mm silicon wafer, or a panel, such as a 5" or larger glass or quartz panel, or rolled sheets (including but not limited to polymeric sheets).

Figures 32M, 33M:
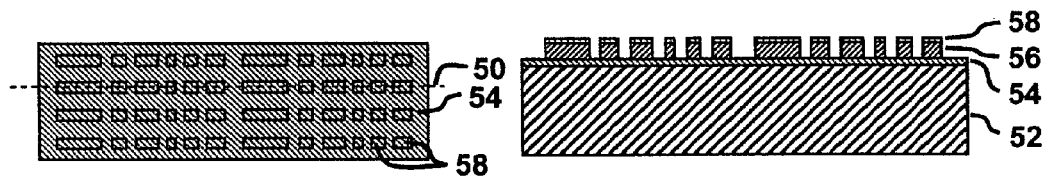

FIGS. 32a to 32m and 33a to 33m illustrate the microfabrication process steps of the example encoded microparticle of FIG. 1a. These steps define the inner opaque segments (which contain the code). The steps are shown in more detail than in FIG. 6a to FIG. 6m and include the photoresist exposure and development. FIG. 32a to FIG. 32m show top down drawings and FIG. 33a to FIG. 33m show the corresponding cross sectional views. The cross-section line 50 is shown in FIG. 32a to FIG. 32m. In FIG. 32a, the top surface is the hard mask oxide 58. In FIG. 33a, the film stack on the starting substrate 52 consists of the bottom oxide 54, poly 56, and hard mask oxide 58. In FIG. 32b the wafer has been coated with unexposed photoresist 120. The unexposed photoresist 120 is shown as the top layer in FIG. 33b. In FIGS. 32c and 33c, the unexposed photoresist 120 has been exposed with the code pattern a single time, forming exposed photoresist 122 regions. In FIGS. 32d and 33d, the code pattern has been exposed multiple times with lateral offsets applied between the exposures. In the preferred embodiment, the code pattern is exposed twice in directly adjacent regions to form double width stripes 124. Single width stripes 126 are the "gaps" that form the code. The double width stripes 124 are located in between the particles and separate the particles. To clarify, the lateral offsets are achieved by moving the stage on which the wafer sits. The lateral offsets are programmed into the stepper software. The lateral offsets define the code of the microparticles on that die. The lateral offsets (and thus code) can be different for every die on a wafer. Each wafer in a lot of wafers can have a different set of codes. In this way, very-large code sets can be realized.

FIGS. 32e and 33e show the wafer after development of the photoresist. The exposed photoresist 122 from FIGS. 32d and 33d is removed revealing the underlying hard mask oxide 58. FIGS. 32f and 33f show the wafer after the oxide etch. The oxide etch removes the hard mask oxide 58 in the exposed regions revealing the underlying poly 56. FIGS. 32g and 33g show the wafer after the unexposed photoresist 120 of FIGS. 32f and 33f is removed. The hard mask oxide 58 is present in the regions that will become the segments. The poly 56 is exposed in the regions that will become the gaps in the opaque material. FIGS. 32h and 33h show the wafer after it is again coated with unexposed photoresist 120.

FIGS. 32*i* and 33*i* show the wafer after the exposure of the bar pattern. This is just a single exposure and is the same on all dies. This exposure is preferably aligned to the pattern already on the wafer. After exposure, the unexposed photoresist 120 pattern consists of horizontal stripes which define the segment width. The exposed photoresist 122 pattern consists of horizontal stripes which define the horizontal separations between the segments. FIGS. 32*j* and 33*j* show the wafer after the development of the photoresist. The exposed photoresist 122 from FIGS. 32*i* and 33*i* is removed revealing the underlying hard mask oxide 58 and poly 56. FIGS. 32*k* and 33*k* show the wafer after the oxide etch of the hard mask oxide. Only the poly 56 is present in the exposed photoresist region of FIG. 32*i*. FIGS. 32*l* and 33*l* show the wafer after the unexposed photoresist 120 is removed. At this point in the process, the top surface of the wafer is poly 56 with hard mask oxide 58 covering the poly 56 in the regions which are to become the segments of opaque material. Finally, FIGS. 32*m* and 33*m* show the wafer after the poly etch. The poly etch removes the poly 56 of FIGS. 32*l* and 33*l*, revealing the underlying bottom oxide 54. The hard mask oxide 58 is still present on the top surface of the poly 56 in the segment pattern.

In addition to the microparticle as illustrated in FIG. 1*a*, the methods above can be used to produce the codes for other encoded microparticle designs including currently known particle designs as well as other alternative designs. The method above can be used to produce the codes for the encoded microparticles, for example, in FIGS. 35A to 35C.

Figure 34A:
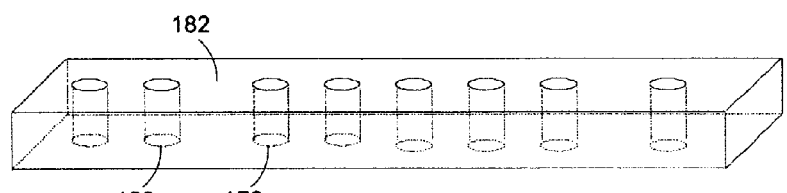
FIG. 34a to FIG. 34c show exemplary microparticles that can be produced using the method of the invention.

Referring to FIG. 34*a*, a bar-shaped microparticle with code elements consisting of holes such as holes 178 and 180 that are surrounded by frame material 182. The number and the arrangement of the holes forms a code derived from a predetermined coding scheme.

Figure 34B:
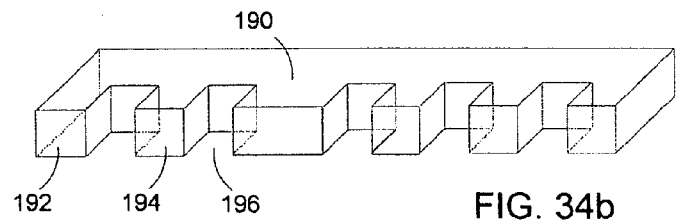
Figure 34C:
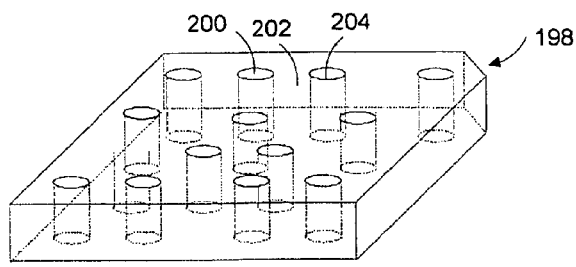

FIG. 34*b* shows another bar-shaped particle with the code elements comprising notches, such as notch 196. The adjacent notches define a set of protruding structures with different widths. The total number of protruding structures and the arrangement of the protruding structures with different widths represent a code derived from a coding scheme. FIG. 34*c* shows a square plate shaped particle with the code elements consisting of holes, such as holes 200 and 202 that are separated by gap 202. The plate particle also includes an indentation 198 in one corner to break the symmetry of the particle and thus allow for more codes. Further shapes and code element architectures can also be made with the aforementioned method of producing codes.

Figure 35:
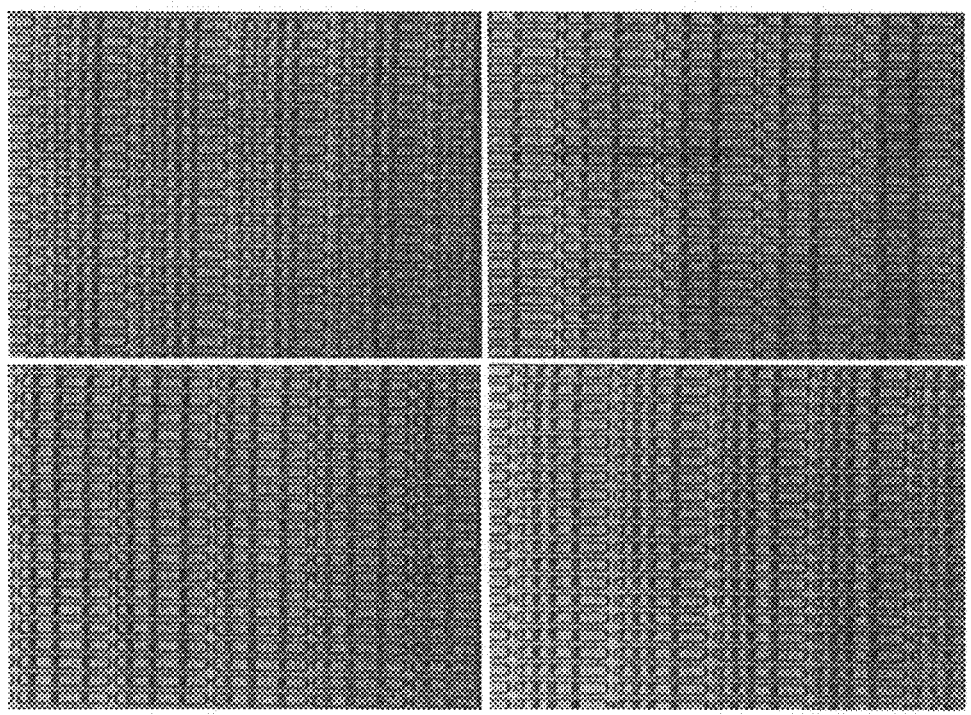
FIG. 35 shows four microscope images of actual encoded microparticles, just prior to release from the dies.

FIG. 35 shows four microscope images of actual encoded microparticles, just prior to release from the dies. These particles are produced according to the invented technique of producing codes with multiple print steps and according to designs described above.

Figure 36:
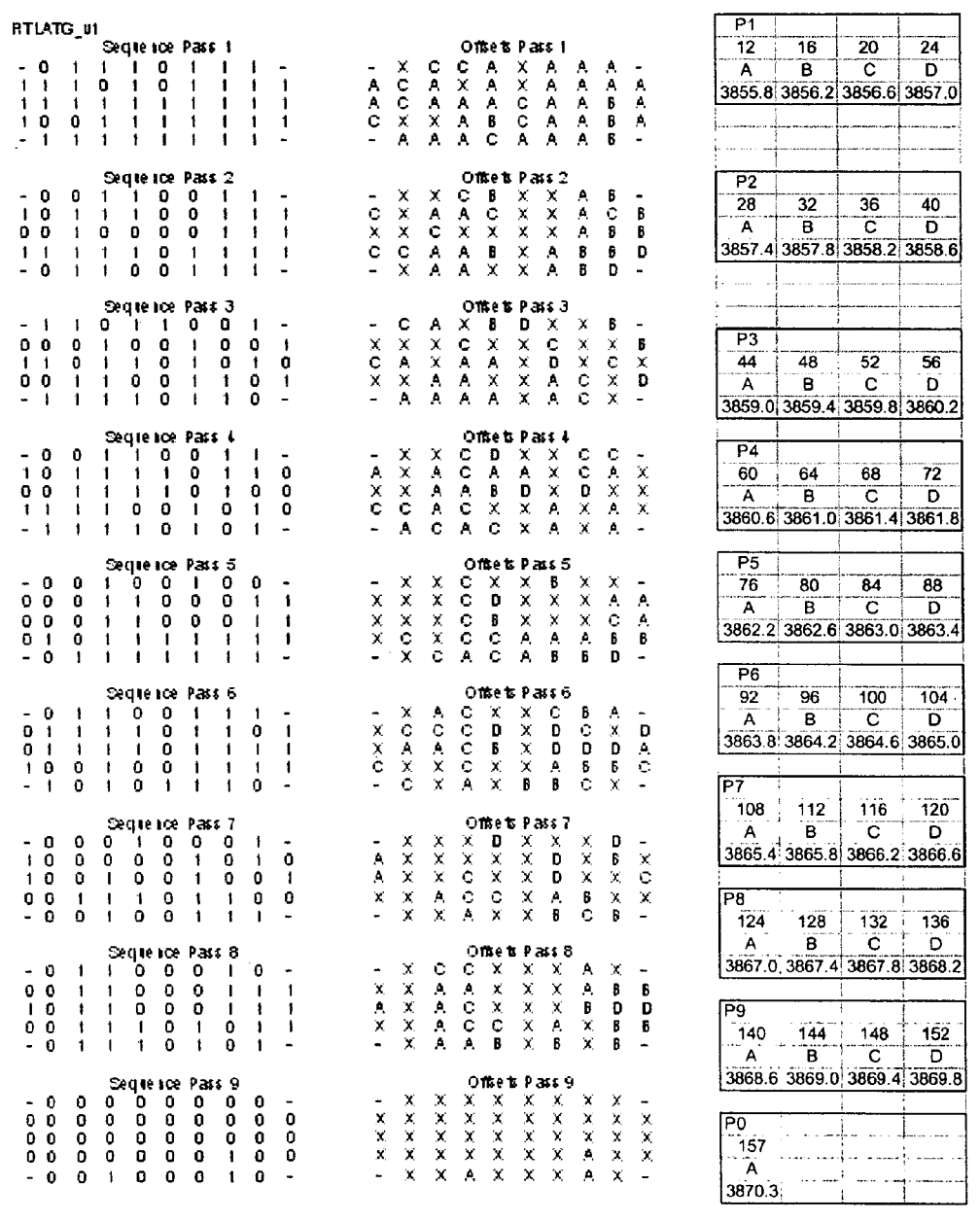

FIG. 36 shows charts of example data that is input into the stepper software to generate different codes on every die on a wafer. The charts show which dies get printed in 9 different passes and with what offsets. The data shown in FIG. 36 is an example of one system for organizing the multi print method using a stepper for providing a multiplicity of codes on a multiplicity of dies on a wafer. In this example, each die is exposed at most one time during a single pass. A wafer map of which dies are to receive exposures during the stepper exposure passes in this example is shown in the column on the left. "1" designates exposure. "0" designates no exposure. The middle column shows a wafer shot map of the exposure offsets, designated with offset letters "A", "B", "C", and "D". The right column shows a lookup chart of 1) the exposure location relative to the end of the particle, 2) the offset letter, and 3) the exposure locations programmed relative to a stepper reference point. The rows correspond to the different passes, 9 in this example.

Another example of a system for organizing the multi print method using a stepper is to exposure all of the code elements within a single die before moving on to the next die. Of course, a number of offsets other than four could be used. Though this and other examples of the general method of producing codes on microparticles has been described with respect to using a projection photolithography and a stepper, contact lithography and other patterning methods may also be used.

Figure 37:
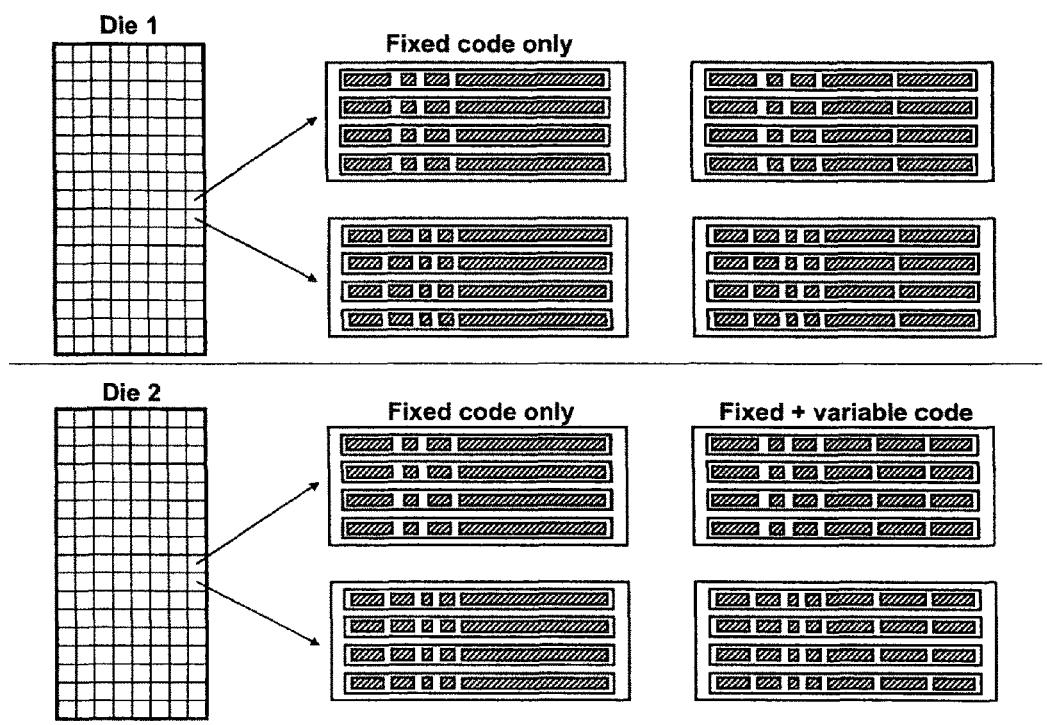
FIG. 37 shows drawings of an example scheme for producing an increased number of codes per die.

FIG. 37 shows drawings of an example scheme for producing an increased number of codes per die. In this scheme, within a die there are fixed and variable code element locations. Dies are divided into sub regions where each sub region has a different pattern of fixed code elements. For each die, a different pattern of variable code elements is exposed. The fixed and variable code elements together make up the entire code. A single wafer thus contains a total number of codes equal to the product of the number of dies per wafer and sub regions per die. An individual die, containing sub regions of different codes, could be physically separated into smaller sub-dies and the different codes released into different tubes. An alternative is to keep the dies intact and release the whole die into a single tube This would create a mixture of codes from the different sub regions. This approach may be particularly useful for combinatorial synthesis applications.

The invented method of producing codes, for example the use of a photolithographic step and repeat system to form a complete code through multiple exposure steps of a single reticle field, may be used to apply unique codes to many types of components, e.g. MEMS and IC devices.

Coding Scheme

The microparticles as discussed above have incorporated therein codes derived from any desired coding scheme, such as binary or non-binary coding.

Figure 38A:
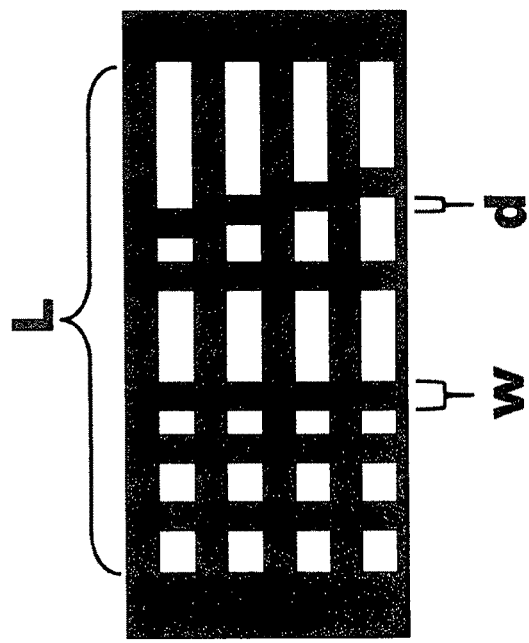
FIG. 38a shows a graphical representation of encoded microparticles that are formed according to the invented non-binary coding scheme.
Figure 38B:
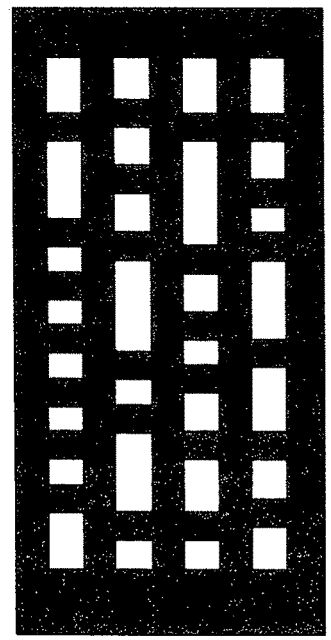
FIGS. 38b and 38c show random codes with different numbers of gaps and gaps of varying location.
Figure 38C:
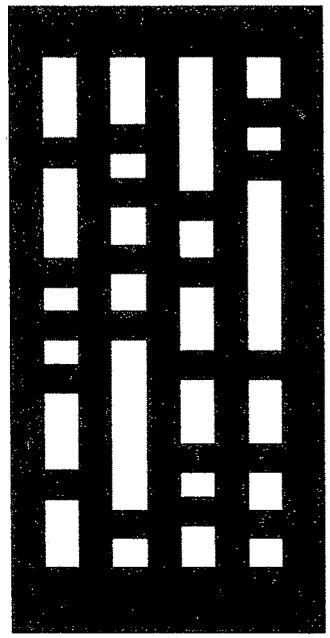

By way of example, FIG. 38*a* shows a graphical representation of encoded microparticles that are formed according to the invented non-binary coding scheme. Referring to FIG. 38*a*, the coding scheme parameters are L (the length of the particle), w (the width of the gap between segments), and d (the delta in the position of the gap center of the gap). FIG. 38*a* shows 4 particles with different codes such that only one of the gaps is varied in location. The gap is varied by amount equal to d, showing "adjacent" codes (e.g. codes that are similar and therefore more likely to be mis-identified for one another. FIGS. 38*b* and 38*c* show random codes with different numbers of gaps and gaps of varying location. Table 2 presents the total number of codes (codespace) for a variety of different parameter combinations. The number of codes is calculated from a computer software program that implements the invented non-binary coding scheme. Code degeneracy is taken into account in the algorithm (e.g. a pair of codes, such that when one is reversed, the codes are equivalent and the two codes are considered a single code). The parameters in Table 2 and Table 3 are specified in 100 nm units. The parameter combination L=152, w=8, d=4 which gives 30,069 is shown in FIGS. 38*a* to 38*c*. Table 3 presents the total number of codes that can be represented by the microparticles by different L. In an exemplary example, the discretization distance w is equal to or smaller than the characteristic segment size. As shown in Table 3, very large codespaces are available, and practically achievable with the aforementioned methods. The parameter combination L=152, w=5, d=4 has a codespace of approximately 2 million.

TABLE 2

| L | w | d | Number of Codes (Codespace) |
|---|---|---|---|
| 152 | 8 | 8 | 2134 |
| 152 | 8 | 7 | 3281 |
| 152 | 8 | 6 | 5846 |
| 152 | 8 | 5 | 11439 |
| 152 | 8 | 4 | 30069 |
| 152 | 8 | 3 | 105154 |
| 100 | 5 | 5 | 3,409 |
| 110 | 5 | 5 | 8,904 |
| 120 | 5 | 5 | 23,296 |
| 130 | 5 | 5 | 62,376 |
| 140 | 5 | 5 | 170,083 |

TABLE 3

| L | w | d | Number of Codes (Codespace) |
|---|---|---|---|
| 80 | 5 | 4 | 928 |
| 90 | 5 | 4 | 2,683 |
| 100 | 5 | 4 | 7,753 |
| 110 | 5 | 4 | 22,409 |
| 120 | 5 | 4 | 64,777 |
| 130 | 5 | 4 | 187,247 |
| 140 | 5 | 4 | 541,252 |
| 150 | 5 | 4 | 1,564,516 |
| 152 | 5 | 4 | 1,934,524 |
| 160 | 5 | 4 | 4,522,305 |

In an exemplary example, the coding scheme utilizes code elements placed at locations spanned by interval lengths smaller than the code element size itself. This deviates from the standard binary coding where the code consists of the absence or presence of a feature at discrete, evenly spaced locations. In the preferred embodiment of this coding scheme, naturally applicable to the above structure manufactured using the multiple print technique, the code element is the gap in the segmented inner opaque material. The gap size is chosen to be one that is reliably defined by the stepper and photolithography process and also resolvable by the microscope (working at the desired magnification). The gap size, interval length, and particle length determine the codespace (number of codes possible). The determination of a codespace involves tradeoffs between particle density on the wafer, identification accuracy, optical detection system complexity, and particle number per microscope image. Codespaces of over a million can be produced and accurately identified using practical parameter combinations.

In the example of a standard binary coding scheme, the particle would be divided into units of equal length. Each unit could then be black or white, 0 or 1. Because the particle is symmetric, there are two codes that are the same when one is reversed (so called "degenerate" codes). When counting the codes, one from each of the pair of degenerate codes is preferably discarded. Without the degeneracy, there would be $2^N$ possible codes, where N is the number of bits (units). With the degeneracy, there are about half that number. Exactly, the number of possible codes with the standard binary format is $[2^N+2^{floor[(N+1)/2]}]/2$. In the example of the high contrast encoded microparticle structures of the present invention, previously shown in FIG. 13, FIG. 16, etc., within the full set of codes, there may be individual codes that have long runs of black or white regions. The black of the particles is indistinguishable from the black of the background, giving the particles extremely high contrast. However, codes having long runs of black are less desirable (though certainly within the scope of the invention) because it is more difficult to associate the white regions into the separate particles. For example, a more difficult code would be 1000 . . . 0001 (single white bits at both ends). It should be noted that, particularly for the structures and methods of making mentioned earlier herein, any suitable coding scheme can be used, as many other coding schemes are possible beyond that discussed in the example above.

The non binary coding scheme mentioned above has many advantages in the fabrication and detection of microparticles, including providing for high codespaces and robust code identification. In the example of the coding scheme, the reliability of the microparticle fabrication process is improved by permitting optimization of patterning and etch conditions for features, of a single size, e.g. gaps in the segments having a single width.

In the exemplary examples of encoded microparticles and methods of determining codes therein, e.g. as shown in FIG. 20, the code is determined by the center location of the gaps and not the lengths of segments. Therefore, if the dimensions change, either because of variation in the manufacture or variation in the imaging conditions or variation in the image processing algorithm used, the center position of the gaps does not change, rendering the code ID is robust. This scheme exploits the fact that in an optical imaging system the position of features, in this case the gaps, can be located to a resolution much smaller than the minimum resolvable dimension of the features themselves. For example, if the gap width may be 1.5 um or less, and located to a distance smaller than 1.0 um, more preferably smaller than 0.5 um.

In general, a high codespace is desirable. In the field of genomics, having a codespace in the tens of thousands is especially important because it enables full genomes of complex organisms, such as the human genome, to be placed on a single particle set. The top portion of Table 2 shows the effect of varying the delta parameter, d, on the codespace. Shrinking d gives many more codes but places increased demand on the optical system. The need to resolve a smaller d means that a more expensive objective would typically be used. Practically, the lower limit of the gap interval distance is set by the resolution by the optical system (manifested as the pixel size of the digital image captured using a CCD camera). Using a 60× objective and 6.2 mm 1024×1024 CCD chip, an interval distance of d=0.4 um equals approximately 4 pixels. If the interval distance is reduced to 0.3 um (3 pixels), there are 105,154 codes. The codespace can be extended into the millions for longer particle lengths, L, and/or smaller gap widths, w.

The lower portion of Table 2 shows the effect of varying the length of the particle at fixed w and d. The length L is inversely proportional to the density of particles on the die (number of particles per unit area). The length also affects the number of particles in an image and thus throughput (particles detected per second). Tradeoffs exist between codespace, density, identification, and throughput. Optimization of the coding scheme parameters will determine the selected coding scheme for a particular application.

Large Particle Sets

Figure 39:
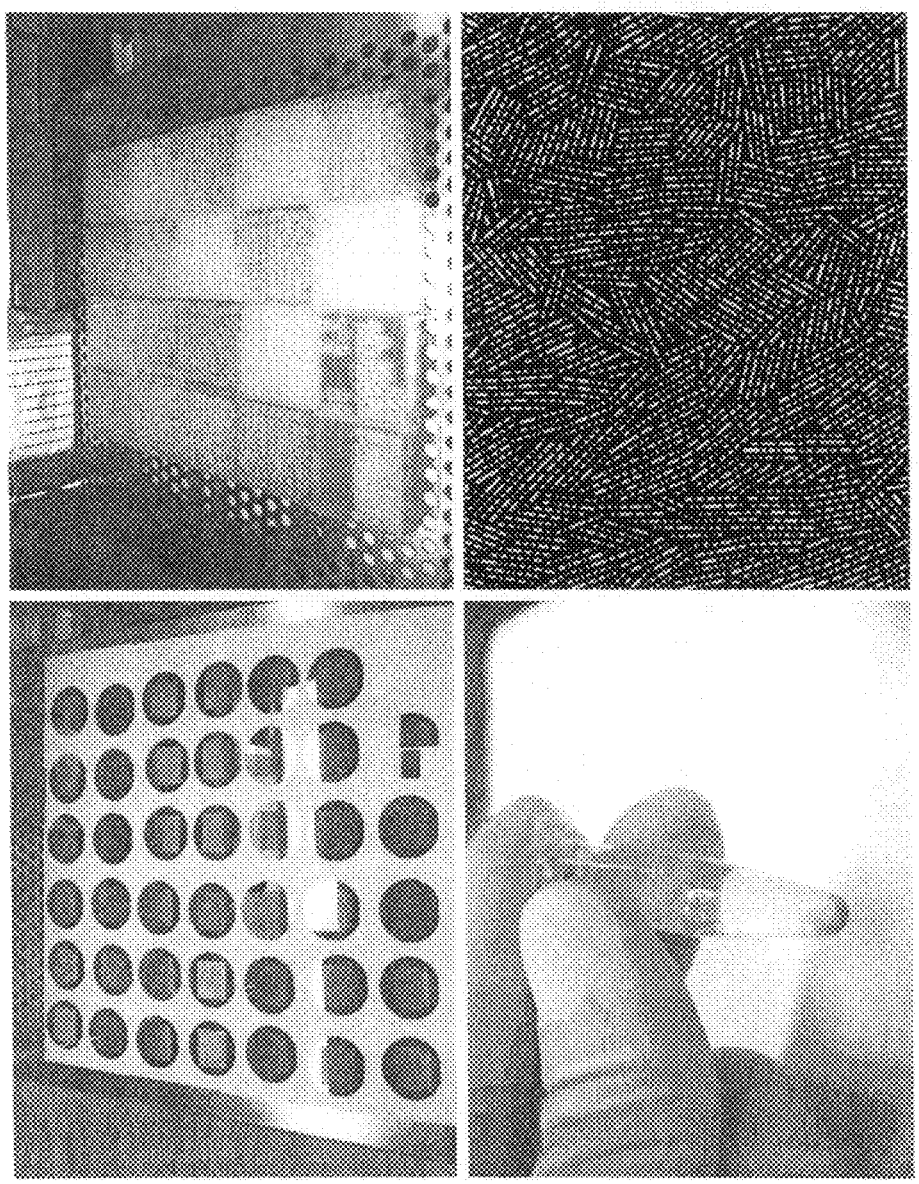
FIG. 39 shows photographs a montage of 4 photographs of various forms of a large prototype set of microparticles.

FIG. 39 shows photographs a montage of 4 photographs of various forms of a large prototype set of microparticles. The set contains over 1,000 codes and approximately 2 million particles of each code. The upper left photograph shows 40 wafers during the fabrication process. Each wafer has 32 dies with each die comprising approximately 2 million particles of a single code. As a further example, dies on a wafer may contain many more particles per wafer, e.g. 5 million or more.

Also, wafers (or other substrates, such as glass panels), may contain 100 or more dies, or alternately 200 or more, or 1000 or more dies. The wafer taken in whole may have 100 or more codes of encoded microparticle, or alternately 200 or more, or 1000 or more codes, or 5,000 or more codes. In an exemplary example of a large set of encoded microparticles, substantially all dies used to produce the large set, e.g. microparticles released from dies, comprise different codes. In another example, all dies on a wafer or substrate, may have the same code. The size of dies may be selected so as to optimize the balance between the number of particles per code and the number of codes in the large set of a large set. The number of particles per die and dies per wafer may be changed in software, for example by utilizing the invented method of producing codes, and optimized on a per manufacturing lot or per product basis for different applications, without necessitating the high capital costs of fixed tooling, e.g. large and expensive sets of photomasks.

In the upper right photograph of FIG. 39, the wafer fabrication has been completed and the particles released from the silicon substrate into test tubes. The test tubes are shown in the photograph in placed in containers that each hold 64 test tubes. The photograph in the lower left corner shows a single test tube which contains a small portion (approximately a few thousand particles) of each of 1035 test tubes of particles from the large set. The lower right image is a microscope image of a sample of the single test tube. This image shows members of 1035 codes mixed together.

Assays

The encoded microparticles, systems, and methods of the invention have a wide range of applications in the fields of biology, chemistry, and medicine, as well as in security and commercial fields involving the tagging of monetary bills, identification cards and passports, commercial products, and the like. In one example, the microparticles can be used in for molecular detection, such for as analyzing DNA, RNA, and proteins. In other examples, combinatorial chemistry or drug screening assays are performed as known in the art.

Figure 40:
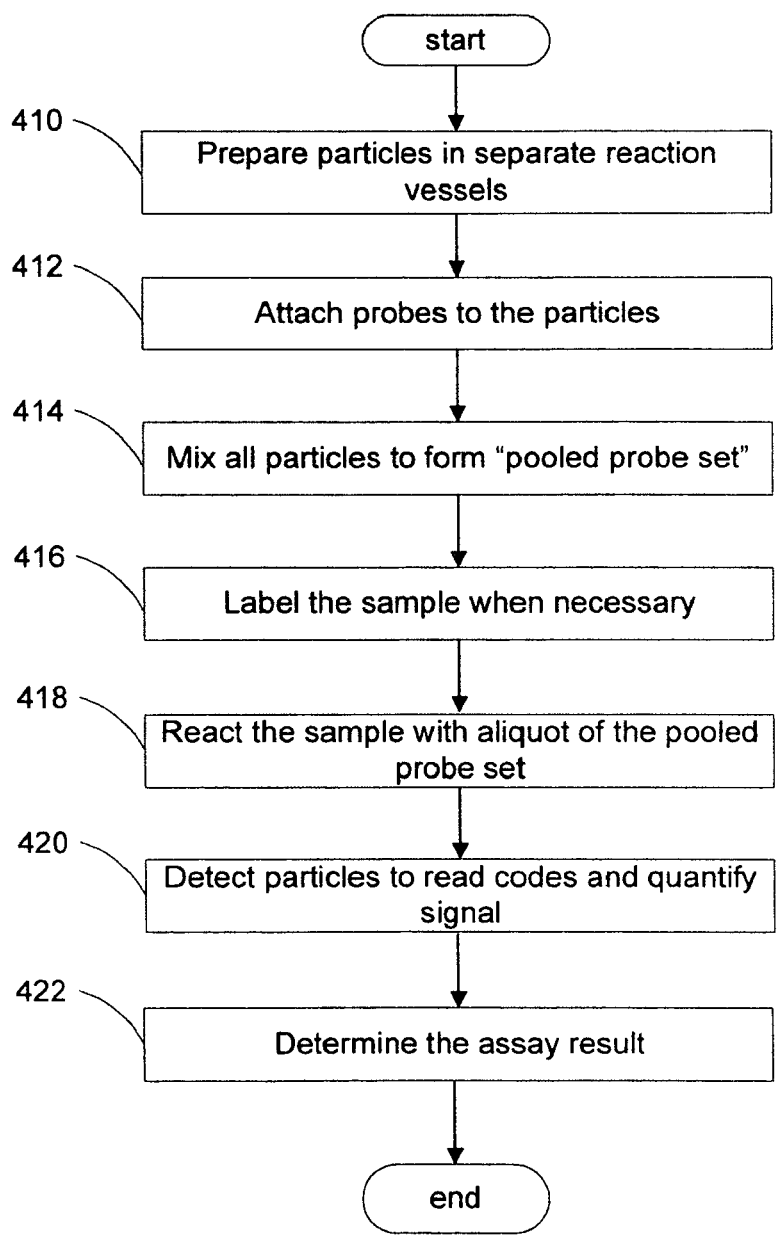
FIG. 40 is a flow chart of an exemplary bioassay process.

Referring to the flowchart shown in FIG. 40, microparticles are contained in separate tubes (or wells of well plates). Each tube contains a large number (e.g. a million or higher) of microparticles of a single code, at step 410. Biomolecules, such as DNA or RNA are immobilized on the surface of the particles and referred to as "probes" at step 412. Each species of probe is immobilized onto a different code and a lookup table is generated for future reference. Each species of probe also has one or more corresponding species of "targets" for which the binding between the two is specific (i.e., binding-pairs). The probe/target terminology is usually used in reference to DNA and RNA complements but in this context refers to all biomolecules, including antibodies. Many probes are immobilized on a single particle, typically with a density on the order $10^4/um^2$ or higher. The singular use of "a probe" often refers to a plurality of probe molecules; and "a code" often refers to a plurality of particles of a certain code, as with other terms used herein.

The mating of the encoded particles and biomolecules produces a "pooled probe set" through step 414. The pooled probe set is a mixture of encoded particles where each code has a particular probe attached to the particle surface. The pooled probe set can then be used to determine the amount of individual targets present in a mixture of targets. The mixture of targets is referred to as the sample and is typically derived from a biological specimen. The sample is then labeled, typically with a fluorophore at step 416. When the sample is mixed with the pooled probe set, the probes and targets find each other in solution and bind together. With nucleic acids, this reaction, step 418, is called hybridization and is very selective. After the reaction, the particles are imaged to read the codes and quantify the fluorescence at step 420. Referring to the code-probe lookup table, the amounts of the different target species in the mixed sample can now be measured and as the assay result determined at step 422.

The samples reacted with the microparticles may be a purified biological extract or a non-purified sample, including but not limited to whole blood, serum, cell lysates, swabs, or tissue extracts. The samples reacted with the microparticles may be produced by culturing, cloning, dissection, or microdissection. Cells may serve as either the sample or probe in a bioassay utilizing the microparticles and other aforementioned inventions.

Figure 43:
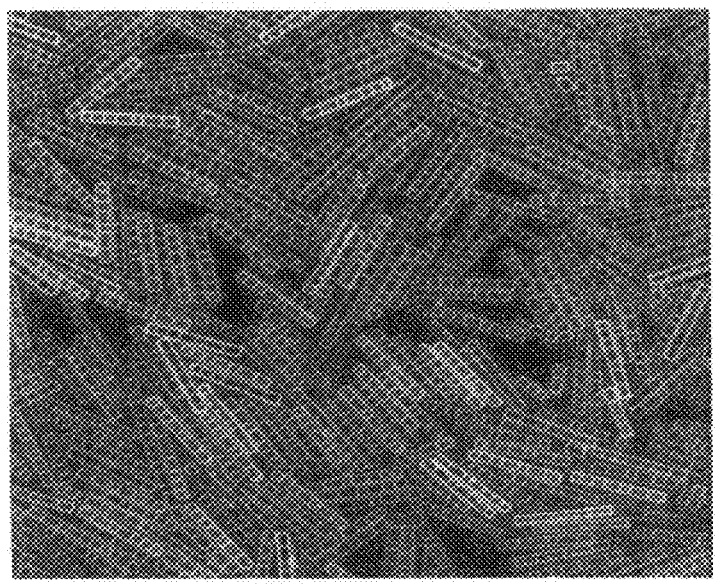
FIGS. 43 and 44 show dense fluorescence microscope image of a multiplicity of encoded microparticles.
Figure 44:
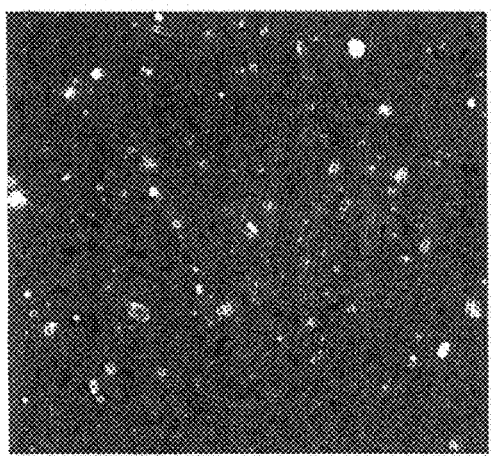

FIGS. 43 and 44 show dense fluorescence microscope image of a multiplicity of encoded microparticles. The microparticles shown in the images have oligo probe molecules attached to their surfaces and have been hybridized to pre-labeled fluorescent oligo targets, where the base pair sequence of the targets is complementary to the sequence of the probes.

Figure 41:
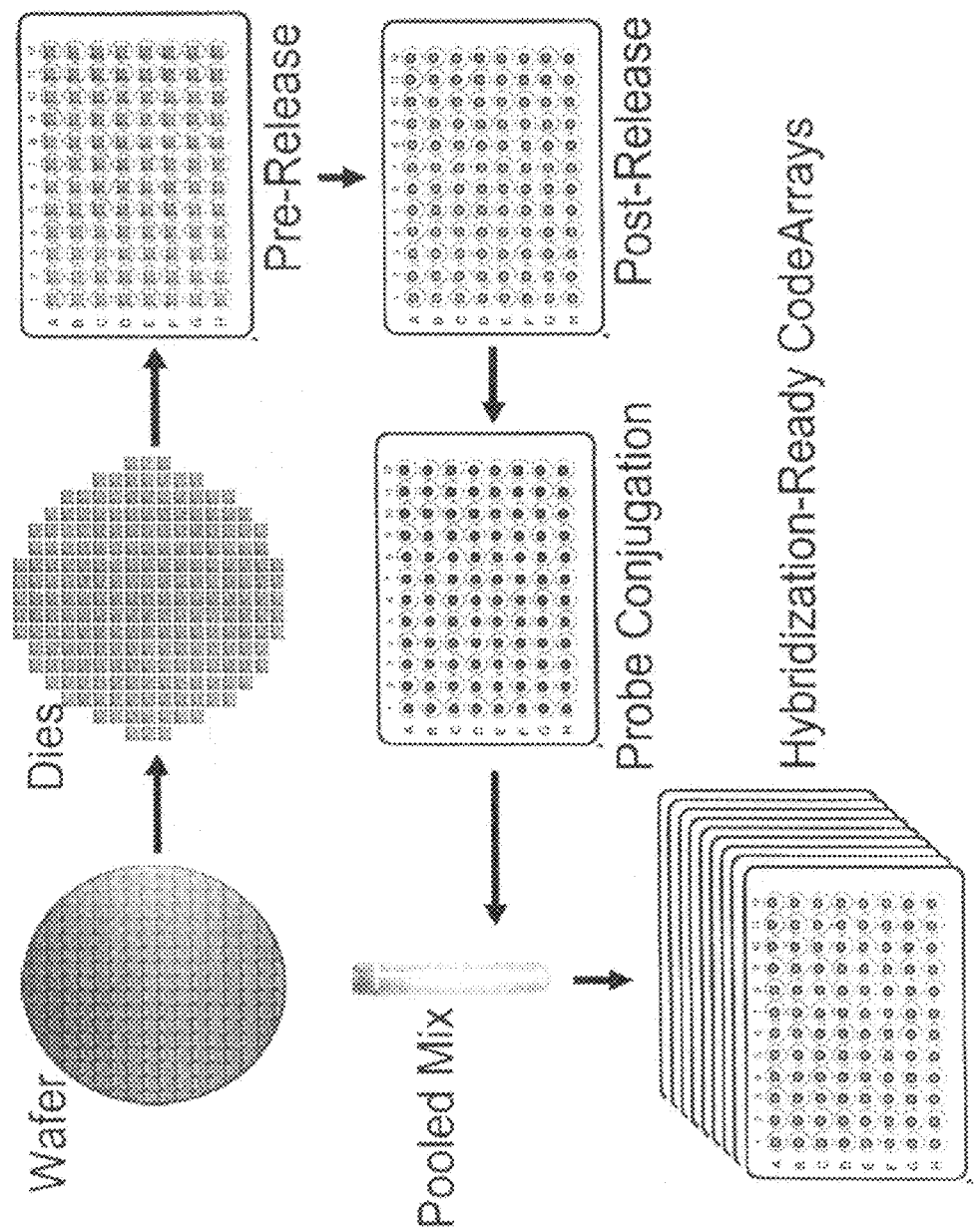
FIG. 41 shows a diagram of an exemplary example of the process by which whole wafers become mixtures of particle-probe conjugates that are ready to be reacted with samples to perform a bioassay.

FIG. 41 shows a diagram of an exemplary example of the process by which whole wafers become mixtures of particle-probe conjugates that are ready to be reacted with samples to perform a bioassay (so called "Hybridization-Ready Code-Arrays"). After completion of the wafer fabrication steps, the wafer has many dies where each die contains many particles of a single code. As has been previously described, alternative schemes may be used where dies are produced with the same code or dies are subdivided and contain multiple codes. The wafer is diced (usually by wafer saw) into the separate dies, then each die is placed into separate wells of a wellplate. Alternatively, test tubes can be used instead of wells. A release step is performed e.g. using a chemical etchant such as TMAH) that removes the particles from the surface of the die. The die is then removed from the well, leaving the free particles. After release, the conjugation of the biomolecule probes is performed resulting in each well containing a single type of particle probe conjugate (with particles of a single code and those particles having a single species of biomolecule on the surface). After conjugation, all of the particles are mixed together to form a "pooled master mix". The pooled master mix is divided into aliquots such that sufficient representation from all species of particle-probe conjugates is present. These aliquots are then ready to be reacted with a sample to perform a bioassay.

It is noted that multiple different samples may be identified in a single bioassay as discussed above. Before the detection and after the hybridization, the microparticles can be placed into wells of a well plate or other container for detection. In one detection example, the microparticles settle by gravity onto the bottom surface of the well plate. The microparticles in the well can be subjected to centrifugation, sonication, or other physical or chemical processes (multiple washing steps, etc.) to assist in preparing the particles for detection. In another example, the microparticles can be placed onto a glass slide or other specially prepared substrate for detection. In yet other examples, the particles are present in a flow stream during detection, or present in a suspended solution.

Term conjugation is used to refer to the process by which substantially each microparticle has one or more probe molecules attached to it's surface. Methods of conjugation are well known in the art, for example in Bioconjugate Techniques, First Edition, Greg T. Hermanson, Academic Press, 1996: Part I (Review of the major chemical groups that can be used in modification or cross-linking reactions), Part II (A detailed overview of the major modification and conjugation chemicals in common use today), and Part III (Discussion on how to prepare unique conjugates and labeled molecules for use in applications). Reagents for conjugating probe molecules are readily available from scientific supply houses such as Pierce Biotechnology, Inc. or Sigma-Aldrich, Co.

The molecular probes attached to the surface of the particles typically have known attributes or properties. In an example, the molecular probes can be derived from biological specimens or samples and used in the screening, including but not limited to genetic sequencing, of large populations where typically, the derivatives from one member of the population is applied to a single code, typically a multiplicity of particles of a single code. Preferably, microparticles having the same code have attached substantially the same probe molecules; whereas microparticles having different codes likewise have different probe molecules.

One of the most powerful features of a multiplexed assay using solution arrays of encoded particles as the platform instead of planar microarrays is the flexibility to add functionality to the assay by simply adding new particles. With standard microarrays, once the arrays are printed or synthesized, the array typically cannot be changed. If the researcher wants to change the probes for genes on the array or add probes for new genes, typically entirely new arrays would then be produced. With pooled probe sets of particles, new probe and particle conjugates (probes for short) can easily be added to the existing pooled probe set. In practice the new probes could be different probes for an already represented gene, probes for alternative splicing variants of genes, or tiling probes for genes.

Figure 45C:
FIG. 45c shows the image pair of FIG. 45a and FIG. 45b overlaid.
Figure 45A:
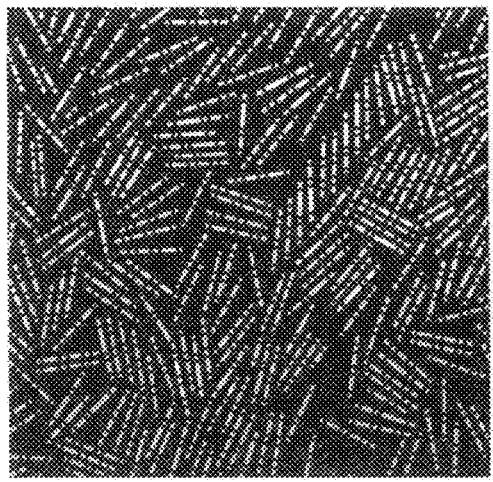
FIG. 45a and FIG. 45b show a reflectance and fluorescence image pair for the same set of microparticles of the invention.
Figure 45B:
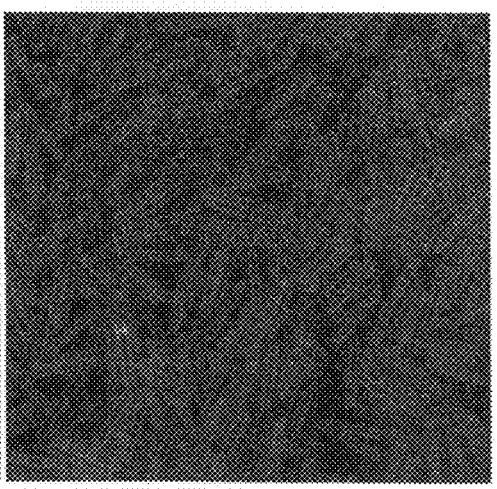
Figure 46A:
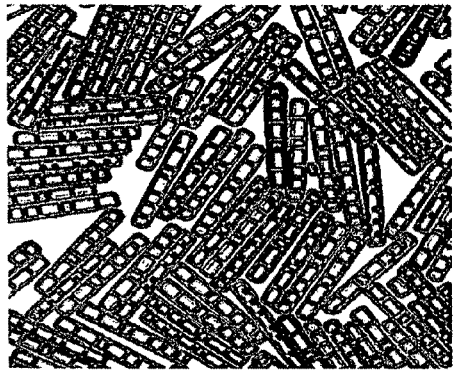
FIG. 46a to FIG. 46f show dense fluorescence microscope images of encoded microparticles in a time sequence.
Figure 46B:
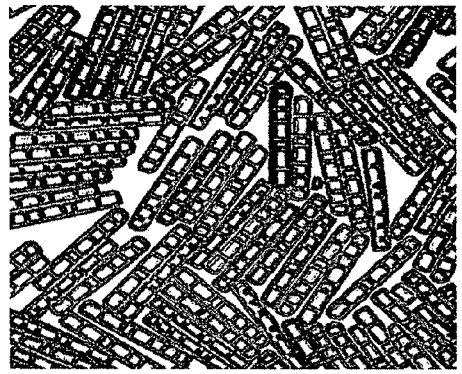
Figure 46C:
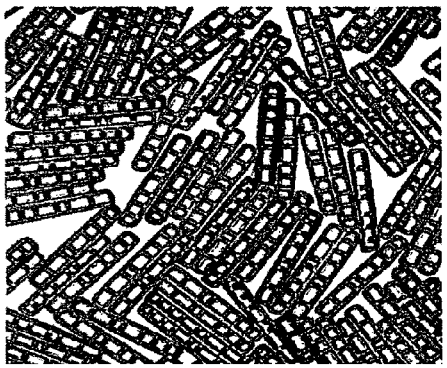
Figure 46D:
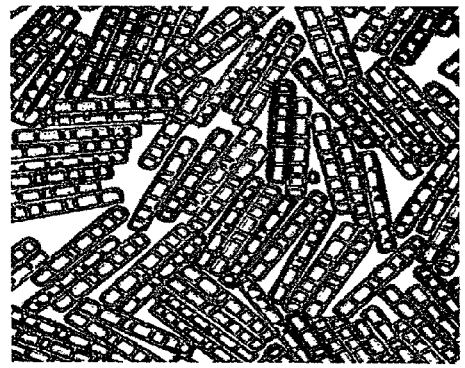
Figure 46E:
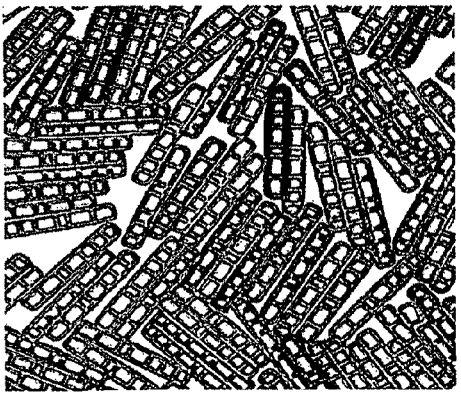
Figure 46F:
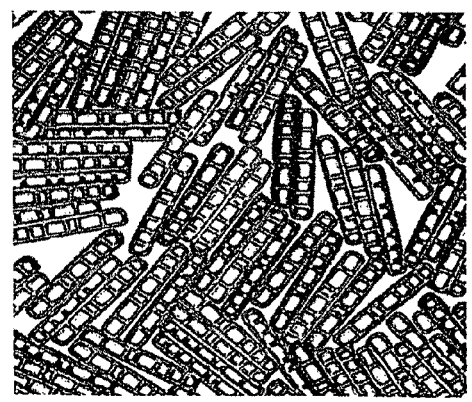

FIGS. 45a and 45b show a reflectance and fluorescence image pair for the same set of microparticles of the invention. The images were taken in succession by about 1 second apart. FIG. 45a, the reflectance image was taken with blue light illumination and collection (excitation filter=436/10 nm, emission filter=457/50, i.e. overlapping filters). This image is used to determine the code of each particle. FIG. 45b, the fluorescence image, was taken with green illumination and red collection (excitation filter=555/28 nm, emission filter=617/73, i.e. filters for Cy3). FIG. 45c the image pair of FIGS. 45a and 45b overlaid on top of one another in a single image.

FIGS. 46a to 46f show dense fluorescence microscope images of encoded microparticles in a time sequence. The images have been processed for edge detection. The images were acquired approximately 1 second apart and are frames of the time sequence. The individual particles that comprise the images move a measurable amount between the frames due to molecular collisions (aka Brownian motion). This Brownian motion facilitates the assembly of the particles into a dense 2-dimensional monolayer. The particles shown in the images are examples of biochemically active encoded microparticles. The particles have oligonucleotide probes attached to the surface and have been hybridized (i.e. reacted in solution) with complementary oligonucleotide targets.

The disclosed encoded microparticles can be utilized in a related invention comprised of a compact microscope and imaging technique for identification of barcoded microparticles on diverse backgrounds. The standard identification of encoded microparticles is typically performed in a controlled laboratory setting, such as imaging of particles on a very flat glass surface (such as a glass slide or glass bottom wellplate). In the standard case, the particles (if properly disposed) typically lie in a single focal plane such that all particles in an image field can be accurately identified. An important use of encoded particles is as taggants for material objects and in such applications, the particles are typically not imaged on flat glass. Particles can be placed in a carrier medium, such as a solvent, lacquer, or ink, and applied to a wide diversity of objects. Objects of particular interest include paper, textiles, and metal, plastic, or ceramic surfaces. Particles distributed in or on such objects and surfaces generally do not lie in a single focal plane. Moreover, many particles will individually not be in focus along their entire length. As such, there is a need for encoded particle structures, imaging systems, and image processing algorithms to identify encoded particles on diverse, non-ideal backgrounds.

Addressing these needs, in general in one aspect the present invention includes 1) microparticle structures that are optimized for improved identification on diverse backgrounds, 2) a microscope-based imaging system for imaging encoded microparticles on diverse backgrounds, 3) image processing algorithms to deal with the complexities of particles not lying in a single focal plane. An imaging technique employing #2 and 3 will be described.

Embodiments of the encoded microparticle structures can be high contrast particles that comprise opaque, discrete regions that are surrounded by another typically transparent material. The opaque regions are lineally disposed to form a code. The high contrast comes from the difference in reflected signal between the opaque regions (a.k.a. the segments) and the gaps between those regions. When imaged in reflection mode, as would typically be the case for non transparent background surfaces, the segments are bright white against the background. The outer surface of the particles can be made fluorescent, either by attachment of fluorescent molecules or through the internal incorporation of fluorophores into the outer surface (similar approaches may be used for luminescent or other light emitting materials). In that case, the code appears in the image as a series of bright lines positioned at the cuts. The bright lines will appear enhanced (brighter) if the particle structures have surface topology (i.e. indentations). Particles with no surface topology still exhibit the bright lines and therefore exhibit the code, because the fluorescence emission occurs in all directions and such emission from fluorophores disposed behind the segments (with respect to the optical path/incident illumination direction) is blocked by the segments. In the gap between segments, such emission reaches the collection optics because it is not blocked by the segments.

An example of a compact, portable, inexpensive microscope based imaging system includes a light source, CCD camera, beam splitter, objective, and particles disposed in or on a surface. The CCD camera is used for digital image acquisition by a computer. The microscope imaging system is configured such that it can capture a series of images at different focal planes. An example of an image series is a set of 110 or more images at focal planes that vary by about 100 nm to 500 nm. One purpose of acquiring a series of images is to allow for the variation in z heights (and equivalently focal planes). The focal point of the system may be changed in several ways, including but not limited to approaches such as moving the objective in a housing, varying an optical element such as an electro-acoustic element to change the focal plane, or moving the stage on which the specimen (surface comprising particles) is disposed with respect to the microscope. Combinations of these as well as other microscope setups known in the art can be used to provide images for analysis.

Image analysis software processes the images in a series. For example, the images in a series may undergo algorithmic processing to identify particles and determine codes. In a reflectance mode image, the signature of a particle is discrete segments whose centroids lie along a straight line. Each image is first thresholded to discriminate the segments from the background. Then the thresholded objects undergo an area filter to discriminate segments from other objects. Additionally, this filter may optionally include perimeter criteria. Once the segments are found, their centroids can be determined, then the centroids of neighboring segments can be compared to determine if they fall along a straight line to within an empirically determined tolerance. This determines whether the segments belong to the same particle. Since typically all particles are of a fixed length, the segments that make up a complete particle can be determined with high confidence. A single image can have multiple thresholds applied in the first step, and the particle finding algorithms can be applied to each thresholded "subimage". In this way, variations in background intensity can be overcome and accurate identification of particles accomplished. Processing of fluorescent images proceeds in a similar manner with thresholding first followed by pattern recognition steps to identify the signatures of particles. Fluorescent images comprise a bright outline of the particle with bright bars bisecting the length at positions that determine the code. The utilization of a series of images taken at different focal planes, along with thresholding each individual image of the series at multiple levels, combined with the high manufacturing precision of the encoded microparticles, provided for a complete system for identification of the particles and their codes on diverse backgrounds. The microscope-based imaging system can be configured to take many images at different x and y positions, i.e. to scan an area larger than the image field of view, and thereby acquire more information.

Another related aspect of the invention using encoded microparticles is a parallel microfluidic microbarcode reader. This aspect includes a microfluidic flow based device to read the codes and associated signal (for example fluorescence from a bioassay) of encoded microparticles. The device has many flow channels to enable the simultaneous measurement of many particles, and thus achieve very high throughput analysis. A larger inlet channel splits into many smaller flow channels, each of which has an interrogation point. The width of the flow channels may be 2 to 20 microns. In one embodiment, each interrogation point comprises a light source and a detector. Alternately, a global collimated light source may be used for all channels. The light source and detector may be disposed on opposite sides of the channel or the same side depending on what detection mode is to be utilized (i.e. reflection, transmission, or fluorescence). In another embodiment, the light sources and detectors are integrated into the microfluidic device. Stated another way, the light sources and detectors are placed "on chip", thus providing a compact, portable device. In yet another embodiment, an assembly is provided that comprises many light sources and detectors, and the microfluidic device with the channels is mated to the assembly. This embodiment has an advantage of allowing the microfluidic ship, which comes into direct contact with the particles and potentially a biological sample, to be disposable. Each interrogation point may comprise additional elements, for example, a microlens to focus the light source, which again may be global to all channels or individual for each channel. An example of a detector is a photodiode. Examples of light sources are light emitting diodes, semiconductor lasers, and lamps (such as arc or halogen lamps).

A Bioassay Process Using the Microparticles

The microparticles of the invention can be used as major functional members of biochemical (or chemical) analysis systems, including but not limited to solution based arrays, biochips, DNA microarrays, protein microarrays, lab-on-a-chip systems, lateral flow devices (immunochromatographic test strips) and in vitro diagnostic test strips. Applications include but are not limited to gDNA and protein sequencing, gene expression profiling, genotyping including SNP genotyping, polymorphism analysis, comparative genomic hybridization (CGH), microRNA profiling, chromatin immunoprecipitation (CHiP), methylation detection, as well as discovering disease mechanisms, studying gene function, investigating biological pathways, and a variety of other biochemical, biomolecular, biomedical and medical related applications such as inspection and analyses of proteins, peptides, polypeptide, and related biochemical applications, and the diagnosis and monitoring of medical conditions. Assay architectures may include those well known in the art, including but not limited to direct DNA hybridization, hybridization of DNA to RNA or RNA to RNA, enzymatic assays such as polymerase extension, ligation. The microparticles can also be used in microfluidic or lab-on-a-chip systems or any flow based systems, including but not limited to those systems wherein sample preparation, biochemical reaction, and bioanalyses are integrated.

For example, fluorescent tags can be employed when an optical imaging method based on the presence of fluorescence can be used. Radioactive labels can be used when the microparticles are utilized to expose or develop relevant photographic films. Alternatively, enzymatic tags can be used when the detection involves detection of the product of the enzyme tag that is released when the sample molecules bind to or react with the probe molecules on the microparticles. Other tagging methods are also possible, as set forth in "Quantitative monitoring of gene expression patterns with a complementary DNA microarray" by Schena et al. Science, 1995, 270-467, the subject matter of which is incorporated herein by reference in its entirety.

Samples without labels can also be reacted with the microparticles. For example, molecular beacon probes can be applied to the microparticle. Molecular beacon probes typically contains a hairpin structure that, upon binding the labelless, or in some examples labeled, sample molecules, unfold, thus producing a signal indicative of the binding events. Such molecular beacon probes, as well as other probes, may be used in assays involving FRET (Fluorescence Resonant Energy Transfer), where for example fluorophores or quenchers are placed on or in the surface of the microparticles.

Figure 47:
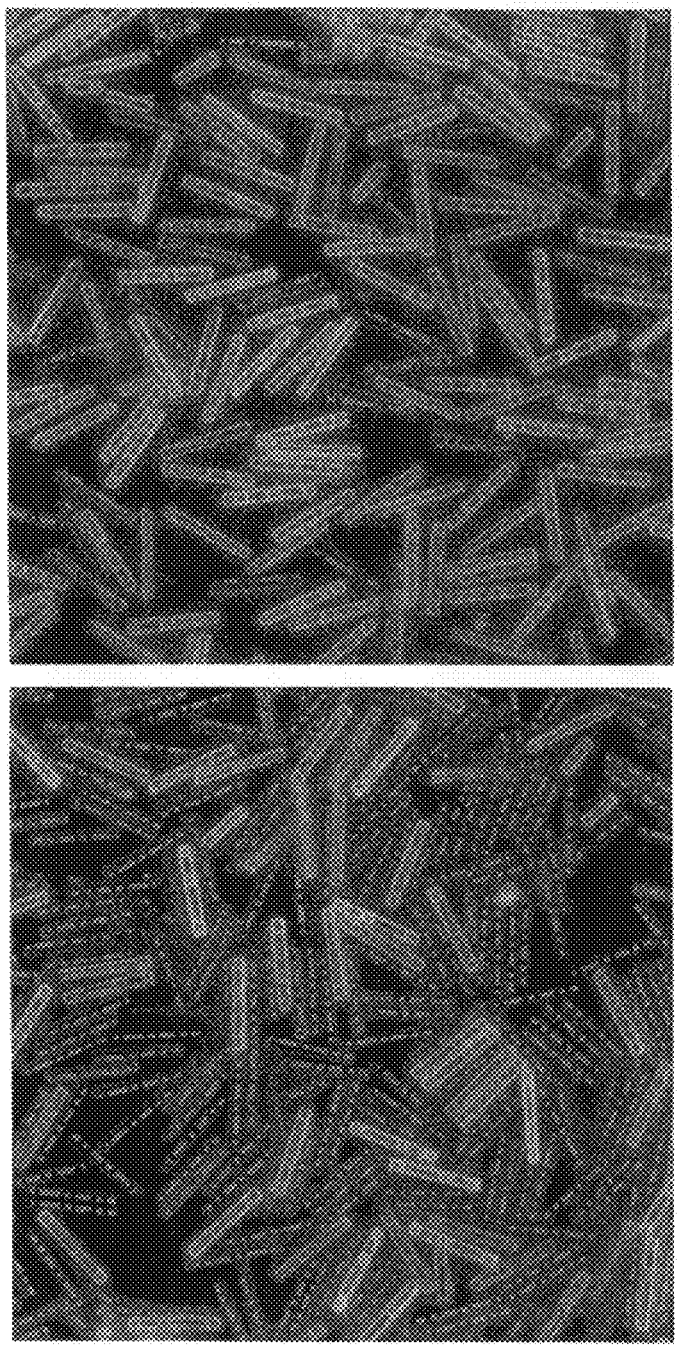
FIG. 47 shows real assay data from a 2-plex DNA hybridization assay (from top to bottom, SEQ ID NOS: 1-4)

FIG. 47 shows real assay data from a 2-plex DNA hybridization assay. In this experiment, 2 different oligo probes (with 2 different sequences shown at the bottom) were attached to the surface of the different particle batches (with different codes). After probe attachment, the particles were mixed together and aliquots of the mixture were placed into two wells of a wellplate. Targets composed of oligos with sequences complementary to the probe sequences and fluorophore labels were then added to the two wells and reacted with the mixture of particle-probe conjugates. Target1, complementary to probe1, was added to the first well and target2, complementary to probe2, was added to the second well. Imaging of the particles of both wells was performed and the results are shown in FIG. 47. In the first well (with target1), particles of the corresponding code exhibit a relatively high fluorescence signal, and vice-versa for the second well.

For facilitating fast, reliable, and efficient bioassay for large number of sample molecules, it is preferred that the microparticles are capable of arranging themselves substantially in a monolayer on a surface, such as the bottom surface of the well in which the microparticles are contained. The microparticles are preferred to be able to undergo Brownian motion in the specific liquid in which the optical detection is performed. Given the specific liquid in which the microparticles are hybridized and detected, it is preferred that the 2D diffusion coefficient of the microparticles is equal to or greater than $1 \times 10^{-12}$ cm$^2$/s and/or 10% or more, such as 15% or more, or even 20% or more, and 50% or more of the microparticles are measured to undergo a lateral displacement of 20 nm or greater, such as 30 nm or greater, or even 50 nm or greater—in a time interval of 1 second or less, or preferably 3 seconds or less, or five seconds or less.

The detectable microparticles, which are referred to as those that are able to be accurately detected by the desired detection means, such as optical imaging using visible light, are capable of occupying 30% or more, 40% or more, and typically 50% or more of the surface area on which the microparticles are collected together, such as a portion of the bottom surface of the container in which the microparticles are contained. Defining an area in which at least 90% of all the microparticles are disposed (typically at least 95% or more typically at least 99%, and often 100%), the microparticles can be seen to have a density of 1000 particles/mm$^2$ or more, such as 1500 particles/mm$^2$ or more, 2000 particles/mm$^2$ or more, and typically 3000 particles/mm$^2$ or more (e.g. 5000 particles/mm$^2$ or more). The detection rate within the above-mentioned area, which rate is defined as the ratio of the total number of detected microparticles (microparticles with spatial codes detected) of a collection of microparticles under detection to the total number of the collection of microparticles, is preferably 80% or more, typically 90% or more, or more typically 99% or more.

Another preferred example of the invention is a kit comprising biochemically active encoded microparticles that contains 200 or more, more preferably 500 or more, 1000 or more, or even 10,000 or more different codes within the kit (due to the large codespace enabled by the invention, even larger numbers of codes.) Due to statistical sample requirements of convenient liquid pipetting and a desired redundancy of particular codes within the kit, more than 10 particles of the same code are typically provided (20 or more, or even 30 or more microparticles of the same code) within the kit, as in some example applications the redundancy improves the overall assay performance. The term "biochemically active encoded microparticles" is refers to microparticles that have biological or chemical moieties on surfaces and thus can be used in assays; and the term "moieties" are referred to as molecular species; including but are not limited to nucleic acids, synthetic nucleic acids, oligonucleotides, single stranded nucleic acids, double stranded nucleic acids, proteins, polypeptides, antibodies, antigens, enzymes, receptors, ligands, and drug molecules, cells, and complex biologically derived samples.

The kit may optionally contain one or more of the following: one or more labels that can be incorporated into a biological moiety; and one or more substrates which may or may not contain an array, etc.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target biomolecules or biomolecules associated therewith.

Figure 52:
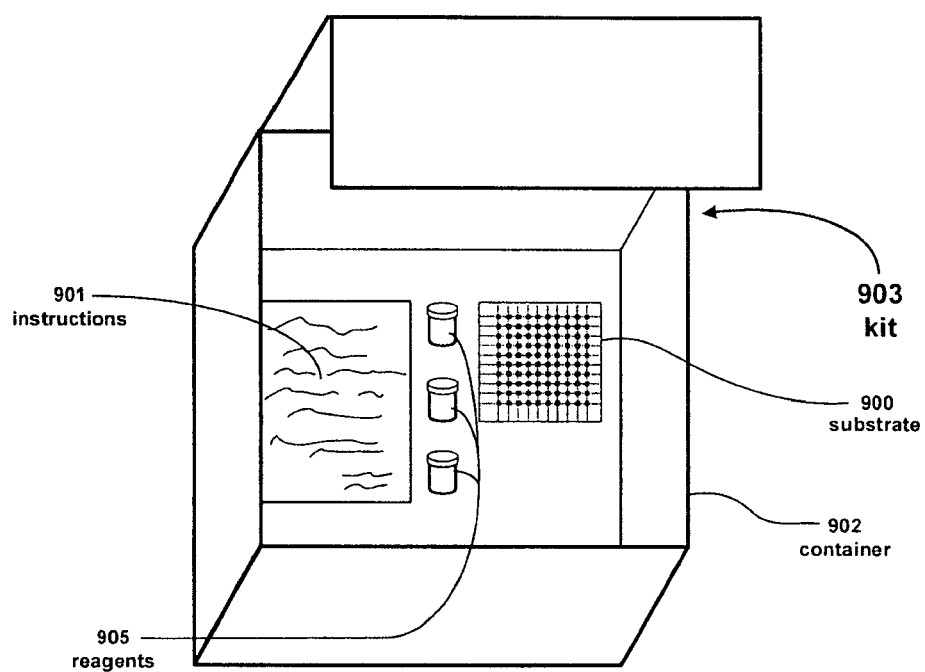
FIG. 52 is a block diagram showing a representative example of a kit.

As described herein and shown in FIG. 52, in certain embodiments a kit 903 can include a container or housing 902 for housing various components. As shown in FIG. 52, and described herein, in one embodiment a kit 903 comprising reagents 905 including but not limited to biochemically active encoded microparticles, and optionally a substrate 900 is provided. As shown in FIG. 52, and described herein, the kit 903 can optionally include instructions 901. Other embodiments of the kit 903 are envisioned wherein the components include various additional features described herein.

Figure 48A:
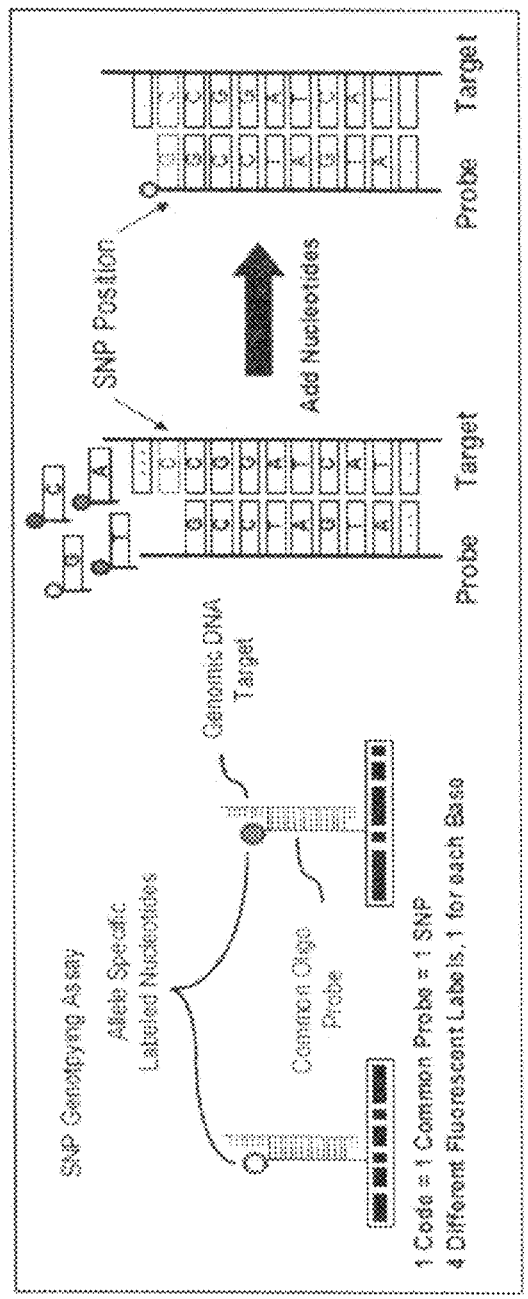
FIG. 48a illustrates an exemplary assay in which the microparticles of the invention can be used.
Figure 48B:
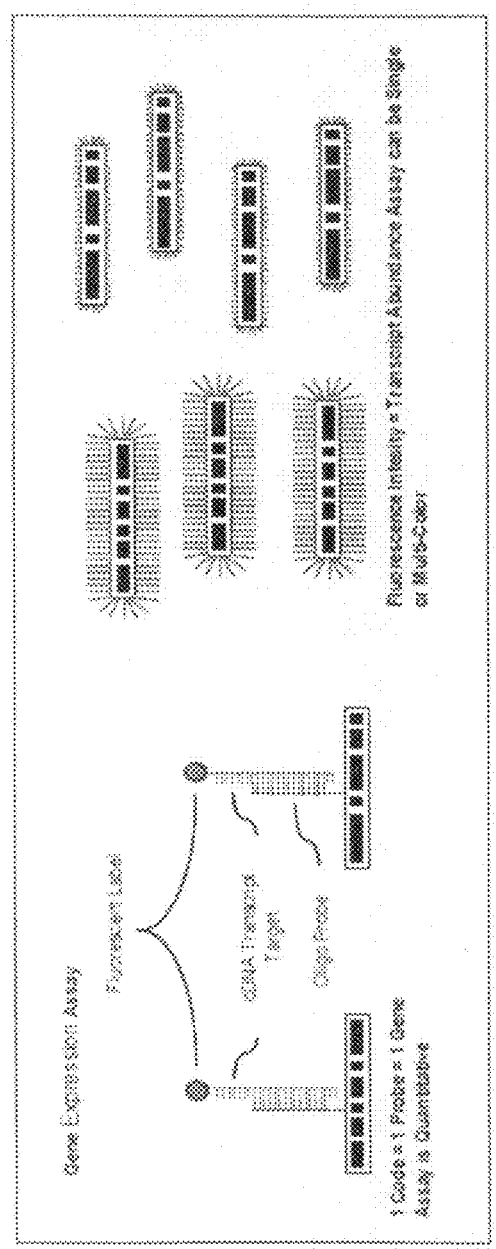
FIG. 48b illustrates another exemplary assay in which the microparticles of the invention can be used.

Universal adapter schemes may be used to provide a set of non-interacting synthetic sequences that are complementary to sequences provided on the probes. Genotyping can be performed using common probes and allele specific reporters or allele specific probes and common reporters. Amplification assays such as those involving PCR, padlock probes, or Molecular Inversion Probes can be performed using the particles of the current invention. Examples of two of these assays are shown in FIGS. 48a and 48b.

In a particular embodiment, "tag" sequences are attached to the particle surface. An "anti-tag" sequence and probe specific sequence are combined as a single sequence that is reacted with the sample. The tag and anti-tag sequences are perfectly (or substantially) complementary. After reaction with the sample, the probe+anti-tag/sample molecule complexes are further reacted with the tag covered particles. The tag and anti-tag sequences hybridize specifically, thus the assay can be read out on the particles. In this particular embodiment, the flow of information goes: sample sequence>probe sequence>anti-tag sequence>tag sequence>particle code.

In an alternative example of the invention, biomolecules that are present on the surface of the particles can be pre-synthesized and then attached to the particle surface. Alternatively, biomolecules can be in situ synthesized on the particles.

Figure 49:
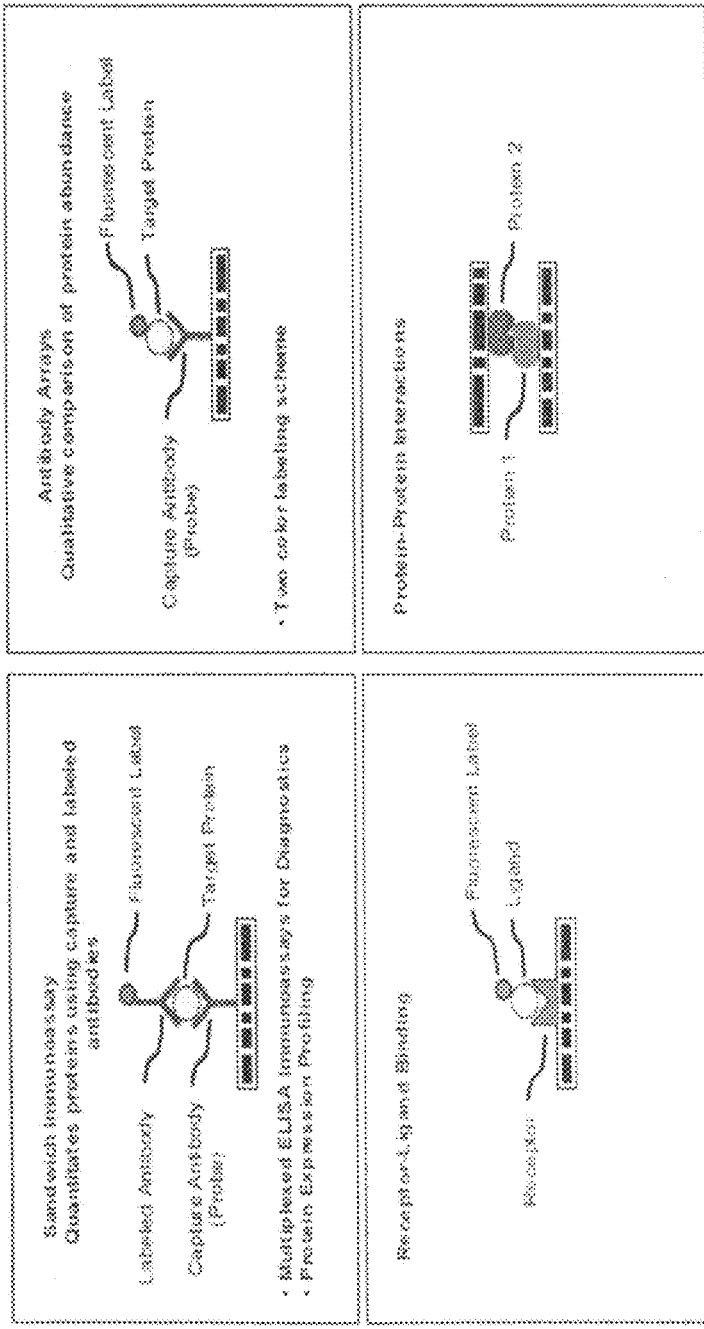
FIG. 49 illustrates another exemplary assay in which the microparticles of the invention can be used.

Protein based assays are also applicable. These include but are not limited to sandwich immunoassays (see e.g., FIG. 49 top left panel), antibody-protein binding assays (see e.g., FIG. 49 top right panel), receptor-ligand binding assays (see e.g., FIG. 49 bottom right panel), or protein-protein interaction assays (see e.g., FIG. 49 bottom right panel). The sets of encoded microparticles of the present invention can be used in solution based assays to investigate protein-protein interactions as illustrated in FIG. 49 bottom right panel. In one embodiment a first protein and a second protein are provided wherein each is associated with a differently encoded particle of the invention. Detection of an interaction between the proteins can be evidenced by detection of the proximity of both particles (e.g., after a washing step to remove non-interacted particles). Accordingly, it is envisioned that a dimer of two differently encoded particles can be formed upon interaction between a first and second protein. In some embodiments more than two proteins interacting can be detected (not shown). For example, where three or more proteins can interact to form a complex of interest, it is envisioned that two or more of the proteins can be associated with particles of the invention (either differently encoded particles, similarly encoded particles or a combination thereof as desired). In some embodiments three or more proteins are associated with differently (or the same or a combination of different and same as desired) encoded particles for use in protein-protein interaction detection.

Using the particles of the invention, it is possible to analyze N2 (i.e., N×N) protein-protein interactions. It is envisioned that protein-protein interactions can be detected for in the presence and/or absence of certain drugs or other compounds. Advantageously, numerous compounds or drugs can be screened using a multiple-well format and the particles of the invention as described herein.

A single type of protein can be applied to microparticles of a single code. Upon mixing of the particle-protein conjugates and reaction in a particular biochemical environment, proteins that interact and bind to one another are determined by the presence of adjacent particles during detection. The square cross section of the microparticle structures of the present invention provide an improvement over the prior art by providing an increased area of contact in the shape of a flat, rectangular surface. Prior art particles that are spherical or cylindrical in shape limit the contact areas to single points or lines respectively. This invention is not limited to proteins: any interacting molecules may be used with this assay architecture. Also, the omni-directional encoded microparticles of the present invention may be used in conjunction with any other encoded particles including but not limited to fluorophores, quantum dots, latex or glass beads, colloidal metal particles, spectroscopically active particles, SERS particles, or semiconductor nanorods.

The encoded microparticles may be used in conjunction with a 2D planar array of molecules. Interaction between molecules on the surface of the particles and those contained in spots on the 2D planar array are determined by the binding of the particles to the spots. The presence of the particles in the predetermined spot locations, preferably after washing steps, indicates a binding interaction between the molecules on the particles and the molecules on the 2D planar array. The assay result can be determined by identifying 1) the particle code, and 2) the spot location. This is shown in FIG. 50. FIG. 50 is a schematic that includes images of particles but is not the result of an actual experiment, i.e. meant to serve as an illustration of this invention. In this invention, the square cross section of the microparticles of the present invention provide for increased binding contact area and is a significant improvement over the prior art.

The microparticles of the invention may have other applications. For example, by placing protein-detection molecules (e.g., ligands, dyes which change color, fluoresce, or cause electronic signal upon contact with specific protein molecules) onto the microparticles, bioassay analyses can be performed (i.e., evaluation of the protein and/or gene expression levels in a biological sample). As another example, by placing (cellular) receptors, nucleic acids/probes, oligonucleotides, adhesion molecules, messenger RNA (specific to which gene is "turned on" in a given disease state), cDNA (complementary to mRNA coded-for by each gene that is "turned on"), oligosaccharides & other relevant carbohydrate molecules, or cells (indicating which cellular pathway is "turned on", etc.) onto the microparticles, the microparticles can be used to screen for proteins or other chemical compounds that act against a disease (i.e., therapeutic target); as indicated by (the relevant component from biological sample) adhesion or hybridization to specific spot (location) on the microarray where a specific (target molecule) was earlier placed/attached. In fact, the microparticles of the invention can be applied to many other biochemical or biomolecular fields, such as those set forth in the appendix attached herewith, the subject matter of each is incorporated herein by reference.

In practicing the methods of the present invention, many conventional techniques in molecular biology are optionally utilized. These techniques are well known and are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5th Ed., John Wiley & Sons, Inc. (2002), Sambrook et al., Molecular Cloning: A Laboratory Manual, 3rd Ed., Cold Spring Harbor Laboratory Press (2000), and Innis et al. (Eds.) PCR Protocols: A Guide to Methods and Applications, Elsevier Science & Technology Books (1990), all of which are incorporated herein by reference.

Sample preparation suitable for use with the system and methods described herein can include any of a number of well know methods for collection and analysis of biological and/or environmental samples. In the case of biological samples, the sample can be, for example, manipulated, treated, or extracted to any desired level of purity for a target of interest.

The sample can be bodily fluids suspected to contain a biologically active analyte. Commonly employed bodily fluids include but are not limited to blood, serum, plasma, saliva, sputum, urine, gastric and digestive fluid, tears, stool, semen, and amniotic, cerebrospinal, lymphatic, and vaginal, fluids. Additionally, disease associated fluids such as peritoneal ascites, effusion from pericardial, peripancreatic, peripleural and other organ sources, fluids associated with implants and abscesses, interstitial fluids derived from tumorous tissue, and aspirants from tumor and organ sources can be examined. Organ or tissue surfaces can be rinsed, as can organ ducts, such as mammary ducts with the resulting rinses analyzed. Surgical and biopsy specimens, including single needle biopsy samples, can be mechanically homogenized, or lysed with enzymes or other chemical reagents and the resulting solutions analyzed.

It is anticipated that the systems described herein can be used for screening a large variety of samples. In the case where the investigated subject is a living creature, the sample may originate from body fluids as discussed. Methods of obtaining samples include but are not limited to cheek swabbing, nose swabbing, rectal swabbing, skin fat extraction or other collection strategies for obtaining a biological or chemical substance. For fetal genetic testing, besides the genetic analysis of samples removed by amniocentesis, the chorionic villi can also be sampled. Developing embryos produced by in vitro fertilization can have one or two blastomeres removed for sampling.

When the tested subject is a non-living or environmental body, the sample may originate from any substance in a solid phase, liquid phase or gaseous phase. The sample may be collected and placed onto the sensing substrate or the sensing substrate may be directly exposed to the investigated sample source (e.g. water reservoir, free air) and interact with it.

In some embodiments, the bodily fluids are used directly for detecting one or more biologically active analyte present therein with the subject microparticle invention without further processing. Examples include in vitro diagnostic test strips for use with urine. Where desired, however, the bodily fluids can be pre-treated before performing the analysis with the subject microparticle invention. The choice of pre-treatments will depend on the type of bodily fluid used and/or the nature of the biologically active analyte under investigation. For instance, where the biologically active analyte is present at low level in a sample of bodily fluid, the sample can be concentrated via any conventional means to enrich the biologically active analyte. Methods of concentrating a biologically active analyte include but are not limited to drying, evaporation, centrifugation, sedimentation, precipitation, and amplification. Where the biologically active analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the biologically active analyte is a molecule present on or within a cell, extraction can be performed using lysing agents including but not limited to denaturing detergent such as SDS or non-denaturing detergent such as thesit (2-dodecoxyethanol), sodium deoxylate, Triton® X-100, and Tween® 20.

In some embodiments, pretreatment can include diluting and/or mixing the sample, and filtering the sample to remove, e.g., red blood cells from a blood sample. In other embodiments, pretreatment can include dialysis to remove contaminants, to exchange buffers, or to concentrate the sample.

Targets detectable using the microparticles include but are not limited to, a biologically active analyte including a nucleic acid, a protein, an antigen, an allergen, an antibody, an antibody fragment, an aptamer, a phage display, a microorganism, a gas, a chemical agent and a pollutant. Other detectable targets include biotin, avidin and streptavidin.

In one embodiment, the target is a nucleic acid that is DNA, for example, cDNA. In a related embodiment, the DNA target is produced via an amplification reaction, for example, by polymerase chain reaction (PCR). In another embodiment of the subject invention, the detected biologically active analyte is a protein representing a known bio-marker for a disease or specific condition of the investigated organism. In another embodiment several different biologically active analytes can be proteins provided as a panel of bio-markers wherein relative concentrations of the bio-markers are indicative for a disease or other condition of the investigated organism. In a further embodiment the target is a microorganism that is a pathogen. In another embodiment the target is a chemical agent, for example, a toxic chemical agent.

Where the target is a nucleic acid, it can be single-stranded, double-stranded, or higher order, and can be linear or circular. Exemplary single-stranded target nucleic acids include mRNA, rRNA, tRNA, hnRNA, ssRNA or ssDNA viral genomes, although these nucleic acids may contain internally complementary sequences and significant secondary structure. Exemplary double-stranded target nucleic acids include genomic DNA, mitochondrial DNA, chloroplast DNA, dsRNA or dsDNA viral genomes, plasmids, phage, and viroids. The target nucleic acid can be prepared synthetically or purified from a biological source. The target nucleic acid may be purified to remove or diminish one or more undesired components of the sample or to concentrate the target nucleic acids. Conversely, where the target nucleic acid is too concentrated for the particular assay, the target nucleic acid may be diluted.

Following sample collection and optional nucleic acid extraction, the nucleic acid portion of the sample comprising the target nucleic acid can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target nucleic acid. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target nucleic acid is single-stranded, the first cycle of amplification forms a primer extension product complementary to the target nucleic acid. If the target nucleic acid is single stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target nucleic acid can be amplified by contacting one or more strands of the target nucleic acid with a primer and a polymerase having suitable activity to extend the primer and copy the target nucleic acid to produce a full length complementary nucleic acid or a smaller portion thereof. Any enzyme having a polymerase activity that can copy the target nucleic acid can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenaseo® Version 2.0 T7, Tub, Taq, Tth, Pfx, Pfu, Tsp, Tfl, Tli and *Pyrococcus* sp GB D DNA polymerases; RNA polymerases such as *E. coli*, SP6, T3 and T7 RNA polymerases; and reverse transcriptases such as AMV, M MuLV, MMLV, RNAse H' MMLV (Superscript®), Superscript® II, ThermoScript®, HIV 1, and RAV2 reverse transcriptases. All of these enzymes are commercially available. Exemplary polymerases with multiple specificities include RAV2 and Tli (exo) polymerases. Exemplary thermostable polymerases include Tub, Taq, Tth, Pfx, Pfu, Tsp, Tfl, Tli and *Pyrococcus* sp. GB D DNA polymerases.

Suitable reaction conditions are chosen to permit amplification of the target nucleic acid, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot start techniques, use of nested primers, or designing PCR primers so that they form stem-loop structures in the event of primer-dimer formation and thus are not amplified. Techniques to accelerate PCR can be used, for example, centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target nucleic acids or different regions of a particular target nucleic acid within the sample.

Amplified target nucleic acids may be subjected to post amplification treatments. For example, in some cases, it may be desirable to fragment the target nucleic acid prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow a nucleic acid associated with the optical sensing site to hybridize to the amplification product during at least part of an amplification cycle. When the assay is performed in this manner, real time detection of this hybridization event can take place by monitoring for light emission during amplification.

Real time PCR product analysis (and related real time reverse-transcription PCR) provides a well-known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" Clin Chem 45(7):982-6; Bièche et al. (1999) "Quantitation of MYC gene expression in sporadic breast tumors with a real-time reverse transcription-PCR assay" Cancer Res 59(12):2759-65; and Kreuzer et al. (1999) "LightCycler technology for the quantitation of bcr/abl fusion transcripts" Cancer Res 59(13):3171-4, all of which are incorporated by reference). In addition, linear PCR and Linear-After-The Exponential (LATE)-PCR can be adapted for use with the methods described herein.

Immunoassays are another form of analysis that can be conducted using the microparticles of the invention. Suitable immunoassay systems include but are not limited to competitive and non-competitive assay systems. Such assay systems are typically used with techniques such as western blots, radioimmunoassays, EIA (enzyme immunoassay), ELISA (enzyme-linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and cellular immunostaining (fixed or native) assays to name but a few. Such assays are routine and well known in the art (see, e.g., Ausubel et al., supra). Immunoassay techniques particularly useful with the microparticle systems described herein include but are not limited to ELISA, "sandwich" immunoassays, and fluorescent immunoassays. Exemplary immunoassays are described briefly below (but are not intended by way of limitation).

ELISAs generally involve preparing antigen, coating a substrate (e.g., an encoded microparticle) with the antigen, adding the antibody of interest conjugated to a detectable compound such as an enzymatic substrate (e.g., horseradish peroxidase or alkaline phosphatase) to the substrate and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the substrate. Further, instead of coating the substrate with the antigen, the antibody may be coated to the substrate. In this case, a second antibody conjugated to a detectable compound may be added following the addition of the antigen of interest to the coated substrate. One of skill in the art would be knowledgeable as to the parameters that can be modified to increase the signal detected as well as other variations of ELISAs known in the art.

In one exemplary immunoassay, a sample contains an unknown amount of biologically active analyte to be measured, which may be, for example, a protein. The analyte may also be termed an antigen. The sample may be spiked with a known or fixed amount of labeled analyte. The spiked sample is then incubated with an antibody that binds to the analyte, so that the analyte in the sample and the labeled analyte added to the sample compete for binding to the available antibody binding sites. More or less of the labeled analyte will be able to bind to the antibody binding sites, depending on the relative concentration of the unlabeled analyte present in the sample. Accordingly, when the amount of labeled analyte bound to the antibody is measured, it is inversely proportional to the amount of unlabeled analyte in the sample. The amount of analyte in the original sample may then be calculated based on the amount of labeled analyte measured, using standard techniques in the art.

In one exemplary competitive immunoassay, an antibody that binds to a biologically active analyte may be coupled with or conjugated with a ligand, wherein the ligand binds to an additional antibody added to the sample being tested. One example of such a ligand includes fluorescein. The additional antibody may be bound to a solid support (e.g., an encoded microparticle). The additional antibody binds to the ligand coupled with the antibody that binds in turn to the analyte or alternatively to the labeled analyte, forming a mass complex which allows isolation and measurement of the signal generated by the label coupled with the labeled analyte.

In another type of exemplary competitive immunoassay, the biologically active analyte to be measured may be bound to a solid support (e.g., an encoded microparticle), and incubated with both an antibody that binds to the analyte and a sample containing the analyte to be measured. The antibody binds to either the analyte bound to the solid support or to the analyte in the sample, in relative proportions depending on the concentration of the analyte in the sample. The antibody that binds to the analyte bound to the solid support is then bound to another antibody, such as anti-mouse IgG, that is coupled with a label. The amount of signal generated from the label is then detected to measure the amount of antibody that bound to the analyte bound to the solid support. Such a measurement will be inversely proportional to the amount of analyte present in the sample. Such an assay may be used with the encoded microparticles of the present invention.

In another type of exemplary competitive immunoassay, the biologically active analyte to be measured may be bound to a solid support (e.g., an encoded microparticle), and incubated with both an antibody that binds to the analyte and a sample containing the analyte to be measured. The antibody binds to either the analyte bound to the solid support or to the analyte in the sample, in relative proportions depending on the concentration of the analyte in the sample. The antibody that binds to the analyte bound to the solid support is then bound to another antibody, such as anti-mouse IgG, that is coupled with a label. The amount of signal generated from the label is then detected to measure the amount of antibody that bound to the analyte bound to the solid support. Such a measurement will be inversely proportional to the amount of analyte present in the sample. Such an assay may be used with the encoded microparticles of the present invention.

In an exemplary assay scheme, an encoded microparticle bioassay is performed by dividing a reaction into two or more sub-reactions. The assay starts with a mixture of conjugated encoded microparticles (conjugates for short) disposed in a liquid. Each conjugate type comprises a code and a corresponding analyte specific probe. The mixture of conjugates is subjected to a first reaction with a first reactant, for example with a complex sample. In the first reaction, interactions occur between the conjugates and the first reactant which will be subsequently detected. After the first reaction, the total volume of the liquid is split into two or more sub-reactions. In one example, the splitting is accomplished with standard pipetting with the resulting sub-reactions comprising all conjugate types present (i.e. all codes). The volumes may be chosen to be equal, whereby each sub-reaction thus contains approximately equal fractions of the conjugates from the first reaction, within the expected random fluctuations governed by Poisson statistics. The volumes may be chosen to be unequal to account for differences in the individual sub-reactions. More than 100 codes may be utilized and split into two or more sub-reactions. More than 400 codes may be utilized and split into 3 or more reactions. Encoded particles with spatial codes, having a size less than 50 microns in the longest dimension, may be utilized in two or more sub-reactions. Particles with a glass outer surface and flat sides may also be used in two or more sub-reactions.

An example of a bioassay comprising encoded microparticles (particles for short) in a liquid array that may be split into sub-reactions is a sandwich immunoassay. In a sandwich immunoassay, capture agents are bound to the particles. Examples of capture agents include but are not limited to antibodies, antibody fragments, and aptamers. A mixture of particles comprising different codes, each with a corresponding capture agent, comprise the liquid array. Some codes may be provided without capture agents as controls. The mixture of particles is reacted with a sample comprising a mixture of analytes, that for example may be a plasma or serum sample. The capture agents on the particles bind their corresponding analytes, which thus become captured analytes. Ideally, each capture agent would bind only it's corresponding analyte and no other to a measurable degree. Practically, there is some degree of cross binding between capture agents and analytes other than the corresponding ones. After reaction with the sample, unbound analytes are washed away.

The next step of the sandwich immunoassay comprises providing detection agents. Example detection agents include but are not limited to labeled antibodies. The detection agents bind to the captured analytes, ideally with a one-to-one specificity. Again, practically, cross reactivity may be a problem. The cross reactivity at this stage is between detection agents and other non-corresponding analytes.

The invention provides for the original reaction to be split into sub-reactions which may comprise different subsets of detection agents that are chosen to minimize the cross-reactivity of the bioassay. If certain detection agents are known to bind to other analytes, in addition to the corresponding analyte (i.e. the target analyte), those so called cross-reacting detection agents are separated and placed into different sub-reactions from the detection agents that are directly targeted for the other analytes. For example, let A1, A2, A3, . . . An represent different analytes, and D1, D2, D3, . . . Dn represent the corresponding detection agents (i.e. detection agent D1 is targeted for analyte A1). If Di is found to have cross reactivity for Aj, then Di and Dj would be placed into separate sub-reactions. The signal on analyte Aj is then measured with the sub-reaction containing Dj.

A wide diversity of labels are available in the art that can be employed for conducting the subject assays. In some embodiments labels are detectable by spectroscopic, photochemical, biochemical, immunochemical, or chemical means. For example, useful nucleic acid labels include fluorescent dyes, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include enzymes, substrates, cofactors, inhibitors, fluorescent moieties, chemiluminescent moieties, or bioluminescent labels. Labeling agents optionally include, for example, monoclonal antibodies, polyclonal antibodies, proteins, or other polymers such as affinity matrices, carbohydrates or lipids. Detection proceeds by any of the methods described herein, for example, by detecting an optical signal in an optical waveguide. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Preferred labels include labels that produce an optical signal. Thus, a label includes without limitation any composition detectable by spectroscopic, photochemical, biochemical, immunochemical, electrical, optical, thermal, or chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non-radioactive labels are often attached by indirect means. Generally, a ligand molecule is covalently bound to a polymer. The ligand then binds to an anti-ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a fluorescent label, it may be detected by exciting the fluorochrome with the appropriate wavelength of light and detecting the resulting fluorescence by, for example, fluorescence microscopy. Similarly, enzymatic labels are detected by providing appropriate substrates for the enzyme and detecting the resulting reaction product (e.g., a reaction product capable of producing a detectable optical signal).

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (e.g., light) when they move from an "excited state" to a lower energy state (usually the ground state); this process is often referred to as "radioactive decay". There are many causes of excitation. If the exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin allowed transitions. If photoluminescence is the result of a spin forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

Assays comprising lipids are another type of biochemical analysis that can be conducted using the microparticles of the invention. As described in the literature (Buranda, T. et al. "Biomimetic Molecular Assemblies on Glass and Mesoporous Silica Microbeads for Biotechnology" Langmuir 2003, 19, 1654-1663) microparticles can readily be coated with lipid layers, i.e. lipid bilayers. The lipid layers can host proteins such as membrane receptors for bioassays. An embodiment of the present invention comprises the use of lipid layers with spatially encoded microparticles to achieve multiplexed bioassays, including both the screening of embedded or attached biomolecules and the screening of small molecules, drug compounds, and/or biomolecules that are subsequently released from the lipid bilayer (such molecules may be contained in the interstitial space between the lipid and the particle surface) for interaction with cells or other molecules in miniature reaction vessels (which may be microfabricated and contain picoliter volumes).

The invented microparticle technology offers substantial advantages for lipid applications over both planar approaches, such as Hong, et al. "G-Protein-Coupled Receptor Microarrays for Multiplexed Compound Screening" Journal of Biomolecular Screening 11(4); 2006, and previously utilized microparticles. These advantages include a high code capacity (greater than 100 codes) encoding scheme/structure.

Further advantages include the material surface properties of the particles, i.e. the glass (SiO2) surface is readily modified and functionalized, and is stable and non reactive. The structure of the particles, for example both particles having square and rectangular cross sections, present flat surfaces for optimal imaging and quantitation, as well as for binding to other surfaces.

In a separate embodiment, the present invention provides a method of monitoring one or more pharmacological parameter, for example, pharmacodynamic (PD) and/or pharmacokinetic (PK) parameters, useful for assessing efficacy and/or toxicity of a therapeutic agent. The method comprises subjecting a sample of bodily fluid from a subject administered with the therapeutic agent to a microparticles of the invention for monitoring the one or more pharmacological parameter, the encoded microparticles of the invention can be used as described herein to yield detectable signals indicative of the values of the more than one pharmacological parameter from the sample; and detecting the detectable signal generated from said sample of bodily fluid.

In one implementation the samples tested can include a large number of a variety of small molecules (e.g., screening libraries) which are of interest when investigating new drugs. Accordingly, the microparticle system described herein is useful for screening libraries of small molecules to investigate their ability to interact with certain biologically active analytes may reveal potential new drugs. Further screening of some or all small molecule candidates may reveal adverse drug effects and toxicity. In one implementation the samples can include molecules which are tested for toxicity. In another aspect the invention provides a system for low volume detection of multiple biologically active analytes. The system can include a plurality of spatially coded microparticles wherein the plurality of microparticles include probes and greater than 1,000 spatial codes. It is envisioned that greater than 10,000 spatial codes can be provided in some embodiments. The system can provide for optical detection of spatial codes in a volume less than 50 ul. In one embodiment the spatial codes are optically determined in less than 10 ul. In yet another embodiment the spatial codes are optically determined in less than 5 ul.

In another aspect of the invention, highly multiplexed reactions take place in reaction volumes that are less than 50 ul. In one embodiment, the reaction volume is less than 10 ul and in yet another embodiment the reaction volume is less than 5 ul. In an embodiment, the reaction volumes are contained in reservoirs, such as test tubes or the wells of a microtiter plate. In another embodiment, the reaction volumes are formed at the intersection of microchannels. Those intersections may be addressable and add another dimension to the multiplexing. In another embodiment, the reaction volumes are formed in droplets. The droplets may be produced by injection through an orifice, such as in a microfluidic system, or by an emulsion.

The high multiplex level and small size of the invented particles provide further inventive combinations. In an embodiment, more than 200 different codes, utilized to detect more than 200 different targets, are provided in a reaction volume less than or equal to 50 ul. In another embodiment, more than 500 different codes are provided in less than 50 ul reaction volume. In another embodiment, more than 200 different codes are provided in less than 10 ul reaction volume. In another embodiment, more than 200 different codes are provided in less than 5 ul reaction volume. In another embodiment, more than 500 different codes are provided in less than 10 ul reaction volume. In another embodiment, more than 500 different codes are provided in less than 5 ul reaction volume. In another embodiment, more than 1,000 different codes are provided in less than 50 ul volume. In another embodiment, more than 10,000 different codes are provided in less than 50 ul volume. In another embodiment, more than 1,000 different codes are provided in less than 10 ul volume. In another embodiment, more than 1,000 different codes are provided in less than 5 ul volume. In another embodiment, more than 10,000 different codes are provided in less than 10 ul volume. In another embodiment, more than 10,000 different codes are provided in less than 5 ul volume.

Typically for microparticles used in bioassays, including multiplexed assays using encoded particles, the entire particle surface is derivatized (a.k.a. functionalized) for attachment of the biomolecular probes. This results in the probes coating the entire particle surface. In some assays, it would be an advantage to have a reduced area of probes (i.e. the area available for target binding) in order to increase the sensitivity of the assay. A reduced area increases the sensitivity (or lowers the limit of detection) because the targets, which are typically fluorescently labeled, are concentrated in a smaller area, resulting in a higher signal measured per unit area, for instance with a CCD camera.

In a particular embodiment of the invention, encoded microparticles are provided with reduced surface area for binding. Several embodiments with reduced binding are provided as structures and methods. One way to produce particles with reduced binding areas is to protect the area that ultimately will have probes attached to it (the so called "binding patch"), block the rest of the surface, remove the protection, then proceed with a treatment that will selectively functionalize the biding patch. Another way to produce particles with reduced binding areas is to have an outer layer and inner layer surrounding the particle. The outer layer does not derivatize with the chosen treatment and the inner layer does. These two layers could be two different materials such as silicon nitride for the outer layer and silicon dioxide for the inner layer, or some material that is modified in one of the layers. The outer layer is removed in the binding patch area, revealing the inner layer which is then available for derivatization.

The binding patch can be a small fraction of the particle surface or a large fraction. Preferably, the binding patch is less than 50% of the total particle area, and even more preferably, less than 10%. Preferably, the binding patch is less than 50 square microns, more preferably less than 10 square microns, and even more preferably less than 2 square microns. The patch can be on one face of the particle or extend to multiple faces. The binding patch can be on one end or in the center.

One embodiment of the invented particles has indentations (a.k.a. divits) in one or more faces. The indentations provide regions of increased aerial density of fluorophores and therefore appear brighter than surrounding regions in fluorescence images. In a preferred embodiment comprising reduced binding areas, the patch is located in a indentation region. In an alternate embodiment, it is located in a region without indentions, i.e. a flat region. In yet another embodiment, the particle surface in the binding patch region is further processed to provide a non-flat topology for increased signal, for example by roughening the surface.

A method to produce particles with binding patched that is based on planar processing (i.e. MEMS processing) is as follows: 1) fabricate particles on a wafer surface, 2) apply an additional protect layer over the topmost layer in the particle fabrication process, 3) pattern the protect layer such that it is left remaining only in the binding patch region, 4) release particles from the substrate, 5) perform a block treatment on the particles, 6) remove the protect layer from the patch, 7) perform functionalize treatment which selectively functionalizes the patch.

Another embodiment of the microparticle invention is an improved structure with multiple advanced features to improved performance in binding assays. The first advanced feature is a through-hole binding region. The through-hole region is selectively functionalized to serve as a reduced area for molecular binding. By reduced area, it is meant that the entire outer surface of the particle is not employed in the application of biomolecular probes but instead only a small area is utilized, that small area being a subset of the entire particle surface.

In a preferred embodiment, the through-hole region is comprised of silicon dioxide (glass) and is the only area on the particle surface to be functionalized by the chemical treatment steps that are used to attach probed molecules. A preferred method of accomplishing the selective functionalization is to have the remaining surface (other that the sidewalls of the through-hole) be a different material that does not undergo the same surface chemical modification by the functionalizing step. For example, the sidewalls could be silicon dioxide and the rest of the particle surface could be silicon nitride (or silicon). A method of creating the particle structure such that only the through-hole sidewalls are silicon dioxide is to etch the through-hole through silicon, then oxidize the surface, forming a layer of silicon dioxide on the sidewall.

A second advanced feature of the invented microparticle are shaped edges to assist in the self-orientation of the particle surfaces in a preferred configuration. The microparticle shape is preferred to be flat so that the particles lie on a surface in a particular orientation. In a preferred embodiment, the microparticles have codes and the particular orientations are ones in which the codes can be read. In a preferred embodiment, the particles have a substantially six sided shape and the particular orientations are the two that have the two largest surfaces in contact with the surfaces on which the particles are resting. Said another way, the particles have two largest flat faces from which the code can be read and it is desirable that all of the particles lie in the surface so that those two faces (one or the other) are flat against the surface on which the particle lies. If the particles comes to rest on an edge (defined as the two smaller area faces of the four faces that run along the length of the particle), the shaping of the edges will cause the particles to tend to fall over and lie on one of the two large flat faces. An example of the shaping of the edges is the creation of knife edge profiles.

Another embodiment of the inventions comprises controlling the sensitivity of a solution array by varying the particular number of particular conjugate types. Since the total surface area covered in probe molecules can play a major role in determining the sensitivity of an assay, this surface area can easily be controlled in a solution array based on particles by varying the number of particles of a particular type used in the pooled probe set. In this way, for example, highly expressed genes can be brought into the linear range by using more particles on average compared to other genes, and lowly expressed ones by using less.

The small size, material properties, and low volume detection capability of the invented particles provide for assay reactions to be carried out with small probe surface areas in a particle-based suspension array. In an embodiment, less than 100,000 square microns of probe surface area per target species are input into a suspension array reaction. In another embodiment, less than 10,000 square microns of probe surface area per target species are input into a suspension array reaction.

In embodiments of the invention, the reduced binding area (i.e. the patch) may be a recessed region in one face of the particle or it may be a through hole. Differential binding of biochemical or chemical moieties between the patch and the remainder of the particle surface may be achieved through several different techniques. An example of such a technique is the protection of the patch area (for example by photoresist), subsequent blocking of the remainder surface area to prevent chemical attachment, then removal of the protection layer (or functional groups), followed by further selective functionalization of only the patch area (or direct attachment of probe moieties). In another example, differential attachment is achieved through the use of different materials, such as silicon dioxide and silicon nitride in the patch vs. remainder areas. The microparticle preferably has a chemical or structural code that can be used to identify individual particles among mixtures. The code can be, for example, a spatially varying optical code.

It is envisioned that a variety of instrumentation relating to biological or environmental sample preparation, handling and analysis can be used in conjunction with the devices and methods described herein. Examples of such instrumentation include but are not limited to a cell sorter, a DNA amplification thermal cycler, or a chromatography machine (e.g., GC or HPLC). Such instrumentation is well known to those skilled in the art. It is envisioned that a robotic interface could be used between the encoded microparticles of the present invention and various instrumentation relating to biological or environmental sample preparation, handling and analysis.

Another related invention is a test strip device comprising encoded microparticles. In a proffered embodiment, the encoded microparticles are used to capture an antigen-reporter complex. Encoded microparticle provide a convenient, low cost, and high performance way to achieve a quantitative, high multiplexed test strip (a.k.a. lateral flow strips and related to immunochromatographic devices). In an alternate embodiment, the encoded microparticles can be used as reporters themselves, being captured onto conventional test strip lines of capture agents (like antibodies), also including microsphere capture agents (i.e. "boulders-in-the-stream" approach). A mixture of many different codes of particles, each with a different capture agent, takes the place of a plurality of test lines. The capture agents are inferred from the code on the microparticle (i.e. there is a one-to-one correspondence between code and capture agent species, present as a lookup table that is produced when the capture agents are conjugated to the microparticles). This has the advantage of achieving much higher multiplexing levels than is achievable with multiple test lines. Also, the manufacturing process for producing these highly multiplexed encoded microparticle based test strips is simpler, just involving depositing a single reagent (the mixture of encoded microparticles) onto the test strip. The readout for the encoded microparticle test strip is a microscope, thus a low cost portable reader can be achieved. An example of such a reader is a CCD based microscope system that can be plugged into a laptop computer. Reporters schemes for the encoded microparticle test strip can be chosen from those known in the art and currently used with conventional test strips, such as dyed microspheres, fluorophores, or colloidal gold nanoparticles. In an embodiment, the encoded particle test strip is constructed such that a sample flows into a region containing the mixture of encoded microparticles. This region typically comprises the particles randomly distributed but alternately may be constructed in such a way as to provide order, for example by utilizing groves to align the particles along an axis.

The devices and methods described herein may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis or diagnosis of HIV, as disclosed in U.S. Pat. No. 6,027,880 and U.S. Pat. No. 5,861,242. Genetic mutations may be detected by sequencing, or by hydridization. In one embodiment, genetic markers may be sequenced and mapped using Type-IIs restriction endonucleases as disclosed in U.S. Pat. No. 5,710,000.

In an embodiment of the invention, high throughput sequencing is performed on encoded microparticles. For example, genomic DNA is fragmented and amplified (or enriched) on a set of encoded microparticles. Cyclical sequencing by synthesis (SBS) is performed with the code of an individual microparticle providing the mechanism to link each cycle (and the base information of each cycle) into the sequence read, i.e. the fragments on an individual particle are tracked by the code of that particle. Each cycle of SBS generates a table of codes for individual particles and corresponding base information (sequencing data). Over a million particles can be used in a single run to generate 10's of MB of sequence data. Longer reads and more particles (over 10 million, over 100 million, or over a billion particles) can be used to generate GB's of sequence data very efficiently and cost effectively. The use of encoded microparticles permits high multiplexing of the sequencing process and provides robust and convenient tracking of the reactions. Examples of specific methods and protocols for this invention are list below and in Shendure, J. et al. "Accurate Multiplex Polony Sequencing of an Evolved Bacterial Genome" Science vol. 309. pp. 1728-1732. Sep. 9, 2005.

The genomic DNA (gDNA) fragment amplification can be done using emulsion PCR, where individual particles are prepared in droplets which are generated to contain millions of copies of identical PCR amplicons. The amplicons are captured on the particles such that ideally each particle has a single species (sequence) of amplicon. In practice, some particles are produced with no amplicons (DNA to be sequenced) and some particles with more than one species of amplicon. After emulsion PCR, the so called "clonal" particles (those with a single species of amplicon) can be selected out (i.e. enriched) from the others. After preparation of the fragments to be sequenced on the set of encoded particles, the sequencing itself is performed. The use of encoded particles as compared to non-encoded, blank particles (a.k.a. beads) is very powerful because it allows sequencing reactions to be carried out in standard tubes or wellplates, in very small volumes. Conventional approaches with blank beads utilize complex flow cells and/or immobilization of the beads. One of the primary advantages of this invention is the reduced complexity (and therefore reduced time and cost) of both the instrument for detection and the reaction instrumentation. Also, the small reaction volumes for the sequencing reactions reduces the expense of costly enzymes and speeds up cycle times because of the fast 3 dimensional reaction kinetics of particles in the solution phase. The cycle times are a major limitation of current technologies.

An example sequencing system comprises 1) fragment preparation by emulsion PCR, 2) SBS reaction, for example using a 4-color protocol where the color of the fluorophore reporter indicates the base (which could be greater than 1 base per cycle), 3) detection, for example in a flow cytometer or similar system that may utilize a laser for illumination and photomultiplier tubes for signal quantitation. Steps 2 and 3 are repeated in many cycles to build up the complete sequences. The fragment preparation step, such as emulsion PCR, is done on a set of encoded particles. The set is typically comprised of many (millions or more) particles which all have a unique code, such that individual amplicons have a one-to-one correspondence with a code.

A preferred example of a detection system is a flow cytometer, which can provide very fast readout of the sequencing reactions. These instruments are already widely available. In a flow cytometer, the code of the particles can be read with a detector placed across the point of interrogation from the illumination, i.e. a modified forward scatter detector. There are many advantages of the invented encoded particles discussed above. The codes of the particles may be read in transmission, reflection, or fluorescence mode. In a flow cytometer, the codes will probably be read with the forward scatter channel, but may also be read with the side scatter, one of the fluorescence channels (photomultiplier tubes), or a variation thereof. In another embodiment, massively parallel sequencing of polynucleotides can be conducted as disclosed in Margulies, M., et al., wherein individual particles substitute for the disclosed picoliter reactors contained on an array. Another embodiment employs single base extension reactions as described in Giusto, D, and King, G C. In further embodiments, DNA sequencing by synthesis can be performed such as described by Seo, T S, et al.

Other applications include chip based genotyping, species identification and phenotypic characterization, as described in U.S. Pat. No. 6,228,575. Still other applications including diagnosing a cancerous condition or diagnosing viral, bacterial, and other pathological or nonpathological infections, are described in U.S. Pat. No. 5,800,992. A further application includes chip based single nucleotide polymorphism (SNP) detection as described in U.S. Pat. No. 6,361,947. An additionally application includes solution-based SNP detection with color-coded beads as described in Fujimura et al., Journal of Bioscience and Bioengineering, 94:368-370 (2002).

Gene expression may be monitored by hybridization of large numbers of mRNAs in parallel using high density arrays of nucleic acids in cells, such as in microorganisms such as yeast, as described in Lockhart et al., Nature Biotechnology, 14:1675-1680 (1996). Bacterial transcript imaging by hybridization of total RNA to nucleic acid arrays may be conducted as described in Saizieu et al., Nature Biotechnology, 16:45-48 (1998). Accessing genetic information using high density DNA arrays is further described in Chee, Science 274:610-614 (1996).

A non-limiting list of potential applications suitable for encoded microparticles and methods relating to the use thereof as described herein includes: pathogens detection and classification; chemical/biological warfare real-time detection; chemical concentration control; dangerous substance (e.g., gas, liquid) detection and alarm; sugar and insulin levels detection in diabetic patients; pregnancy testing; detection of viral and bacterial infectious diseases (e.g. AIDS, Bird Flu, SARS, West Nile virus); environmental pollution monitoring (e.g., water, air); and quality control in food processing.

Another application for the encoded microparticles of the present invention is massively parallel screening in microwells. Such screening may involve small molecule drugs or other therapeutic compounds. An example of a massively parallel screening system comprises: 1) encoded microparticles are dispersed such that substantially only one particle is in each microwell, 2) thousands to millions or more microwells are on a single substrate, such as an etched glass slide, fiber bundle, or microfabricated device, and can contain microliter to picoliter volumes, 3) the particle in each well tracks individual reactions that occur in the microwell, with the reactions taking place on the surface of the particle where precoated biochemical molecules may be present, in the solution of the well where compounds or biochemical moieties may be present (either the same or different ones in each well), or on the inside surface of the well, or on cells that are present in the well (either in solution or on the inside surface, 4) further, molecules may be released from the surface of the particles to effect a reaction; such released molecules may be directly cleaved or may be present in one or more subcontainers that are attached to the particle, with the molecules subsequently being released from the subcontainer; the subcontainer may be a vesicle, 5) molecules to be released may initially be retained in a lipid bilayer, or other type of coating, that surrounds the particle.

In yet another application, encoded microparticles are utilized in bubbles or droplets that may be manipulated. Microparticles comprising codes are incorporated into droplets that can be manipulated to perform biochemical reactions, and for example provide results for a bioassay. Microparticles can be incorporated singly (one particle per droplet) or in multiples (i.e. more than one particle per droplet). A distribution spanning zero, one, or more particles per droplet may be present. Microparticles may comprise surface bound molecules that are involved in the reactions, for example serving as capture probes for target molecules in solution. Microparticles may initially upon introduction into droplets (or droplet formation by the action of a microdevice or microfluidic operation) not have biomolecules bound to their surface and may through manipulation of one or more droplets, becoming functionalized with reacting surface groups and may further have biomolecules attached to the surface of the microparticles. Droplets comprising microparticles, buffers, and reagents (in any combination) may be manipulated in such a way as to cause the division of droplets, fusion of multiple droplets into a single droplet, heating or cooling of the droplets, sorting of droplets based on a property of the droplet (such as size or charge), or other manipulations known in the art. Microparticles with codes that are contained in droplets may be read by optical means and operations performed according to the determined codes. In addition the result of reactions or assays may be read out in the droplet, including by fluorescence, chemiluminescence, radioactivity.

An encoded microparticle-based assay system as described herein can also be a sub-system within a much larger bio-analysis system. The bio-analysis system could include all the aspects of sample preparation prior to, for example, optical detection, the post processing of data collected in the optical detection phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and spotting of the sample into a reaction vessel or site on a substrate. The post processing of the collected data may include: normalization; background and noise reduction; and statistical analysis such as averaging over repeated tests or correlation between different tests. The decision making may include: testing against a predefined set of rules and comparison to information stored in external data-bases.

The applications and uses of the encoded microparticles described herein can produce one or more result useful to diagnose a disease state of an individual, for example, a patient. In one embodiment, a method of diagnosing a disease comprises reviewing or analyzing data relating to the presence and/or the concentration level of a target in a sample. A conclusion based review or analysis of the data can be provided to a patient, a health care provider or a health care manager. In one embodiment the conclusion is based on the review or analysis of data regarding a disease diagnosis. It is envisioned that in another embodiment that providing a conclusion to a patient, a health care provider or a health care manager includes transmission of the data over a network.

Accordingly, business methods relating to the encoded microparticles and methods related to use thereof as described herein are provided. One aspect of the invention is a business method comprising screening patient test samples for the presence or absence of a biologically active analyte to produce data regarding the analyte, collecting the analyte data, providing the analyte data to a patient, a health care provider or a health care manager for making a conclusion based on review or analysis of the data regarding a disease diagnosis. In one embodiment the conclusion is provided to a patient, a health care provider or a health care manager includes transmission of the data over a network.

Figure 53:
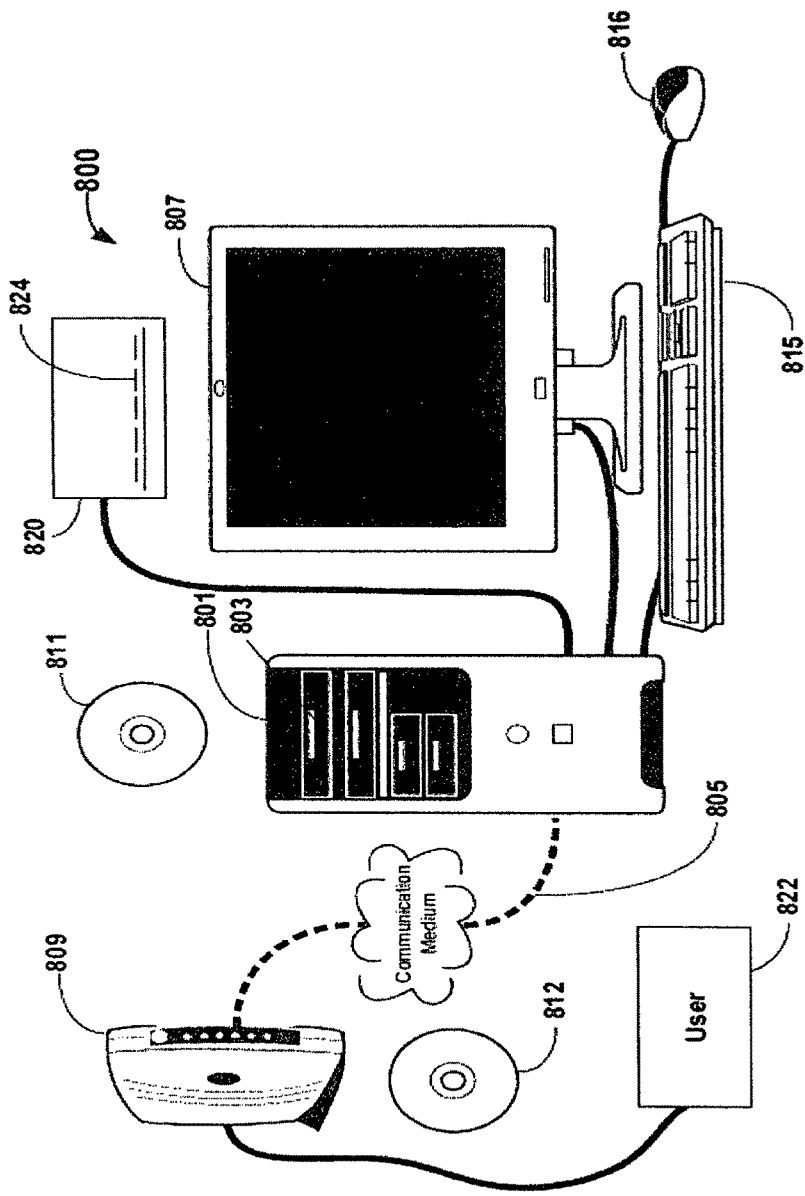
FIG. 53 is a block diagram showing a representative example logic device in communication with an apparatus for use with the encoded microparticles of the invention.

FIG. 53 is a block diagram showing a representative example logic device through which reviewing or analyzing data relating to the present invention can be achieved. Such data can be in relation to a disease, disorder or condition in a subject. FIG. 53 shows a computer system (or digital device) 800 connected to an apparatus 820 for use with the encoded microparticles 824 to, for example, produce a result. The computer system 800 may be understood as a logical apparatus that can read instructions from media 811 and/or network port 805, which can optionally be connected to server 809 having fixed media 812. The system shown in FIG. 53 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. It is envisioned that data relating to the present invention can be transmitted over such networks or connections.

In one embodiment, a computer-readable medium includes a medium suitable for transmission of a result of an analysis of a biological sample. The medium can include a result regarding a disease condition or state of a subject, wherein such a result is derived using the methods described herein.

Another aspect of the invention is a business method comprising screening patient test samples for the presence or absence of a biologically active analyte to produce data regarding the analyte, collecting the analyte data into a database, using one or more algorithms (e.g., a bioinformatic algorithm) to process the collected analyte data to identify one or more diagnostic, therapeutic or marker products, and collaboratively or independently, marketing or commercializing the products.

It will be appreciated by those of skill in the art that a new and useful microparticle and a method of making the same have been described herein. The large sets of encoded microparticles produced by this invention can be a fundamental technology that will have far reaching applications, especially in the field of biotechnology and more specifically genomics. It has the potential to dramatically reduce the cost of highly multiplexed bioassays. Moreover, enables researchers to easily design custom content solution arrays. The researcher can also easily add new particle types to the pooled set, for instance including new found genes of interest with the microparticles of the invention.

In view of the many possible embodiments to which the principles of this invention may be applied, however, it should be recognized that the embodiments described herein with respect to the drawing figures are meant to be illustrative only and should not be taken as limiting the scope of invention. Those of skill in the art will recognize that the illustrated embodiments can be modified in arrangement and detail without departing from the spirit of the invention.

For example, the microparticle may have a six sided shape with four elongated sides and two end sides. The encoded microparticle can be configured such that the code of the encoded microparticle can be detectable regardless of which of the four elongated sides the barcode is disposed on. The microparticle may have a ratio of the length to width is from 2:1 to 50:1, from 4:1 to 20:1. The length of the microparticle is preferably from 5 to 100 um and more preferably less than 50 um. The width of the microparticle can be from 0.5 to 10 um. In other examples, the length of the microparticle can be less than 10 um, less than 25 um, less than 25 um; less than 5 um, less than 27 um; and the width of the microparticle can be less than 3 um. The ratio of width to height of the microparticle can be from 0.5 to 2.0. The ratio of the length to width of the microparticle can be from 2:1 to 50:1. The cross section taken along the length of the microparticle is substantially rectangular with a length at least twice the width.

The microparticle may have a glass body with segments embedded therein. The difference of the transmissivity of the glass body and segments can be 10% or more. The glass body may have a length of less than 50 um and a width of less than 10 um with the glass body having a volume of from 5 to 500 $um^3$. The encoded microparticle may have 2 to 15, 3 to 10, or 4 to 8 portions of less transparent material within the encoded microparticle. The code incorporated in the microparticle can be binary or non-binary or any other desired codes. The microparticle may have biochemical molecules attached to one or more surfaces of the microparticle, such as DNA and RNA probes with a density of from $10^2$ to $10^6/um^2$. When fabricated on the wafer-level, the wafer may have a surface area of from 12.5 $in^2$ to 120 $in^2$, and wherein there are at least 3 million microparticles per $in^2$ of the wafer. The wafer may have at least one million codes are formed on the substrate, or at least two hundred different codes are present within the one million codes, or at least 3000 different codes are present within the one million codes. When placed in a liquid buffer, for example in a bioassay, the microparticles can form a single monolayer wherein the microparticles undergo substantial Brownian motion. The Brownian motion can have a 2 dimensional diffusion coefficient of the microparticles greater than $1 \times 10^{-12}$ $cm^2/s$ and more preferably greater than $1 \times 10^{-11}$ $cm^2/s$. The Brownian motion can comprise more than 10% of the microparticles being measured to undergo a lateral displacement of 20 nm or greater in a time interval of one second or less.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting a biological analyte comprising:
   (a) delivering a sample suspected of containing a biological analyte to a system, wherein the system comprises a plurality of encoded microparticles, and wherein an encoded microparticle comprises:
      (i) an elongated body comprising a plurality of alternating portions of a more transparent material and a less transparent material, wherein the portions of the less transparent material are adjacent to the portions of more transparent material, and wherein the portions of the more and less transparent materials form a spatial code which is detectable; and
      (ii) an outer surface encapsulating the spatial code comprised of glass, silica, silicon dioxide, quartz, silicon nitride, silicon carbide or mixtures thereof; wherein the microparticle has a consistent external cross section shape along a length of the microparticle;
   (b) determining the spatial code for individual microparticles; and (c) determining the presence or absence of a biological analyte by quantifying signals from the plurality of encoded microparticles.

2. The method of claim 1, wherein the system comprises a monolayer of the encoded microparticles.

3. The method of claim 1, wherein the system comprises a liquid buffer, wherein the plurality of encoded microparticles are present in the liquid buffer in a monolayer at a density greater than 1,000 encoded microparticles per square millimeter.

4. The method of claim 1, wherein the encoded microparticle further comprises a square cross section.

5. The method of claim 1, wherein the encoded microparticle comprises a longest dimension of less than 50 µm.

6. The method of claim 1, wherein the encoded microparticle comprises a plurality of indentations in the outer surface.

7. The method of claim 1, wherein the encoded microparticle comprises the more transparent material fully encapsulating the less transparent material.

8. The method of claim 1, wherein the encoded microparticle comprises the less transparent material, and wherein the less transparent material is opaque.

9. The method of claim 1, wherein the encoded microparticle comprises the less transparent material, and wherein the less transparent material comprises a semiconductor or metal.

10. The method of claim 1, wherein the encoded microparticle comprises a magnetic, ferromagnetic, diamagnetic, paramagnetic or supermagnetic material.

11. The method of claim 1, wherein the encoded microparticle comprises code elements that are less than 1.5 microns in length.

12. The method of claim 1, wherein the system comprises biochemical molecules and/or probes attached to the outer surface of the plurality of microparticles.

13. The method of claim 12, wherein the biochemical probes are selected from the group consisting of a nucleic acid, a protein, a peptide, a polypeptide, a polynucleotide, an oligonucleotide, a cell, an antibody, an enzyme, a drug, a receptor, a ligand, a lipid, an antigen, an antibody, a microorganism, a gas, a chemical agent and a pollutant.

14. The method of claim 1 further comprising:
submitting the plurality of microparticles to Brownian motion.

15. The method of claim 1, wherein determining the spatial code for individual microparticles comprises:
transmitting electromagnetic radiation through the microparticles and/or reflecting electromagnetic radiation from the microparticles; and
detecting the transmitted and/or reflected electromagnetic radiation.

16. The method of claim 1, wherein the steps are performed in conducting an assay selected from the group consisting of gene expression, methylation, SNP genotyping, comparative genomic hybridization, microRNA profiling, microbe identification, immunoassay, antibody arrays, protein profiling, protein-protein interaction, receptor-ligand assay, viral identification, bacterial identification and pathogen identification.

17. The method of claim 1, wherein determining the presence or absence of the biological analyte comprises:
(a) contacting the encoded microparticles comprising a biochemical molecule or probe with the biological analyte, wherein the biochemical molecule or probe binds to the corresponding biological analyte in the sample, and wherein the biochemical molecule and/or probe comprises a detectable label and/or the biological analyte comprises a detectable label;

(b) determining the spatial code of the encoded microparticles which remain associated with the biological analyte; and
(c) detecting the presence or absence of a signal from said detectable label, wherein the presence of a signal indicates that said biological analyte is present in said sample.

18. The method of claim 17, wherein determining the presence or absence of the biological analyte further comprises:
determining the spatial code of the encoded microparticles which do not remain associated with the biological analyte.

19. A method of detecting a biological analyte comprising:
(a) delivering a sample suspected of containing a biological analyte to a system comprising a plurality of encoded microparticles, wherein an encoded microparticle comprises:
(i) an elongated body comprising a plurality of alternating portions of a first transparent material and a third material, wherein the third material is less transparent than the first transparent material, and wherein the portions of the third material are adjacent to the portions of the first transparent material, and wherein the portions of the first transparent material and the third material form a spatial code which is detectable,
(ii) an outer surface encapsulating the spatial code comprised of a second transparent material wherein the microparticle has a consistent external cross section shape along a length of the microparticle, and
(iii) a biological molecule or probe attached to the outer surface, wherein the biological molecule or probe has the capacity to bind to a corresponding biological analyte;
(b) determining the spatial code for individual microparticles; and
(c) detecting the presence or absence of a biological analyte by determining the presence or absence of a molecular binding event between the biological molecule or probe and the biological analyte.

20. The method of claim 19, wherein the first transparent material is the same as the second transparent material.

21. The method of claim 19, wherein the encoded microparticle further comprises a square cross section.

22. The method of claim 19, wherein the encoded microparticle comprises a plurality of indentations in the outer surface.

23. The method of claim 1, wherein the encoded microparticle includes the spatial code, the spatial code formed by printing a single code element multiple times within a length of the microparticle.

24. The method of claim 23, wherein the encoded microparticle includes the spatial code, the spatial code formed by exposing the less transparent material to light transmitted through a single reticle multiple times within the length of the microparticle.

25. The method of claim 1, wherein the encoded microparticle includes the spatial code, the spatial code formed by successive printing of a single code element.

26. The method of claim 19, wherein the encoded microparticle includes the spatial code, the spatial code formed by printing a single code element multiple times within a length of the microparticle.

27. The method of claim 26, wherein the encoded microparticle includes the spatial code, the spatial code formed by exposing the less transparent material to light transmitted through a single reticle multiple times within the length of the microparticle.

28. The method of claim 19, wherein the encoded microparticle includes the spatial code, the spatial code formed by successive printing of a single code element.

* * * * *